US009282993B1

(12) United States Patent
Cohen et al.

(10) Patent No.: US 9,282,993 B1
(45) Date of Patent: Mar. 15, 2016

(54) STEERABLE EXTENDABLE DEVICES

(71) Applicant: Southern Methodist University, Dallas, TX (US)

(72) Inventors: Adam Cohen, Dallas, TX (US); Edmond Richer, Richardson, TX (US)

(73) Assignee: SOUTHERN METHODIST UNIVERSITY, Dallas, TX (US)

( * ) Notice: Subject to any disclaimer, the term of this patent is extended or adjusted under 35 U.S.C. 154(b) by 0 days.

(21) Appl. No.: 14/213,193

(22) Filed: Mar. 14, 2014

Related U.S. Application Data

(60) Provisional application No. 61/791,692, filed on Mar. 15, 2013, provisional application No. 61/884,123, filed on Sep. 29, 2013.

(51) Int. Cl.
*A61B 17/34* (2006.01)

(52) U.S. Cl.
CPC ................................. *A61B 17/3421* (2013.01)

(58) Field of Classification Search
USPC .......... 604/528, 905, 536, 523, 524, 525, 526, 604/527, 529, 530, 531, 532, 534; 166/380, 166/381, 542.1
See application file for complete search history.

(56) References Cited

U.S. PATENT DOCUMENTS

| 6,858,005 | B2 | 2/2005 | Ohline et al. | |
| 6,960,163 | B2 | 11/2005 | Ewers et al. | |
| 2003/0135204 | A1 | 7/2003 | Lee et al. | |
| 2004/0243143 | A1* | 12/2004 | Corcoran et al. | 606/108 |
| 2007/0066987 | A1* | 3/2007 | Scanlan et al. | 606/184 |
| 2008/0058596 | A1 | 3/2008 | Bob et al. | |
| 2013/0090598 | A1* | 4/2013 | Vargas | 604/95.04 |
| 2013/0226151 | A1* | 8/2013 | Suehara | 604/533 |
| 2014/0018626 | A1* | 1/2014 | Lee | 600/120 |

OTHER PUBLICATIONS

Chapman, M.P., et al., "A Highly Articulated Robotic System (CardioARM) is Safer than a Rigid System for Intrapericardial Intervention in a Porcine Model," IEEE ICRA Full Day Workshop, 2010.
Degani, A., et al., "Percutaneous Intrapericardial Interventions Using a Highly Articulated Robotic Probe," Proceedings of the 2006 IEEE / RAS-EMBS iNternational Conference on Biomedical Robotics and Biomechatronics, Feb. 2006, pp. 7-12.
Dimaio, S., et al., "Needle Insertion Modeling and Simulation," IEEE Transactions on Robotics and Automation, vol. 19, No. 5, Oct. 2003.
Dupont, P. E., et al., "Design and Control of Concentric-Tube Robots," IEEE Trans Robot., 26(2):209-225, Apr. 1, 2010.

(Continued)

*Primary Examiner* — Kami A Bosworth
*Assistant Examiner* — Hamza Darb
(74) *Attorney, Agent, or Firm* — Edwin S. Flores; Chalker Flores, LLP

(57) ABSTRACT

The present invention is a Distally Assembled Steerable Cannula (DASC), a robotically-manipulated device that can be deployed and extended within a patient's body by growing from its distal end, or can be used in non-medical applications. In one embodiment, growth occurs by sequentially assembling segments that interlock to form a rigid tube with a complex 3-D shape. The segments are individually transported through the growing cannula, and then assembled at the distal end. A segment can be wedge-shaped in profile, allowing adjustment of the local radius of curvature and direction of the cannula to be controlled by relative segment orientation.

32 Claims, 51 Drawing Sheets

(56) References Cited

OTHER PUBLICATIONS

Dupont, P.E., et al., "Concentric Tube Robots for Minimally Invasive Surgery," The Hamlyn Symposium on Medical Robots, 2012.

Gosline, A., et al., "Percutaneous intracardiac beating-heart surgery using metal MEMS tissue approximation tools," Int. J. Rob. Res., 31(9):1081-1093, Aug. 1, 2012.

Majewicz, A., et al., "Behavoir of Tip-Steerable Needles in ex vivo and in vivo Tissue," IEEE Trans Biomed Eng., 59(10):2705-2715, Oct. 2012.

Sears, P., et al., "A Steerable Needle Technology Using Curved Concentric Tubes," IEEE/RSJ International Conference on Intelligent Robots and System, pp. 2850-2856, Oct. 9-15, 2006.

Webster, R. J., et al., "Mechanics of Precurved-Tube Continuum Robots," IEEE Transactions on Robotics, vol. 25, No. 1, Feb. 2009.

Glozman, D., et al., "Image-guided robotic flexible needle steering," IEEE Trans. Robot., vol. 23, No. 3, Jun. 2007, pp. 459-467.

Okazawa, S., et al., "Hand-held steerable needle device," IEEE/ASME Trans. Mechatron., vol. 10, No. 3, Jun. 2005, pp. 285-296.

Webster, R., et al., "Nonholonomic modeling of needle steering," Int. J. Robot. Res., vol. 25, No. 5-6, pp. 509-525, May-Jun. 2006.

Goksel, O., et al., "Modeling and simulation of flexible needles," Medical Engineering & Physics, Jul. 7, 2009, 7:1153-1162.

Mahvash, M., et al., "Toward a hybrid snake robot for single-port surgery," 33rd Annual International Conference of the IEEE EMBS, Boston, MA, Aug. 30-Sep. 3, 2011:5372-5375.

\* cited by examiner (a)

(a)

(b)　　　　　　　　　　(c)

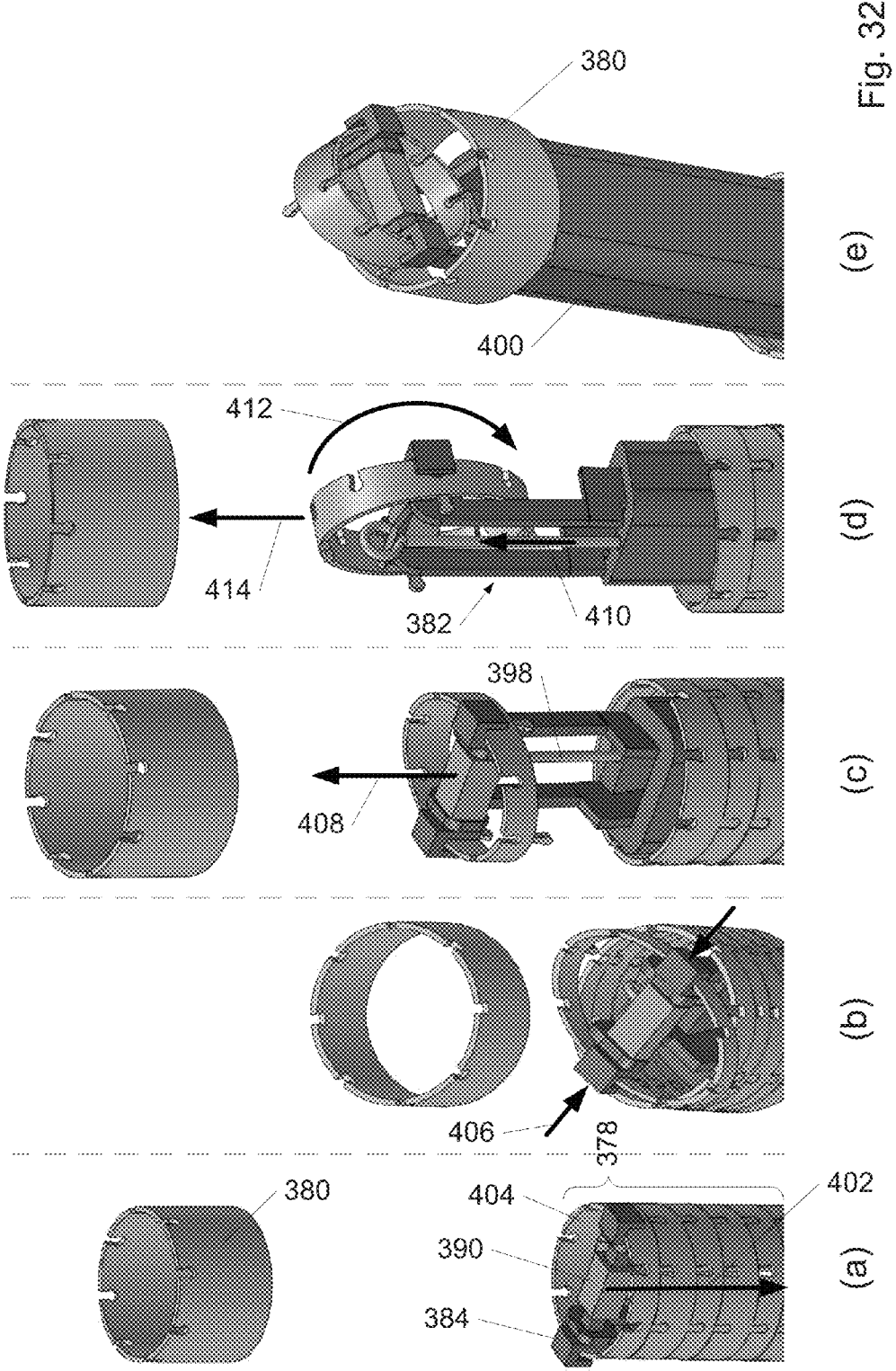

STEERABLE EXTENDABLE DEVICES

CROSS-REFERENCE TO RELATED APPLICATIONS

This application claims priority to U.S. Provisional Application Ser. No. 61/791,692, filed Mar. 15, 2013, and U.S. Provisional Application Ser. No. 61/884,123, filed Sep. 29, 2013, the entire contents of each of which are incorporated herein by reference.

TECHNICAL FIELD OF THE INVENTION

The present invention relates generally to the fields of medical devices, robotics, oil and gas, civil engineering, disaster robotics, as well as other fields.

STATEMENT OF FEDERALLY FUNDED RESEARCH

None.

BACKGROUND OF THE INVENTION

This application relates primarily to medical procedures which comprise entering the patient's body with an instrument to remove, ablate, extract, aspirate, modify, or repair tissue and fluids; to perform diagnostic procedures; or to deliver therapeutic agents or devices. The application also relates to implanted devices and to non-medical devices.

Some medical procedures are minimally invasive; such procedures can improve outcomes, speed recovery, limit trauma, and allow earlier intervention. Cannulas and related devices such as needles, catheters, and endoscopes are commonly used in such procedures, allowing surgical tools (including powered tools such as microdebriders driven by rotating flexible shafts), diagnostic and therapeutic instruments, implants, and drugs to be introduced into the body and excised tissue and fluid to be removed. Yet due to obstructions such as bone or sensitive organs, current devices may be unable to access a target region, or only do so sub-optimally. A more invasive method, a riskier approach, or a worse outcome is thus sometimes unavoidable. Moreover, in a number of procedures for which multiple targeted regions within the body need to be accessed, it can be time-consuming and involve multiple punctures or incisions, even if access to a single region would be straightforward. These issues arise from the fact that many instruments are substantially rigid and straight and follow substantially straight paths within the body, whether within a hollow (i.e., gas- or liquid-filled) organ or lumen, or in solid tissue. Moreover, even instruments known to the art that are not rigid and/or not straight can also have difficulty in accessing certain regions of the body, as the following examples will illustrate.

There has been extensive research into steerable needles, cannulas, catheters, and endoscopes; snake-like robots; and other devices. To date such devices have been problematic and many remain experimental. Spinning steerable needles with asymmetric tips [1, 2, 3, 4] offer small gauge sizes but have very large curvature/outer diameter (O.D.) ratios (e.g., 70:1 [5]), can only be deployed within solid tissue, and are difficult to control accurately due to varying tissue properties [6], etc. Concentric multi-tube superelastic nickel-titanium (Nitinol) needles [7, 8, 9, 10, 11] intended mostly for hollow regions offer relatively few shapes due to the small number of tubes; relatively large curvature/O.D. ratios [12]; limited stiffness; and small lumen/outside diameter ratios. Steerable catheters [13] and jointed, shape locking devices [14] have few degrees of freedom and sometimes large diameters. Snake-like robots [15, 16, 17] capable of following 3-D paths are typically 0.4-0.8" diameter and use costly components; their lumen or inner diameter (I.D)/O.D. ratios also tend to be small. Finally, everting endoscopes [18] grow distally and are flexible but not steerable.

Given the limitations of instruments known to the art, there is a need for new, more capable and dexterous instruments capable of curved motion along desirable paths within the body, either within hollow (e.g., gas- or liquid-filled) regions or through solid tissue. Such instruments would preferably be deliverable with minimal difficulty and tissue trauma or damage and have a small outside diameter (e.g., 1-5 mm). They could provide a unique platform technology with the potential to impact a wide variety of medical specialties and procedures, including sinus and skull base surgery (where narrow passages and nearby critical structures make minimally invasive procedures difficult or impossible with current straight or angled instruments, e.g. in the frontal sinus, anterior cranial fossa, cavernous sinus, and brainstem), urology (where, for example, repeated access to specific regions of the kidney can be difficult), and interventional radiology (e.g., for biopsy and drainage while avoiding critical structures, and local regional therapy). Moreover, there is a need (e.g., for cochlear electrodes and annuloplasty rings) for implantable devices that can be delivered in a minimally invasive manner and which have complex 3-D curved shapes; this capability is currently very limited and could be greatly expanded by using the approaches of some embodiments of the invention.

SUMMARY OF THE INVENTION

According to some embodiments of the invention, a small-diameter, stable, controllable cannula is provided that follows an optimal 3-D path—through gas or liquid-filled volumes or solid tissue—to reach virtually any target at any approach angle, and do so without iterative, time-consuming, and potentially traumatic manipulation by the clinician. FIG. 4(a-c) depicts this ideal sequence, in which the device extends along a path while steered and assembled robotically in-vivo so as to grow into a complex 3-D shape within the body while the more distal regions of the device retain their original shape.

Such a device, which we term a "distally-assembled steerable cannula" (hereinafter, "DASC"), is fundamentally different from existing steerable needles, cannulas, catheters, and snake robots that rely on distally sliding and articulating. DASC is unique in several aspects. For example, it is deployed within a patient's body entirely through distal growth, extending at its tip to follow a controlled 3-D path, while shape is maintained everywhere along the device. Moreover, it may be assembled in vivo from multiple, discrete pieces (interlocking segments or rings), or grow as an everting, steerable tube, offering an unprecedented number of possible shapes. DASC offers the ability to make tight turns (e.g., a 2:1 radius of curvature to O.D. ratio); for example, a 0.120" O.D. device could make a full 180° turn in a space only ~0.7" wide. DASC also provides an unusually large lumen/working channel (e.g., a 0.9:1.0 lumen/O.D. ratio)—comparable to a non-steerable catheter—enabling more instruments to be used simultaneously; improving endoscopic visualization, irrigation, and aspiration; and allowing more tissue to be excised (e.g., for biopsy or tumor resection).

DASC can serve as a stable, passive conduit that provides access and support to other devices (e.g., articulated endoscopes, forceps, or other instruments, which can be rapidly exchanged), for example, in endoscopic surgery or natural orifice translumenal endoscopic surgery, or to infuse or aspirate liquids. However, unlike prior-art passive devices, DASC can be easily re-shaped distally without having to first withdraw it and re-insert it during a procedure. Thus DASC can be disassembled partially and then reassembled such that the distal end moves to a new position and/or changes its approach angle to the target region, providing, for example, a stable platform for procedures which cover multiple sites or wide areas.

DASC can be image-guided (e.g., via pre- or peri-operative CT, fluoro (portions of DASC may be made radiopaque), MRI, ultrasound, and/or direct visualization), can be "driven" precisely in real time by a clinician (e.g., using a joystick), or can automatically grow according to an optimal, pre-determined trajectory, with optional real-time correction. It could be optimized for rigidity (e.g., for tissue manipulation) or instead, for compliance, e.g., to approximate the modulus of tissue. The tip of a DASC device can be made to sense force, helping a clinical detect obstructions and choose an optimal trajectory for deployment.

In some embodiments, DASC grows from its distal end by sequentially assembling flexible segments or rings that interlock to form a rigid, self-supporting tube with a complex, programmable 3-D shape. The segments or rings are temporarily deformed and individually transported through the growing cannula by a flexible shaft or "smart stylet" (hereinafter the "stylet"), then assembled by the stylet at the distal end. Each ring is wedge-shaped in profile; by robotically mating the ring at a preset orientation with respect to the next-most-proximal ring, the local radius of curvature and direction of the cannula can be precisely controlled. A fully-deployed cannula may comprise over 100 rapidly-assembled segments or rings. Since each ring can be mated in a number (e.g., eight or more) orientations, the range of possible 3-D configurations—and thus cannula's reachable workspace and set of approach angles—is vast. DASC can be scaled down to an O.D. (outside diameter) as small as 0.04" (1 mm, 3 French) with a lumen ≥90% of the O.D., or can be scaled larger if required. As an example of a DASC suitable for sinus surgery, dimensions might be 0.12-0.16" O.D., 0.09-0.13" I.D. (inside diameter), 4-5" overall length, and 0.3-0.4" radius of curvature.

In one embodiment, the present invention includes an elongatable, steerable apparatus capable of growing from a proximal end to a distal end through a process of assembly wherein one or more segments are added to the distal end of the apparatus, the apparatus comprising: a first segment having a lumen therethrough, the first segment having a proximal end and a distal end; and a second segment having a lumen, a proximal end, and a distal end, wherein the second segment is deliverable via a segment transporter to the distal end of the first segment, wherein the segment transporter attaches the second segment to the first segment, wherein the second segment is capable of changing the growth direction of the distal end of the apparatus and of one or more subsequent segments. In one aspect, additional segments are transferred to the distal end through the lumen formed of at least one of the first, the second and one or more subsequent segments. In another aspect, the growth is the result of everting a tube formed by two or more segments. In another aspect, the growth is the result of transferring additional segments to the distal end. In another aspect, at least the first, second or subsequent segments are at least one of triangular, circular, elliptical, polygonal, rectangular, square, or combination thereof. In another aspect, the at least first, second or subsequent segments comprise at least one of plastic, metal, rubber, latex, polymer, composite, elastomer, thermoplastic elastomer, synthetic rubber, natural rubber, melt processable rubber, propylene oxide elastomer, ethylene-isoprene elastomer, elastic polyvinyl chloride, silicone elastomer, elastic polyurethane, ethylene-vinyl acetate elastomer, or non-polymeric elastomer. In another aspect, at least the first, second or subsequent segments are metal and comprise at least one of titanium, vanadium, aluminum, nickel, tantalum, zirconium, chromium, silver, gold, silicon, magnesium, niobium, scandium, platinum, cobalt, palladium, manganese, molybdenum and alloys thereof, zirconium-titanium-tantalum alloys, superelastic nickel-titanium, and stainless steel. In another aspect, the segment transporter is defined further as a stylet that is comprised of at least one of a superelastic nickel-titanium, stainless steel, plastic, thermoplastic, elastomer, polyethylene terephthalate, polyethylene terephalate glycol-modified, rubber, vinyl, latex, or silicone. In another aspect, at least one segment may be radiopaque. In another aspect, at least the first, second, or subsequent segments, may attach or interlock to each other by friction, abrasive contact surfaces, self-adhesive strips, hook and loop fasteners, hooks and eyes, ties, tabs, holes, buckles, belts, pins, elastic bands, rubber bands, snaps, clasps, DUAL LOCK™ or VELCRO® tape fasteners. In another aspect, at least the first, second, or subsequent segments, are wedge-shaped and the addition of subsequent segments causes the extension of the apparatus at the distal end with a segment that is not wedge-shaped, a segment that is wedge-shaped on the distal or the proximal face, or a segment that is wedge-shaped on both the distal and proximal faces. In another aspect, at least the first, second, or subsequent segments, are wedge-shaped having a wedge angle that varies from 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, or 85 degrees at the proximal or distal face, or on both faces. In another aspect, at least the first, second, or subsequent segments, are wedge-shaped and the segments interlock in increments of 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, 85, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, or 360 degrees about the longitudinal axis of the apparatus. In another aspect, at least the first, second, or subsequent segments, are wedge-shaped but also tapered along the longitudinal axis of the apparatus to expand or decrease an inner diameter of the apparatus. In another aspect, the central cannula is defined further as a having a proximal and distal end, wherein the segment transporter travels back and forth within the cannula to at least one of compress, swivel, transport, rotate, or add the subsequent segments to the distal end of the apparatus. In another aspect, the cannula is pre-loaded with some or all the segments necessary to reach a pre-determined length and shape.

In another embodiment, the present invention includes a method of lengthening and steering an apparatus capable of growing from a proximal end to a distal end through a process of assembly wherein one or more segments are added to the distal end of the apparatus, the apparatus comprising: obtaining a first segment having a lumen therethrough, the first segment having a proximal end and a distal end; and adding a second segment having a lumen, a proximal end, and a distal end, wherein the second segment is deliverable via a segment transporter to the distal end of the first segment, wherein the segment transporter attaches the second segment to the first segment, wherein the second segment is capable of changing the growth direction of the distal end of the apparatus and of one or more subsequent segments. In one aspect, additional segments are transferred to the distal end through the lumen formed of at least one of the first, the second and one or more subsequent segments. In another aspect, the growth is the result of everting a tube formed by the two or more segments. In another aspect, the growth is the result of transferring additional segments to the distal end. In another aspect, at least the first, second or subsequent segments are at least one of triangular, circular, elliptical, polygonal, rectangular, square, or combination thereof. In another aspect, the at least first, second or subsequent segments comprise at least one of plastic, metal, rubber, latex, polymer, composite, elastomer, thermoplastic elastomer, synthetic rubber, natural rubber, melt processable rubber, propylene oxide elastomer, ethylene-isoprene elastomer, elastic polyvinyl chloride, silicone elastomer, elastic polyurethane, ethylene-vinyl acetate elastomer, or non-polymeric elastomer. In another aspect, at least the first, second or subsequent segments are metal and comprise at least one of titanium, vanadium, aluminum, nickel, tantalum, zirconium, chromium, silver, gold, silicon, magnesium, niobium, scandium, platinum, cobalt, palladium, manganese, molybdenum and alloys thereof, zirconium-titanium-tantalum alloys, superelastic nickel-titanium, or stainless steel. In another aspect, the segment transporter is defined further as a stylet that is at least one of a superelastic nickel-titanium, stainless steel, plastic, thermoplastic, elastomer, polyethylene terephthalate, polyethylene terephtalate glycol-modified, rubber, vinyl, latex, or silicone. In another aspect, at least the first, second, subsequent segments, or the cannula is radiopaque. In another aspect, at least the first, second, or subsequent segments, may attach or interlock to each other by friction, abrasive contact surfaces, self-adhesive strips, hook and loop fasteners, hooks and eyes, ties, tabs, holes, buckles, belts, pins, elastic bands, rubber bands, snaps, clasps, Dual Lock™, or Velcro™ tape fasteners. In another aspect, at least the first, second, or subsequent segments, are wedge-shaped and the addition of subsequent segments causes the extension of the apparatus at the distal end with a segment that is not wedge-shaped, a segment that is wedge-shaped on the distal or the proximal face, or a segment that is wedge-shaped on both the distal and proximal faces. In another aspect, at least the first, second, or subsequent segments, are wedge-shaped having a wedge angle that varies from 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, or 85 degrees at one or both ends. In another aspect, at least the first, second, or subsequent segments, are wedge-shaped and the segments interlock in increments of 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, 85, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, or 360 degrees about the longitudinal axis of the apparatus. In another aspect, at least the first, second, or subsequent segments, are wedge-shaped but also tapered along the longitudinal axis the apparatus to expand or decrease an inner diameter of the apparatus. In another aspect, the central cannula is defined further as a having a proximal and distal end, wherein the segment transporter travels back and forth within the cannula to at least one of compress, swivel, transport, rotate, or add the subsequent segments to the distal end of the apparatus. In another aspect, the cannula is pre-loaded with some or all the segments necessary to reach a pre-determined length and shape.

In another embodiment, the present invention includes a cannula capable of growing from a proximal end to a distal end and capable of a non-linear configuration comprising: one or more segments having a lumen and substantially cylindrical in their uncompressed state and having a distal face and a proximal face that are non-parallel, wherein the one or more segments can be transformed into a non-cylindrical, substantially elliptical shape; a segment transporter that transports one or more additional segments in their non-cylindrical, substantially elliptical shape through the substantially cylindrical segments; and a coupling mechanism that engages the one or more segments to an adjacent segment, whereby at least one of the segments is transported through the lumen of the one or more substantially cylindrical segments to reach a distal location, and transformed to couple to the most distal of the segments, thereby growing the cannula. In one aspect, the segment transporter is capable of at least one of swiveling, rotating, coupling or transporting a segment. In another aspect, a swiveling axis of the segment is substantially parallel to a minor axis of the non-cylindrical, substantially elliptical shape of the segment. In another aspect, a distal face of a first segment is substantially perpendicular to a substantially cylindrical axis of the first segment, and a proximal face of a first segment is substantially non-perpendicular to the substantially cylindrical axis of the first segment; a distal face of a second segment is substantially non-perpendicular to a substantially cylindrical axis of the second segment, and a proximal face of a second segment is substantially perpendicular to the substantially cylindrical axis of the second segment; and wherein the swiveling axis is substantially perpendicular to a plane formed by the substantially cylindrical axis and a normal to the substantially non-perpendicular face of the segment. In another aspect, the segments comprise one or more holes along a distal edge or face of the segment and one or more tabs that extend from a proximal edge or face of the segments, wherein the one or more tabs fit within the one or more holes to couple two adjacent segments. In another aspect, each segment comprises two or more tabs that are equally spaced around the circumference of the segment. In another aspect, the tabs are substantially aligned with the major and minor axes of the substantially elliptical shape assumed by the rings when transformed. In another aspect, each segment comprises two holes that are substantially parallel to the swiveling axis. In another aspect, at least one first tab in the distal segment of a pair of adjacent segments enters a hole in the proximal segment of a pair of adjacent segments from the inside of the proximal segment, and at least one second tab on the non-opposite side of the distal segment enters a hole from the outside of the proximal segment to couple the segments. In another aspect, each of the first and second segments alternate.

In another embodiment, the present invention includes an elongatable, steerable cannula capable of growing from a proximal end to a distal end through a process of assembly wherein one or more segments are added to the distal end of the cannula, the cannula comprising: a first flexible segment substantially cylindrical in axial cross section when uncompressed and substantially elliptical when compressed, having a first lumen therethrough, the first segment having a first proximal face substantially perpendicular to a first substantially cylindrical axis and provided with one or more first male coupling elements, and a first distal face substantially non-perpendicular to the substantially cylindrical axis and provided with a first plurality of female coupling elements; a second flexible segment substantially cylindrical in axial cross section when uncompressed and substantially elliptical when compressed, having a second lumen therethrough, the second segment having a second proximal face substantially non-perpendicular to a second substantially cylindrical axis and provided with one or more second male coupling elements, and a second distal face substantially perpendicular to the second substantially cylindrical axis and provided with a second plurality of female coupling elements; a flexible shaft provided with grippers able to grip said first and said second segment to compress and allow to decompress said segments, swivel or allow to swivel said segments about axes substantially parallel to the minor axes of said first and second segments when compressed and substantially elliptical, and transport said segments through said lumen; wherein said flexible shaft transports said second segment through said lumen of said first segment, then rotates said second segment as required around an axis substantially coincident with the longitudinal axis of the flexible shaft, brings the proximal face of said second segment in contact with the distal face of said first segment, allows said second segment to decompress while allowing two of said second male coupling elements to enter two of said first plurality of female coupling elements from the inside and two of said second male coupling elements to enter two of said first plurality of female coupling elements from the outside; and wherein said flexible shaft transports said first segment through said lumen of said second segment, rotates said first segment as required around an axis substantially coincident with the longitudinal axis of the flexible shaft, brings the proximal face of said first segment in contact with the distal face of said second segment, then allows said first segment to decompress while allowing two of said first male coupling elements to enter two of said second plurality of female coupling elements from the inside and two of said first male coupling elements to enter two of said second plurality of female coupling elements from the outside. In another aspect, the segments comprise a superelastic nickel-titanium material. In another aspect, the first and second male coupling elements comprise interlocking male and female elements such that the adjacent segments are mechanically interlocked when the segments are decompressed. In another aspect, a plurality of first and second segments are arranged in an alternating pattern within the cannula. In another aspect, the angle between the first proximal face and second distal face is varied by varying the relative orientation of the first and second segments when coupled together. In another aspect, the relative orientation is varied as required by rotating the second segment substantially about an axis substantially coincident with the longitudinal axis of the flexible shaft prior to coupling the second segment to the first segment. In another aspect, the flexible shaft comprises a superelastic nickel-titanium material. In another aspect, the minor axis of the compressed, substantially elliptical second segment is substantially perpendicular to the plane defined by the substantially non-perpendicular second proximal face and the second substantially cylindrical axis, and wherein the minor axis of the compressed, substantially elliptical first segment is substantially perpendicular to the plane defined by the substantially non-perpendicular first distal face and the first substantially cylindrical axis. In another aspect, the second segment is swiveled about its minor axis and its major axis is substantially parallel to the first cylinder axis during transport by the flexible shaft, and wherein the first segment is swiveled about its minor axis and its major axis is substantially parallel to the second cylinder axis during transport by the flexible shaft. In another aspect, the second segment is rotated as required relative to the first segment prior to allowing the second segment to decompress, and wherein the first segment is rotated relative to the second segment prior to allowing the first segment to decompress. In another aspect, the grippers are supported by a fork that is compressed by a sliding tube. In another aspect, the grippers are supported by a flexible ring that is expanded by applying tension to a wire attached to its distal end.

In another embodiment, the present invention includes an elongatable, steerable cannula capable of growing from a proximal end to a distal end through a process of assembly wherein one or more segments are added to the distal end of the cannula, the cannula comprising: a first expandable segment substantially cylindrical in axial cross section having a first lumen therethrough, the first segment having a first proximal face substantially perpendicular to a first substantially cylindrical axis and provided with a first plurality of male coupling elements, and a first distal face substantially non-perpendicular to the substantially cylindrical axis and provided with a first plurality of female coupling elements; a second expandable segment substantially cylindrical in axial cross section having a second lumen therethrough, the second segment having a second proximal face substantially non-perpendicular to a second substantially cylindrical axis and provided with a second plurality of male coupling elements, and a second distal face substantially perpendicular to the second substantially cylindrical axis and provided with a second plurality of female coupling elements; a flexible shaft provided with an expanding member to expand and orient said first and said second segments, and transport said segments through said lumens; wherein said flexible shaft transports said second segment through said lumen of said first segment, then expands said second segment and allows second plurality of male coupling elements to enter said first plurality of female coupling elements from the inside; and wherein said flexible shaft transports said first segment through said lumen of said second segment, then expands said first segment and allows first plurality of male coupling elements to enter said second plurality of female coupling elements from the inside.

In one embodiment, the present invention also includes an elongatable, steerable cannula capable of growing from a proximal end to a distal end through a process of everting, the cannula comprising: an expandable tube having a relatively flexible inner wall of relatively small diameter and an relatively inflexible outer wall of relatively large diameter; a device for everting the tube to grow the cannula from its distal end by progressively transforming the inner wall into an outer wall; a steering mechanism for controlling the direction in which the cannula grows by varying the rate at which the inner wall is transformed into outer wall according to location around the circumference of the inner wall. In one aspect, the tube comprises braided superelastic nickel-titanium wire. In another aspect, the tube comprises an elastomer.

In another embodiment, the present invention includes a method of making an elongatable, steerable cannula capable of growing from a proximal end to a distal end through a process of assembly wherein one or more segments are added to the distal end of the cannula, the method comprising: obtaining a first flexible segment substantially cylindrical in axial cross section when uncompressed and substantially elliptical when compressed, having a first lumen therethrough, the first segment having a first proximal face substantially perpendicular to a first substantially cylindrical axis and provided with one or more first male coupling elements, and a first distal face substantially non-perpendicular to the substantially cylindrical axis and provided with a first plurality of female coupling elements; positioning a second flexible segment substantially cylindrical in axial cross section when uncompressed and substantially elliptical when compressed, having a second lumen therethrough, the second segment having a second proximal face substantially non-perpendicular to a second substantially cylindrical axis and provided with one or more second male coupling elements, and a second distal face substantially perpendicular to the second substantially cylindrical axis and provided with a second plurality of female coupling elements; inserting a flexible shaft provided with grippers able to grip said first and said second segment to compress and allow to decompress said segments, swivel or allow to swivel said segments about axes substantially parallel to the minor axes of said first and second segments, and transport said segments through said lumen; wherein said flexible shaft transports said second segment through said lumen of said first segment, rotates said second segment as required around an axis substantially coincident with the longitudinal axis of the flexible shaft, brings the proximal face of said second segment in contact with the distal face of said first segment, then allows said second segment to decompress while allowing two of said second male coupling elements to enter two of said first plurality of female coupling elements from the inside and two of said second male coupling elements to enter two of said first plurality of female coupling elements from the outside; and wherein said flexible shaft transports said first segment through said lumen of said second segment, rotates said first segment as required around an axis substantially coincident with the longitudinal axis of the flexible shaft, brings the proximal face of said first segment in contact with the distal face of said second segment, then allows said first segment to decompress while allowing two of said first male coupling elements to enter two of said second plurality of female coupling elements from the inside and two of said first male coupling elements to enter two of said second plurality of female coupling elements from the outside.

In another embodiment, the present invention includes a method of making an elongatable, steerable cannula capable of growing from a proximal end to a distal end through a process of assembly wherein one or more segments are added to the distal end of the cannula, the cannula comprising: obtaining a first expandable segment substantially cylindrical in axial cross section having a first lumen therethrough, the first segment having a first proximal face substantially perpendicular to a first substantially cylindrical axis and provided with a first plurality of male coupling elements, and a first distal face substantially non-perpendicular to the substantially cylindrical axis and provided with a first plurality of female coupling elements; positioning a second expandable segment substantially cylindrical in axial cross section having a second lumen therethrough, the second segment having a second proximal face substantially non-perpendicular to a second substantially cylindrical axis and provided with a second plurality of male coupling elements, and a second distal face substantially perpendicular to the second substantially cylindrical axis and provided with a second plurality of female coupling elements; and inserting a flexible shaft provided with an expanding member to expand and orient said first and said second segments, and transport said segments through said lumens; wherein said flexible shaft transports said second segment through said lumen of said first segment, rotates said second segment as required around an axis substantially coincident with the longitudinal axis of the flexible shaft, brings the proximal face of said second segment in contact with the distal face of said first segment, then expands said second segment and allows said second plurality of male coupling elements to enter said first plurality of female coupling elements from the inside; and wherein said flexible shaft transports said first segment through said lumen of said second segment, rotates said first segment as required around an axis substantially coincident with the longitudinal axis of the flexible shaft, brings the proximal face of said first segment in contact with the distal face of said second segment, then expands said first segment and allows said first plurality of male coupling elements to enter said second plurality of female coupling elements from the inside.

In another embodiment, the present invention includes a method of making an elongatable, steerable cannula capable of growing from a proximal end to a distal end through a process of everting, the cannula comprising: obtaining a flexible, expandable tube capable of being everted, positioning a device for everting the tube to grow the cannula from its distal end by progressively transforming the inner wall into an outer wall, rigidifying the outer wall as it is formed; and inserting a steering mechanism for controlling the direction in which the rigid outer wall grows by varying the rate, according to location around the circumference of the inner wall, at which the inner wall is transformed into the outer wall

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
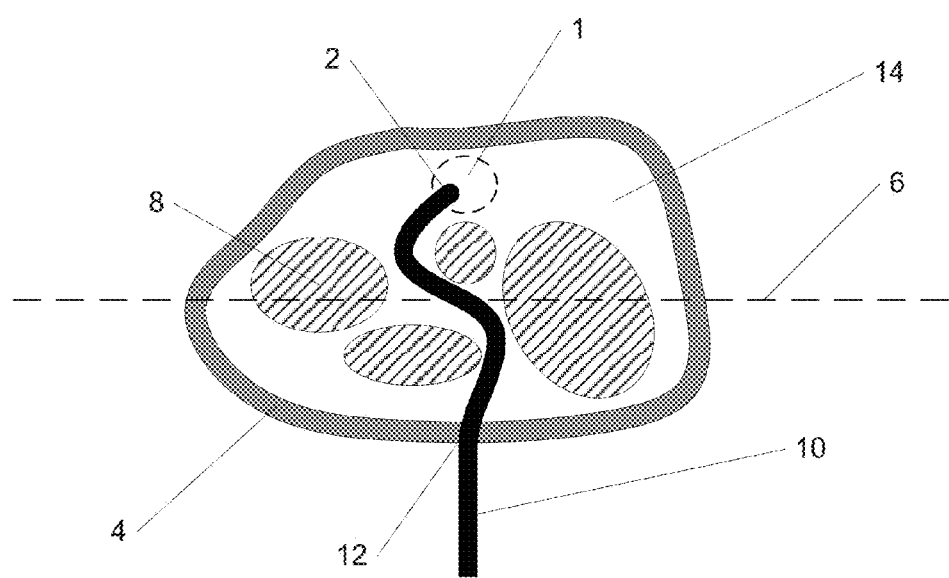
FIG. 1 depicts a schematic cross section of a section of a human body along with a medical device, a target region, and obstacles.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the units that may be used to add or reduce the length of an apparatus of the present invention may be referred to individually as a segment or ring, when there are two or more they can be referred to as segments or rings. The segment(s) or ring(s) the may be of any shape or shapes, including, e.g., triangular, circular, elliptical, polygonal, rectangular, square, or combinations thereof, including composite shapes, and extensions from the edge(s) of the segments or openings cut into the segments. Note also that the terms segment and ring may be used interchangeably herein.

The segment(s) can be made from, e.g., plastic, metal, rubber, latex, polymer, composite, elastomeric, a thermoplastic elastomer, a synthetic rubber, a natural rubber, a melt-processable rubber, a propylene oxide elastomer, an ethylene-isoprene elastomer, an elastic polyvinyl chloride, a silicone elastomer, an elastic polyurethane, an ethylene-vinyl acetate elastomer, or a non-polymeric elastomer, or combinations thereof. The segments or rings can be made from a wide variety of materials or composites, which can include polymer(s) selected from at least one of polyglycolic acid (PGA), polylactic acid (PLA), poly (dioxanone) (PDO), poly (1-lactide) (LPLA), poly (dl-lactide) (DLPLA), poly (glycolide-co-trimethylene carbonate) (PGA-TMC), poly (1-lactide-co-glycolide) (PGA-LPLA), poly (dl-lactide-co-glycolide) (PGA-DLPLA), poly (1-lactide-co-dl-lactide) (LPLA-DL-PLA), poly(glycolide-co-trimethylene carbonate-co-dioxanone) (PDO-PGA-TMC), poly(ε-caprolactone), poly(dioxanone)(a polyether-ester), poly (lactide-co-glycotide), poly (SA-HDA anhydride), poly(orthoester), or polyglyconate. The segments or rings may be at least partially made from a metal, such as, e.g., titanium, vanadium, aluminum, nickel, tantalum, zirconium, chromium, silver, gold, silicon, magnesium, niobium, scandium, platinum, cobalt, palladium, manganese, molybdenum and alloys thereof, zirconium-titanium-tantalum alloys, nitinol (nickel-titanium), and stainless steel.

As regards the central cannula or segment delivery and removal device, it can include an expandable portion that can be, e.g., plastic, thermoplastic, elastomer, polyethylene terephthalate, polyethylene terephtalate glycol-modified, rubber, vinyl, latex, and silicone. Non-limiting examples of a stylet or assembly head is shown herein that include one or more clasps that permit the addition or removal of a segment or ring while also providing orientation for the segment or ring, e.g., to change the direction of the opening within the elongatable apparatus and thus the outside of the apparatus as well.

The segments can be attached to each other via a wide variety of fasteners or adhesives, which can be integrated into the segments themselves. Non-limiting examples of these fasteners or adhesives include tabs and openings in the top, bottom or side walls of the segment(s) that attach or interlock to each other by friction, mechanical interlocking, abrasive contact surfaces, self-adhesive strips, hook and loop fasteners, hooks and eyes, ties, tabs, buckles, belts, pins, elastic bands, rubber bands, snaps, clasps, DUAL LOCK™ (3M™ Company, St. Paul, Minn.), and VELCRO® tape fasteners.

As regards the change in direction by the addition of segments, the segments can be wedge-shaped such that when viewed perpendicular to the segment axis the segment comprising a "wedge angle", such that addition of a subsequent segment can cause the extension to be straight (i.e., continue in the same direction as the next most proximal segment), or cause a rotation (i.e., a change in direction) of the addition as a result of the wedge angle. In certain non-limiting examples, the wedge angle can vary from, e.g., 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, or 85 degrees between segment(s) at one or both ends.

FIG. 1 depicts a hypothetical cross section of a portion of a patient's body, when the present invention is used in a medical context. Suppose that a physician needs to access target region 1 with the distal end 2 of an instrument, and is constrained to introduce the instrument through the skin 4 below dashed line 6. There may be no way do this using a straight instrument while avoiding contact with obstacles such as delicate or difficult-to-penetrate (e.g., bone) anatomical structures 8. Such structures may be surrounded by gas, liquid, or other tissue 14.

Figure 2:
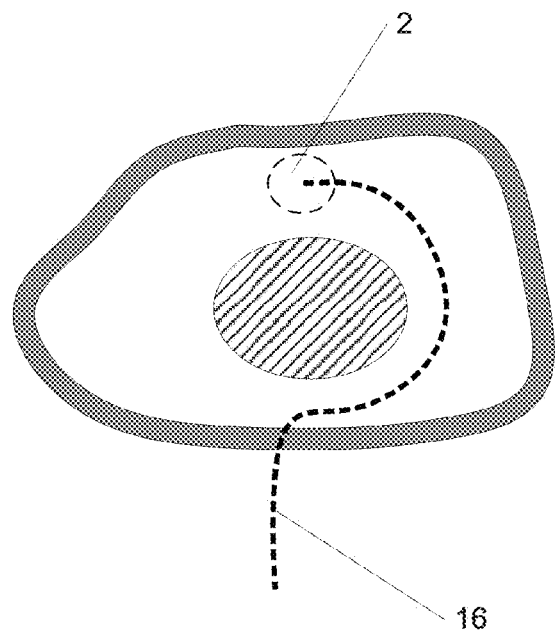
FIGS. 2(a)-(b) depict an ideal path to a target region and the inability of a first prior art device to reach it.
Figure 2:
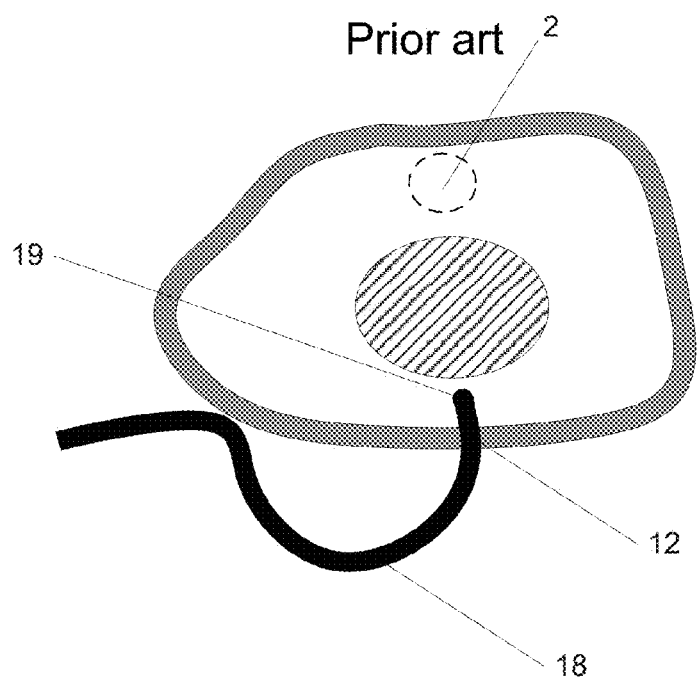

Known to the art are three basic methods by which an instrument 10 can be curved with the goal of its distal end reaching region 2. Referring to FIGS. 1, 2(a) and 2(b) depicting a simpler hypothetical cross section of a patient's body, in the first method, the preferred path to region 2 might be along path 16, avoiding structure 14. If the instrument 18 is substantially rigid but is pre-curved into a 3-D (or planar 2-D) shape as shown in FIG. 2(*b*), it may then be inserted through puncture site 12 with the goal of manipulating it so its distal end 19 reaches region 2. However, as shown in FIG. 2(*b*), such manipulation can be difficult or impossible. The instrument shape would correspond to the desired path once the distal end 19 has reached region 2, but in many cases the distal end 19 cannot reach region 2 due to instrument collisions with structure 14 or skin 4. The distal end 19 often cannot travel along path 16, and other parts of the instrument generally also cannot travel along path 16.

In some cases, the instrument can be curved into shapes other than the path shape such that with sufficient and skilled manipulation, the distal end 19 can ultimately reach region 2. However, such manipulation may be by trial-and-error, increasing procedural time and in some cases, patient exposure to X-rays or other radiation. Removal of the instrument would normally involve a similar process. Moreover, if the instrument is surrounded by tissue, it cannot as a whole penetrate and glide smoothly through the tissue by leading with distal end 19. Rather, a great deal of lateral movement of the instrument must occur, requiring the relatively broad side of the instrument to penetrate or deform surrounding tissue. This can be both difficult to accomplish (e.g., requiring significant force) and traumatic/damaging to the tissue.

Figure 3:
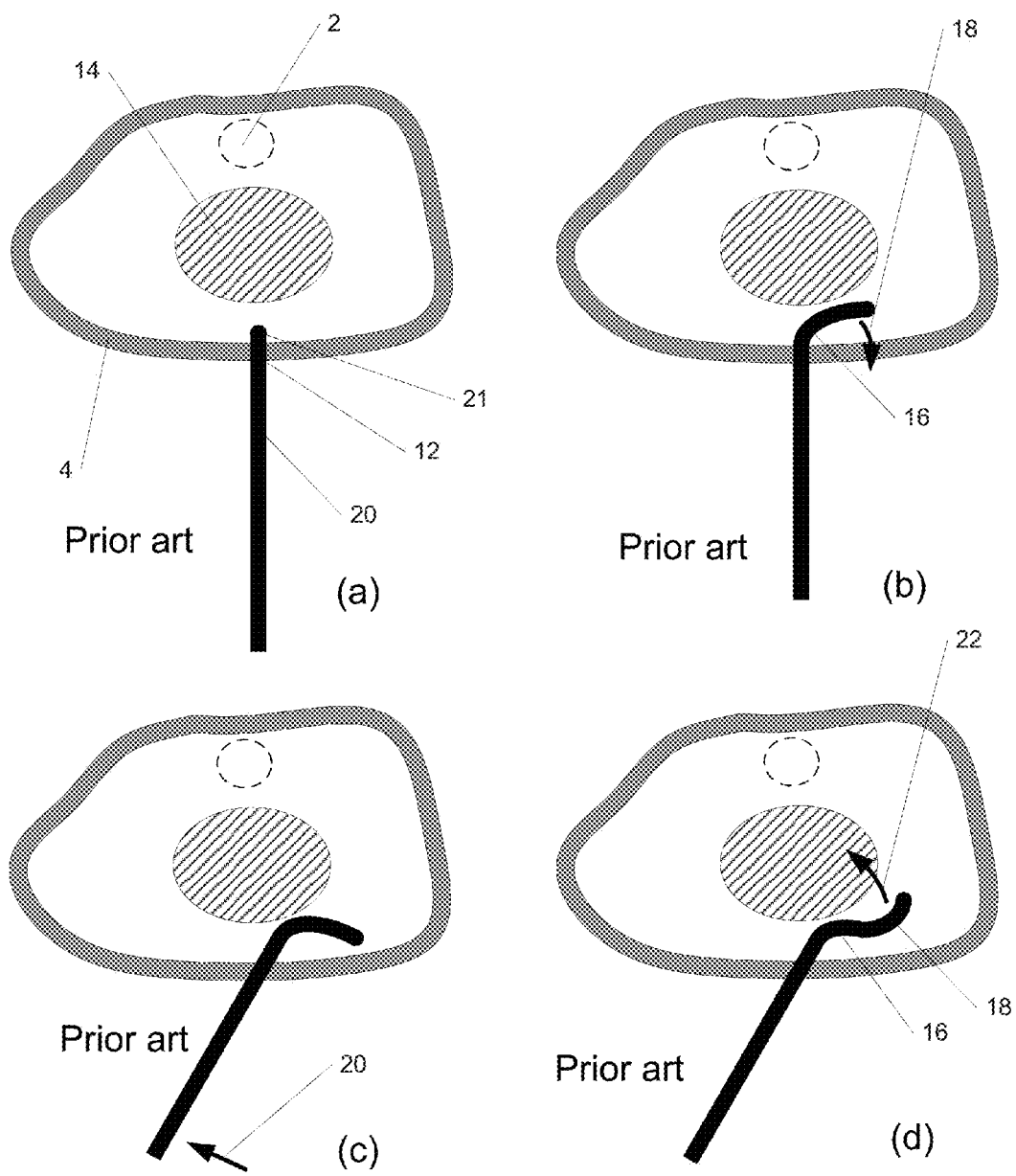
FIGS. 3(a)-(f) depict a target region and the inability of a second prior art device to reach it.
Figure 3:
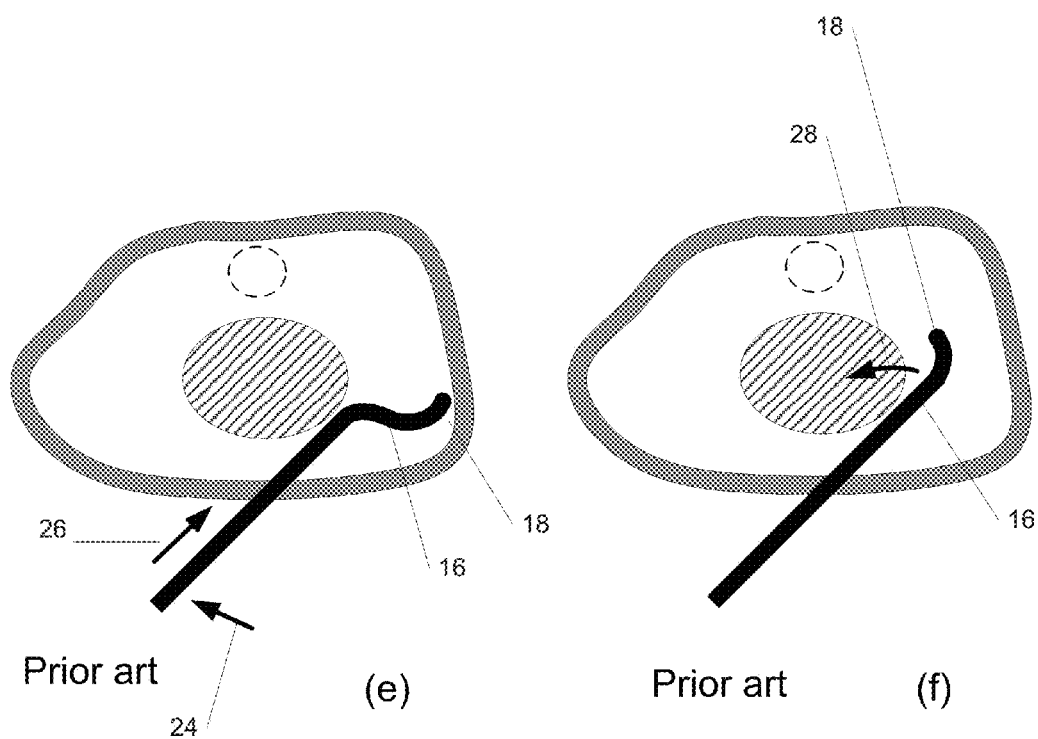

FIG. 3 shows a second method for reaching region 2 with a curved instrument, in which the instrument is provided with the ability to flex and steer under control of the physician. Such an instrument most often is provided with a single steerable section near the distal end 21, but may be provided with additional steerable sections (a total of two such regions are assumed in the figure). A possible sequence of steps aimed at reaching region 2 with distal end 21 is now described. In FIG. 3(*a*), the instrument enters site 12 and in FIG. 3(*b*), the more proximal steerable region 16 is then bent in direction 18. In a later manipulation shown in FIG. 3(*c*), the proximal end of the instrument is moved in direction 20 to the side. In FIG. 3(*d*), the more distal steerable region 18 is then bent in direction 22. In FIG. 3(*e*), the proximal end of the instrument is moved in direction 24 and the instrument is slid in direction 26. Finally, in FIG. 3(*f*), section 16 is straightened out in direction 28. While the distal end 21 may ultimately reach region 2 through a combination of various manipulations of the kind described, it can be a slow, difficult, and iterative process to do so. Moreover, as with the first method, lateral movement of the instrument through tissue can make the required manipulations both difficult and traumatic.

A third method that might be considered for reaching region 2 is the method used, for example, in interventional cardiology. In this method, a guidewire—which can be provided with pre-curved or actively-steerable distal tips—would first be guided and delivered to region 2 and then a flexible instrument such as a catheter would be slid distally over the guidewire. However, since this method requires delivery of guidewire before the instrument is delivered, it is appropriate when the guidewire can itself follow a pre-existing path (e.g., such as within a lumen like an artery) or can be adequately controlled and steered (e.g., magnetically). The method is generally unsuitable for efficiently and accurately accessing region 2 when it is located, as in the figure, within a gas- or liquid-filled cavity or within solid tissue.

1st Embodiment

Figure 4:
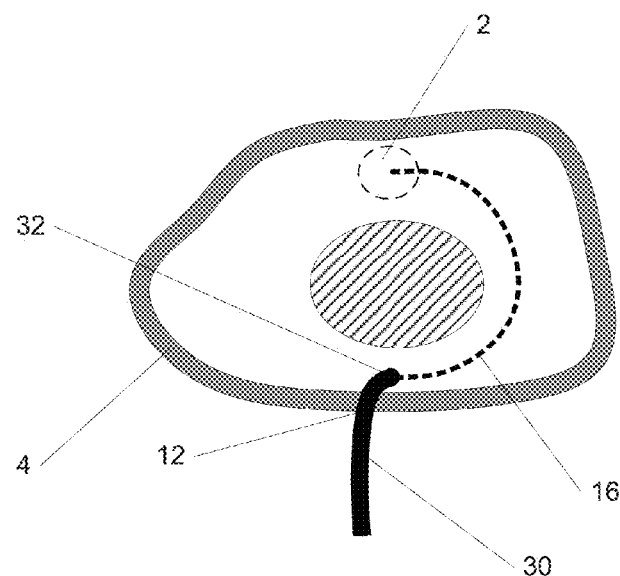
FIGS. 4(a)-(c) depict a target region and illustrates the ability of a distally assembled device to reach it.
Figure 4:
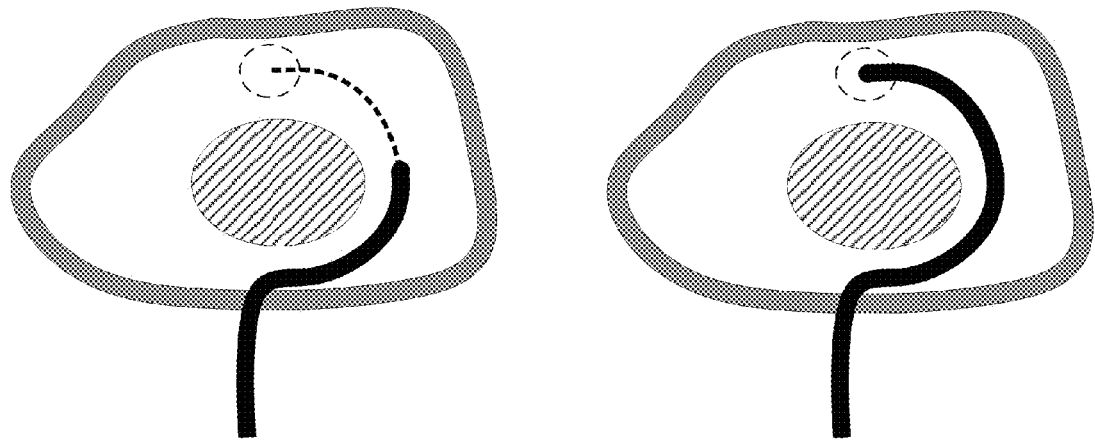

In a 1st embodiment of the invention, an instrument enters the body and is delivered along a desired path such as path 16 of FIG. 2(*a*) as illustrated in FIG. 4(*a-c*) to reach region 2. The path may be determined, for example, using imaging such as CT or MRI. In FIG. 4(*a*), instrument 30 enters the skin 4 through puncture site 12 and begins to follow path 16, curving as it grows or elongates with its distal end 32 in the lead. In FIG. 4(*b*), the instrument has lengthened further and in FIG. 4(*c*) distal end 32 has reached region 2 as desired. Such a "distal growth" behavior allows distal end 32 and the instrument to precisely and quickly follow the path without trial-and-error and with minimal difficulty, force, or potential tissue damage. Moreover, the instrument may be shortened or retracted once used along the same path.

Figure 5:
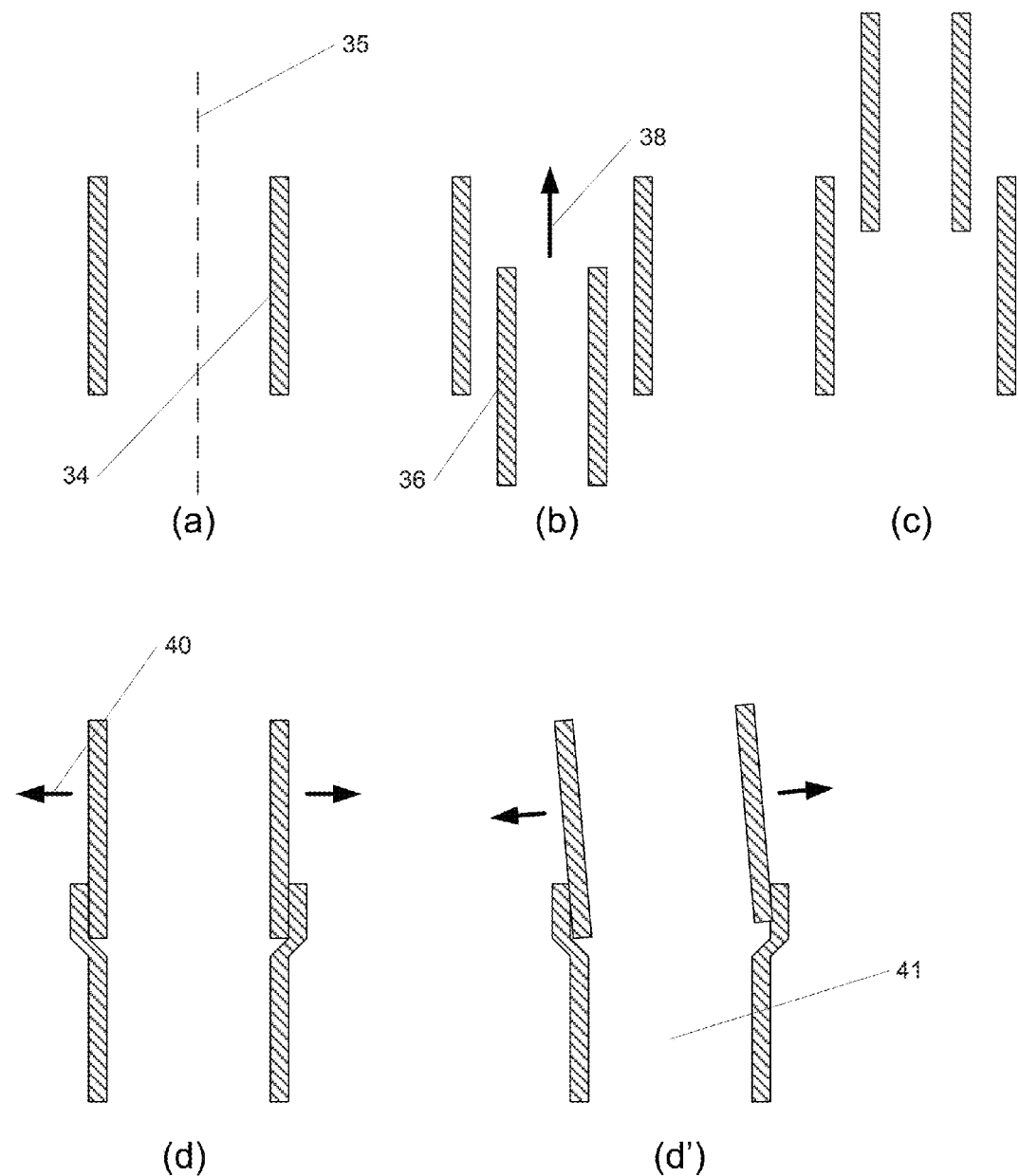
FIG. 5(a)-(d') and FIGS. 6(a)-(f) shows an embodiment of a distally assembled device.

FIG. 5 is a cross-sectional view illustrating how the instrument of the 1st embodiment extends from its distal end, rather than being pushed from its proximal end as with prior-art instruments. New material (or components) required to extend the distal end further along path 16 is supplied to the distal end, e.g., by transportation through the center of the instrument, though in some embodiment variations, material is transported along the exterior of the instrument.

In FIG. 5(*a*), a base tube section 34 is provided, forming the proximal end of the instrument. The geometry shown is rotationally symmetric around axis 35. In FIG. 5(*b*), a radially-collapsed tube section 36 enters section 34 at its proximal end and is moved distally, in direction 38. When section 36 has reached a suitable location along section 34 as in FIG. 5(*c*), it expands in direction 40 as shown in FIG. 5(*d*), in some embodiment variations slightly deforming section 34 as it reaches its final diameter, and interlocking rigidly with section 34. The result is a substantially straight tube, or cannula, comprising two sections, in which the base tube has remained at the same location and a new section—using material supplied at the proximal end—has been joined to the distal end of the cannula. Thus, the distal end is dynamic, not static: a particular section that is the most distal at one time may not be at a later time when another section has extended past it more distally. The most distal portion of the instrument is in some embodiment variations not a section such as section 36, but rather, another component such as a cap. Such a component can begin adjacent to one section and become successively transferred to each new section as the cannula elongates, or can be deployed after the last section has been delivered.

As shown in FIG. 5, in some embodiment variations the instrument is a cannula with a lumen 41 extending along the axis of the instrument through which fluid may be supplied or withdrawn, or through which therapeutic or diagnostic instruments and implants may be passed. In other embodiment variations, the instrument does not have such a lumen once the instrument is fully extended, or in use the lumen may be mostly obscured (e.g., by a stylet or distal tip). Therapeutic and diagnostic devices may also be slid over the exterior of the deployed DASC device, rather than through it, or may use DASC as a rail along which the device is advanced and/or retracted.

For use in a gas or liquid environment, the instrument needs to be relatively rigid, so each section preferably forms a rigid, well-interlocked joint with its neighboring section. Rigid interlocking may be achieved by friction; protrusions on one section interacting with features such as protrusions, cavities, or perforations on another; by textures, or by other suitable means. In the case of a permanent cannula, sections may be attached by adhesive, welding, brazing, soldering, riveting, and other methods known to the art.

The expansion of section 36 can be accomplished by a variety of means. In some embodiment variations, it is the result of the section springing back to its natural diameter after having been compressed. In other embodiment variations it is the result of a deformation that plastically deforms the material of section 36 outwards (e.g., section 36 may be designed similar to a metal stent known to the art), after allowing for elastic springback/recoil. For example, an expanding balloon or bladder may be used to deform the section to an approximately circular shape. In still other embodiment variations, it is the result of section 36 being elastically deformed outwards and held in its expanded position (e.g., by a ratcheting mechanism or clips; or if, for example, designed as a braided superelastic nickel-titanium tube, by maintaining axial tension). In FIG. 5(*d*), section 36 has been joined to section 34 at an angle, forming a short section of a curved cannula instead. By adding additional sections similar to section 36—though not necessarily of the same length, diameter, or material—at the desired relative angles, a long, distally-assembled cannula following a complex 3-D path may be constructed.

Figure 6:
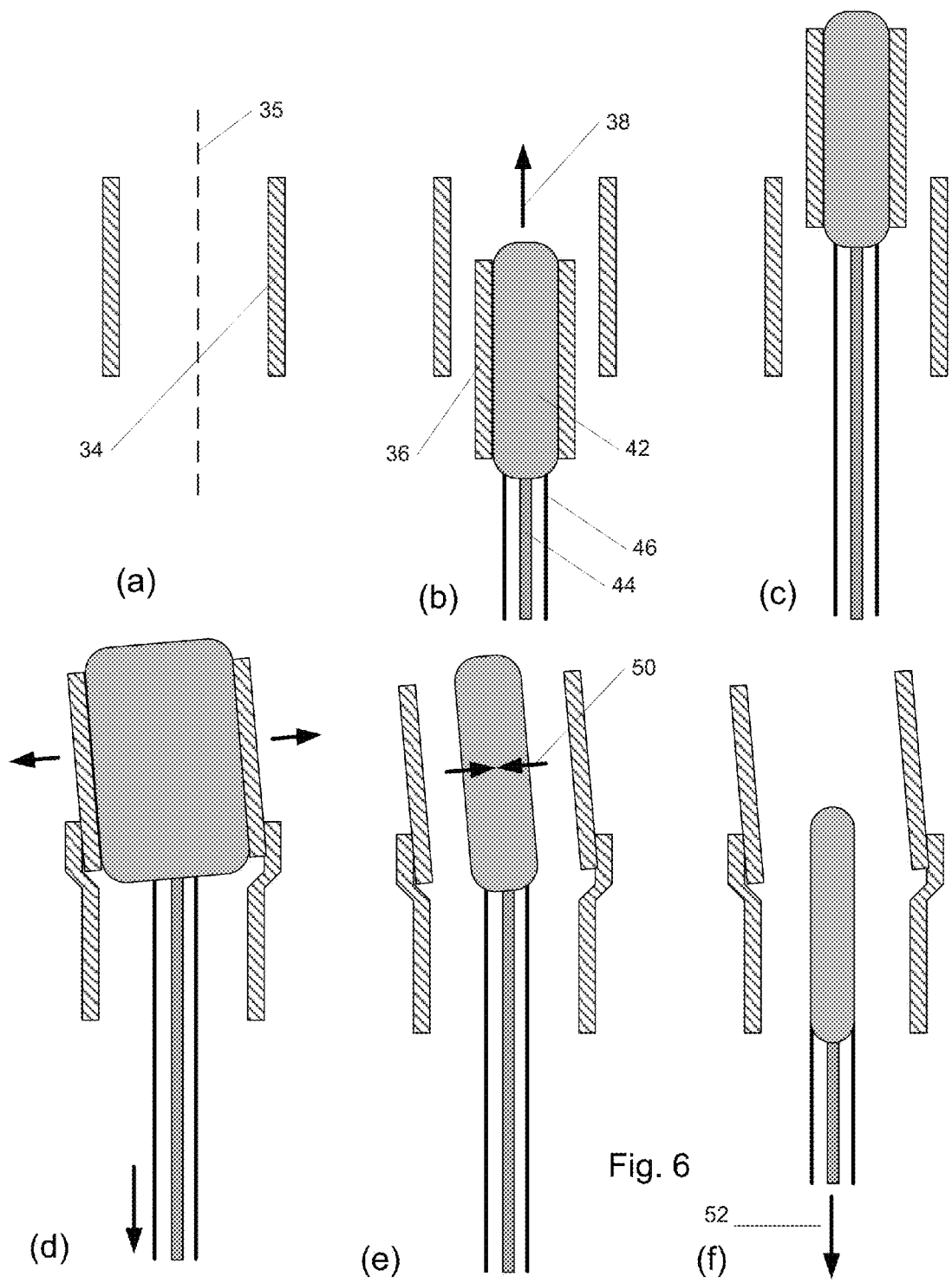

FIG. 6 depicts how the steps in FIG. 5 may be accomplished in some embodiment variations in which the diameter of section 36 is normally small and must be actively deformed outwards to achieve a larger diameter. In FIG. 6(*b*), section 36 fits over balloon 42 and moves along with it (e.g., section 36 is snugly fitted over balloon 42, which in some embodiment variations is slightly inflated). Balloon 42 is supported by flexible hollow shaft 44 and connected to wires 46. To allow balloon 42 to tilt in any direction, thus allowing the instrument to follow a 3-D path, at least two wires 46 may be provided. However, in some embodiment variations, means other than wires are used to tilt balloon 42, or wires may be contained within shaft 44. Balloon 42 is advanced distally through section 34 in direction 38. Once section 36 has reached a suitable location along section 34 as in FIG. 6(*c*), balloon 42 is tilted (if applicable) by pulling on at least one wire 48 in direction 49, and is inflated to expand section 36 in direction 40 as shown in FIG. 6(*d*), interlocking sections 36 and 34. In practice, the expansion or tilting can be initiated prior to section 36 reaching its correct distal position. Having expanded section 36 to interlock with section 34, in FIG. 6(*e*) balloon 42 detaches from section 36 and collapses in direction 50. In FIG. 6(*f*) balloon 42, now in some embodiment variations fully collapsed, retracts distally in direction 52, where it can fit inside an additional section, expand slightly to secure it, and then repeat a process similar to that of FIG. 6(*b-f*) to build a long cannula.

In embodiment variations in which sections are naturally of larger diameter and spring back after having been compressed, means of keeping the sections compressed until they are delivered to the distal end of the cannula may be used. For example, a balloon may be provided with hooks on its surface that engage features on the inside surfaces of section such as section 36. Once so engaged, by collapsing the balloon or allowing it to collapse, section 36 is forced to become compressed so it can fit through other sections. In some embodiment variations, sections such as section 36 may comprise an elastic tube, for example, a braided wire tube designed to reduce in diameter when elongated axially, and increase in diameter when compressed axially, or an elastomeric tube. In the case of sections, which are normally expanded (i.e., having a larger diameter when no forces act on them), they may be delivered through other sections by temporarily stretching them axially, and interlocking them to other sections by releasing the axial tension.

In some embodiment variations, the cannula can be disassembled and retracted (e.g., after completion of a clinical procedure) by approximately reversing the steps shown in FIG. 6, e.g., with the most distal section disassembled and retracted first. In such a process, various means of compressing the sections to a diameter small enough to pass proximally through other sections may be used, including the hooked balloon already described. In the case of sections composed of elastomeric material or wire braid, for example, these can be reduced in diameter by stretching them axially, and then retracting them through other sections. In the case of a ratcheting mechanism that holes the sections open, the ratchet for each section would be released to allow disassembly.

In some embodiment variations, sections transported distally are enlarged further than shown in FIGS. 5-6 so as to fit over and interlock with the exterior surface of other sections, in lieu of fitting over and interlocking with the interior surface as already described. In the case of sections that are elastically stretched to a larger diameter, interlocking of a newly-added section to another section may be achieved or enhanced by means of the newly-added section simply collapsing onto the other section.

The steps shown in FIGS. 5-6 may be, in some embodiment variations, performed manually by a physician or other personnel, or in other embodiment variations may be performed automatically or semi-automatically, making the instrument a robotic system. Such a system can for example manipulate using computer-controlled motors and actuators the position of shaft 44, the tension on wires 46, and the pressure of balloon 42 in FIG. 6, such that the cannula is extended along a path or retracted. Such control may be based on a predetermined path within the patient's body, or under real-time control of the physician, e.g., using a joystick to steer the cannula as it lengthens.

Figure 7:
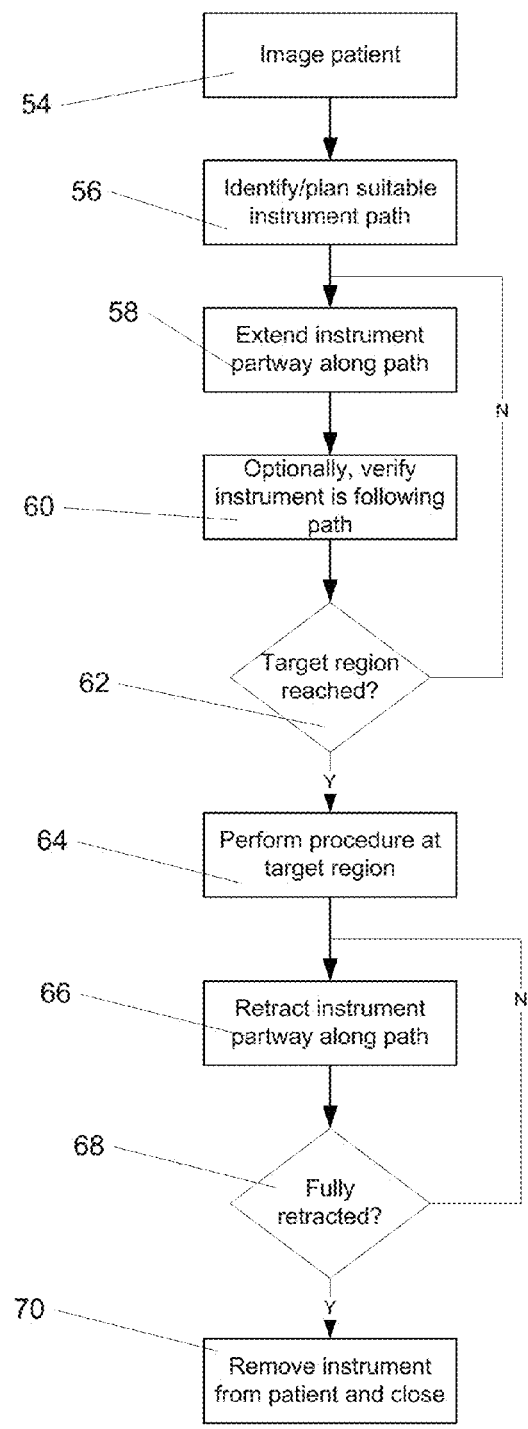
FIG. 7 is a flow chart describing how a distally assembled device may be used in some embodiments.

FIG. 7 is a flow chart describing how a device such as that described herein may be used in some embodiments. Referring to the flowchart symbols of FIG. 7, imaging (54) may be performed on the patient prior to the procedure, using modalities such as CT, MRI, and ultrasound, and the image data aligned to the patient, e.g., using fiducial marks known to the art. In some embodiment variations, imaging is performed while the instrument is advanced as well, or in lieu of performing it beforehand. A suitable path along which the instrument is to be delivered is then identified/planned (56) and the instrument is extended partway (e.g., one section at a time) along the path (58). Optionally, verification that the instrument is adequately following the commanded path may be performed (60), and adjustments made (e.g., to the angle of the next section to be added). A decision (62) is then made whether the target region is reached. If not, then the instrument is extended further. If it has, then the procedure (e.g., delivery of drug, biopsy, ablation, etc.) is performed at the target region (64). The instrument then is retracted partway (e.g., one section at a time) along the path (66). A decision (68) is then made whether the instrument is fully retracted and able to be removed from the patient. If not, then the instrument is retracted further. If it has, the instrument is removed and the puncture/incision is closed.

2nd Embodiment

Figure 8:
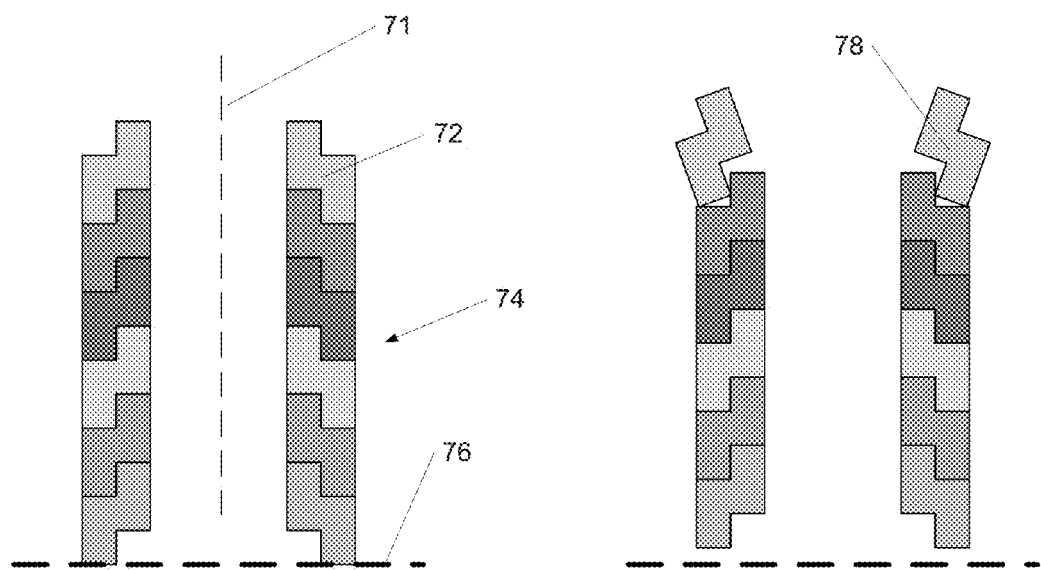
FIGS. 8(a)-(g) show an embodiment of a distally assembled device.
Figure 8:
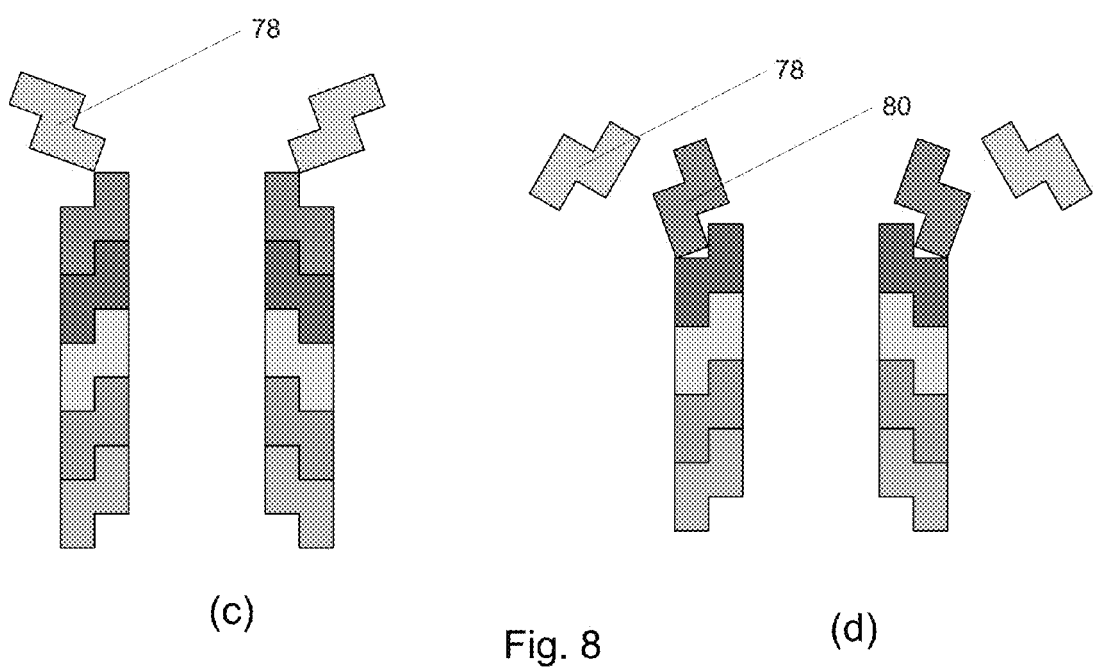
Figure 8:
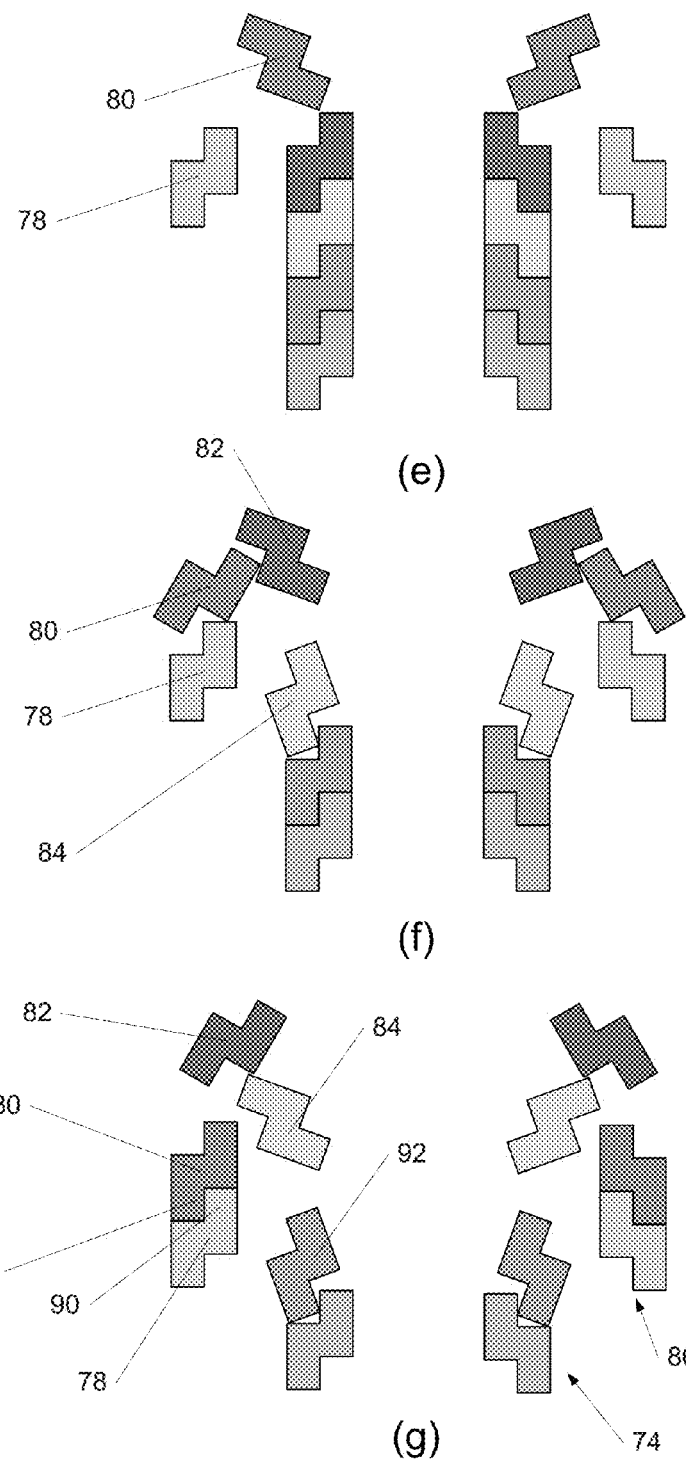

FIG. 8 depicts a cross-sectional view of a 2nd embodiment of the invention similar in some aspects to the 1st embodiment. The geometry shown is rotationally symmetric around axis 71. In this 2nd embodiment, in lieu of tubular sections as in the 1st embodiment, rings 72 are provided as shown in FIG. 8(*a*) which can fit into one another due to their shape, and which are capable of stretching to a larger diameter and everting. The ability to stretch, in some embodiment variations, may be provided by segmenting the ring in the plane of the ring (e.g., into pie-like slices) and joining these together with compliant elements such as flexures, which may be integral to the ring. As a whole, the rings stack and nest to form tube 74. Initially the proximal end of tube 74 is aligned to reference plane 76. In FIG. 8(*b*), tube 74 has moved distally and distal ring 78 has begun to evert and stretch. In FIG. 8(*c*) and all remaining sub-figures within FIG. 8, tube 74 has moved further distally. Also, ring 78 has continued to evert and stretch while tube 74 has moved further proximally. In FIG. 8(*d*), ring 78 is mostly everted and stretched while ring 80 is beginning to evert and stretch. In FIG. 8(*e*), ring 78 has completely everted and stretched, forming the first and most proximal ring of a new, larger-diameter, outer tube. Meanwhile, ring 80 has everted and stretched further. In FIG. 8(*f*), ring 80 has nearly completely everted and stretched and is beginning to nest against ring 78. Meanwhile, ring 82 has partially everted and stretched and ring 84 is beginning to evert and stretch. In FIG. 8(*g*), ring 80 has completely everted and nested against ring 78, forming the second ring of outer tube 86. Stretched as it is in this position, the lower portion 88 of ring 80 presses against the upper portion 90 of ring 78, clamping ring 80 to ring 78 securely. As shown, rings 80 and 78 are parallel to one another, forming a straight section of outer tube 86. However, ring 80 may also be at an angle when it clamps onto ring 78, causing outer tube 86 to be curved. Also shown in FIG. 8(*g*) are other rings such as 82, 84, and 92 in different stages of stretching and everting. The overall result is that the inner tube 74 moves distally to supply rings to outer tube 86, extending the cannula towards the target region of the patient's body. In one variation, eversion and stretching of the rings is due to them being affixed to an elastomeric tube (not shown) which is itself everted and stretched to form an inner wall (associated with the inner tube) and an outer wall (associated with the outer tube). The stretching and eversion of the elastomeric tube may be caused simply by pushing the inner wall of the tube distally. In this variation or in some other variations, the rings and/or the tube are temporarily attached to wires (not shown) which, if differentially tensioned, cause rings to clamp onto one another in a non-parallel, angled manner, curving the resulting structure in that region.

The steps shown in FIG. 8 may be, in some embodiment variations, performed manually by a physician or other personnel, or in other embodiment variations may be performed automatically or semi-automatically, making the instrument a robotic system.

3rd Embodiment

Figure 9:
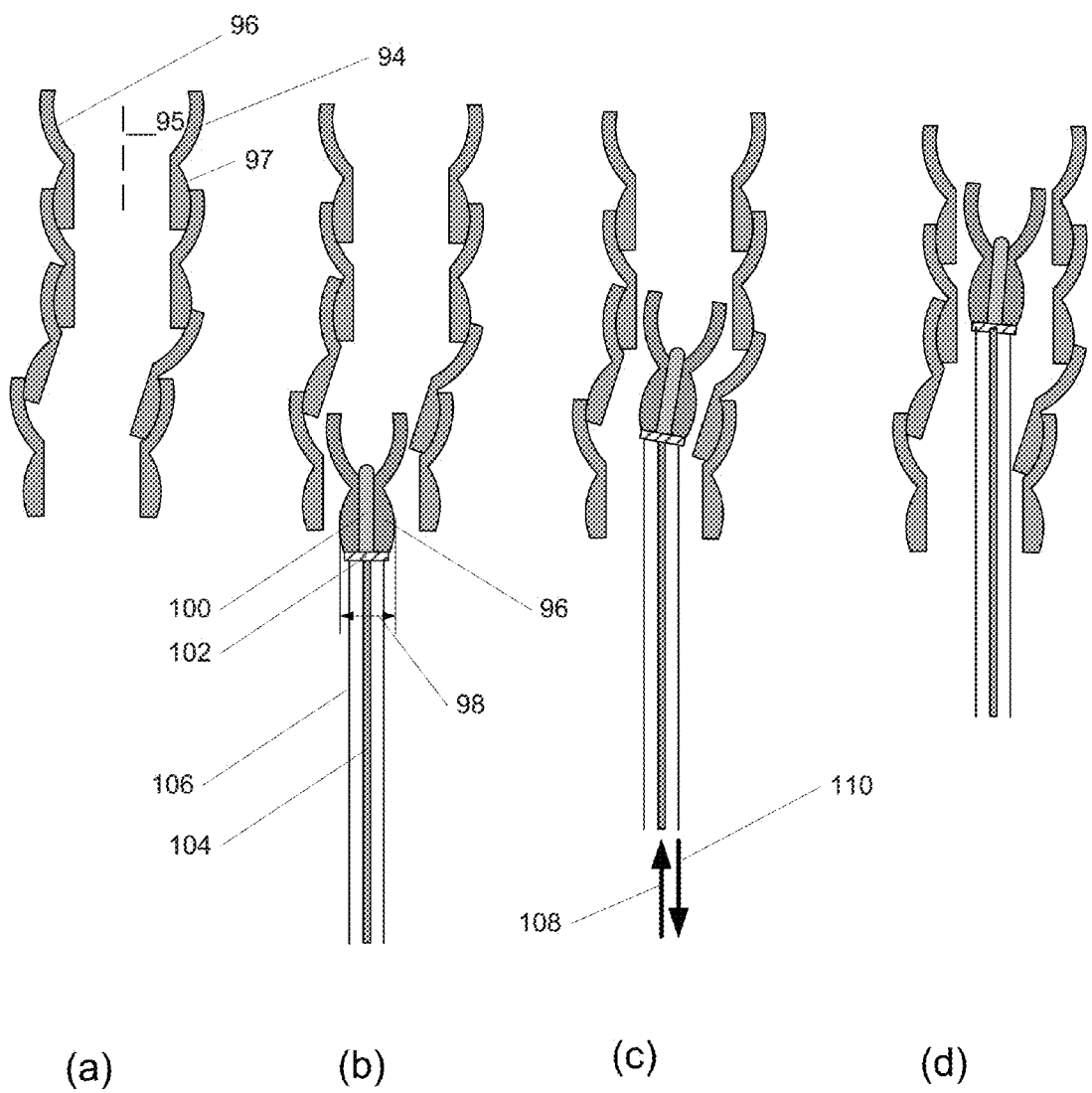
FIGS. 9(a)-(h) show an embodiment of a distally assembled device.
Figure 9:
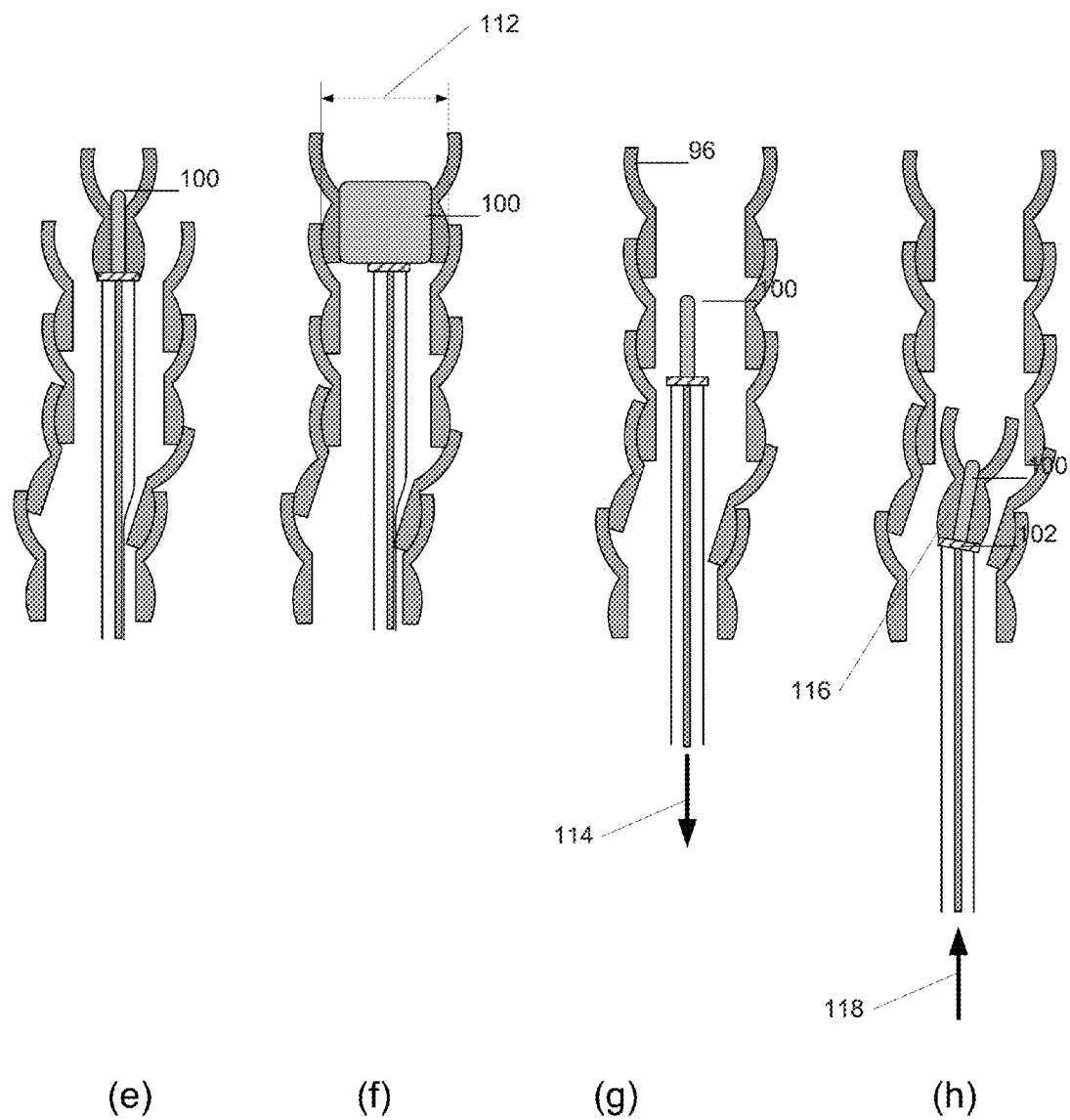

FIG. 9 is a cross-sectional view of a 3rd embodiment of the invention similar in some aspects to the 1st embodiment. In this 3rd embodiment, the sections that are assembled at the distal end include surfaces which are sections of a sphere, to facilitate sections interlocking with one another at multiple angles through ball joint-like structures. FIG. 9(*a*) shows an instrument comprising four sections interlocked at various angles, the most distal of which is section 94. The geometry shown of section 94 and other sections is rotationally symmetric around axis 95. Sections such as section 94 may have a spherical interior surface 96 and a spherical exterior surface 97. The particular shape of the overall instrument is provided as an example only. In FIG. 9(*b*), section 96, initially collapsed to a relatively small OD (outside diameter) 98 is supported by balloon 100 attached to base 102 and flexible hollow shaft 104. Wires 106 are attached to base 102 (or balloon 100) to control the angle of balloon 100 and section 96. In FIG. 9(*b*), section 96 has entered the most proximal section and begins to move distally. In FIG. 9(*c-d*) it continues to move distally, being pushed by shaft 104 in direction 108 through the lumen formed by the already-interlocked sections. If required to minimize collisions with such sections, wires 106 may be pulled 110 relative to shaft 104 to steer section 96 through the lumen. When balloon 100 is tilted as shown, shaft 104 doesn't necessarily bend near its top or base 102 apparently swivel as shown; rather, shaft 104 may bend more gradually along its length.

In FIG. 9*e*, section 96 has reached its destination and is ready to expand. In FIG. 9(*f*) balloon 100 has expanded, significantly increasing the OD 112 of section 96. The ratio between OD 112 after expansion and OD 98 prior to expansion can be significant (e.g., 1.5-5). To allow a change in diameter of sections, in some embodiment variations sections may be segmented (e.g., into pie-like slices) and joined together with compliant elements such as flexures, which may be integral to the segment.

Before section 96 has expanded completely and interlocked with section 94, it is tilted in the desired direction by pulling on at least one of the wires 106. Tension on wires 106 may be removed when not needed, as is the case with one of wires 106 after full expansion of balloon 100 in FIG. 9(*e*). In FIG. 9(*g*), balloon 100 has deflated, released section 96, and is moving proximally in direction 114 in preparation for supporting and transporting another section. Section 96 remains expanded and interlocked with section 96 by various means discussed already with respect to the 1st Embodiment: plastic deformation allowing for elastic springback, a ratcheting mechanism, etc.

FIG. 9(*h*) shows balloon 100 supporting section 116 and transporting it distally in direction 118, repeating the cycle begun in FIG. 9(*b*). In one variation, base 102 is omitted, for example, so that balloon 100 can pass in a proximal direction through section 116, and then expand slightly to secure it before progressing distally again.

In this variation and in some other variations, the edges of sections are more rounded, chamfered, or tapered than shown in FIG. 9, minimizing the likelihood of getting caught on other sections when moving in either direction.

Once the distal assembly process has been completed to access the target region and the clinical procedure has been completed, disassembly of the instrument can be achieved by approximately reversing the assembly sequence, using the balloon and its associated components to remove and retract each section, beginning with the most distal section.

The steps shown in FIGS. 9(*a*)-(*h*) may be, in one variation, performed manually by a physician or other personnel, or in other embodiment variations may be performed automatically or semi-automatically, making the instrument a robotic system.

4th Embodiment

Figure 10:
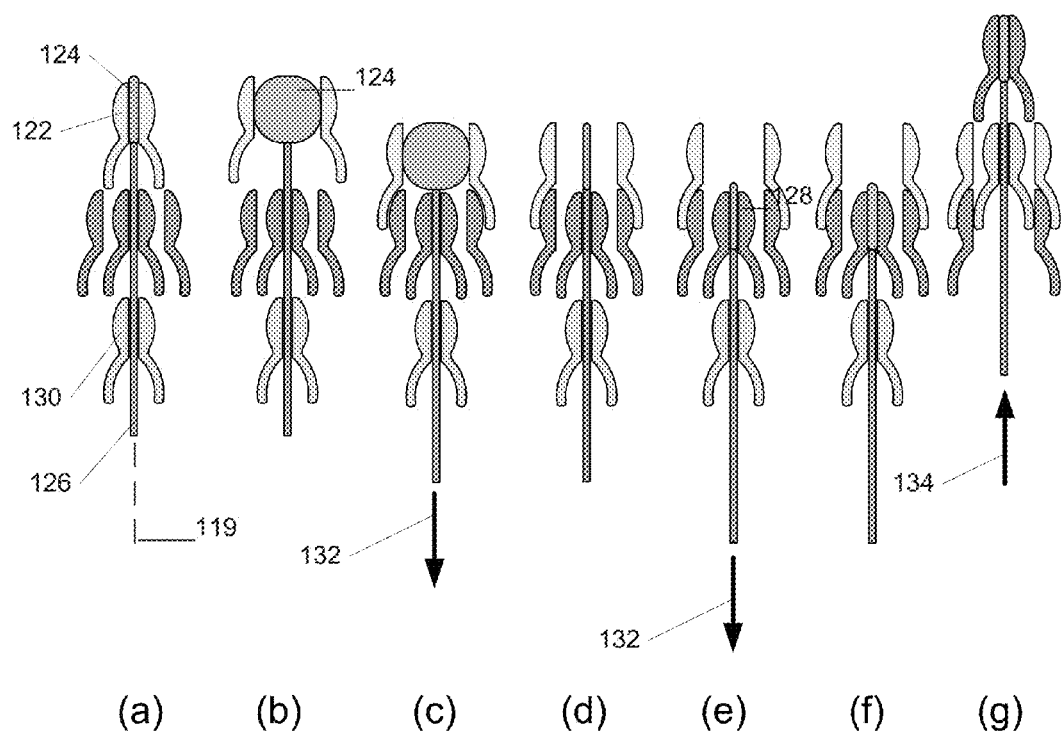
FIGS. 10(a)-(g) show an embodiment of a distally assembled device.

FIG. 10 is a cross-sectional view of a 4th embodiment of the invention similar in some aspects to the 1st, 2nd, and 3rd embodiments. The geometry shown is rotationally symmetric around axis 119. In this 4th embodiment, the sections that are assembled at the distal end include surfaces which are sections of a sphere as in the 3rd embodiment. As with the 2nd embodiment, a given segment engages an external surface of the next most proximal segment, instead of an internal surface as with the 1st and 3rd embodiments. Unlike the 2nd embodiment, there is no eversion of the elements. To allow a change in diameter of sections, in some embodiment variations sections may be segmented as already described. In FIG. 10, the instrument is shown straight (all sections aligned in parallel) and not curved for simplicity.

FIG. 10(a) shows an instrument comprising an initially-expanded base section 120 and expandable sections such as distal section 122 supported by balloon 124 and flexible hollow shaft 126. Shaft 126 passes through section 120 and also passes through other sections such as sections 128 and 130. In some embodiment variations, wires connecting to balloon 124 are provided to tilt the axis of sections as they are delivered.

In FIG. 10(b), balloon 124 has expanded enough to expand the diameter of section 122 so its proximal concave spherical surface can be fit over the distal convex spherical surface of section 120. In FIG. 10(c), balloon 124 has been retracted proximally in direction 132 such that the two spherical surfaces are in proximity and in FIG. 10(d), balloon 124 has deflated, allowing section 122 to clamp securely and interlock with section 120. In FIG. 10(e), balloon 124 has been further retracted in direction 132 such that it can enter the lumen of section 128. In FIG. 10(f), balloon 124 has slightly inflated, allowing it to pull section 128 as shown in FIG. 10(g) distally in direction 134. The configuration shown in FIG. 10(g) is equivalent to that of FIG. 10(a): one cycle of distal assembly has been achieved, and is about to repeat again.

As before, disassembly of the instrument can be achieved by approximately reversing the assembly sequence beginning with the most distal section. The steps shown in FIG. 10 may be, in some embodiment variations, performed manually, or in other embodiment variations, performed automatically or semi-automatically.

5th Embodiment

Figure 11:
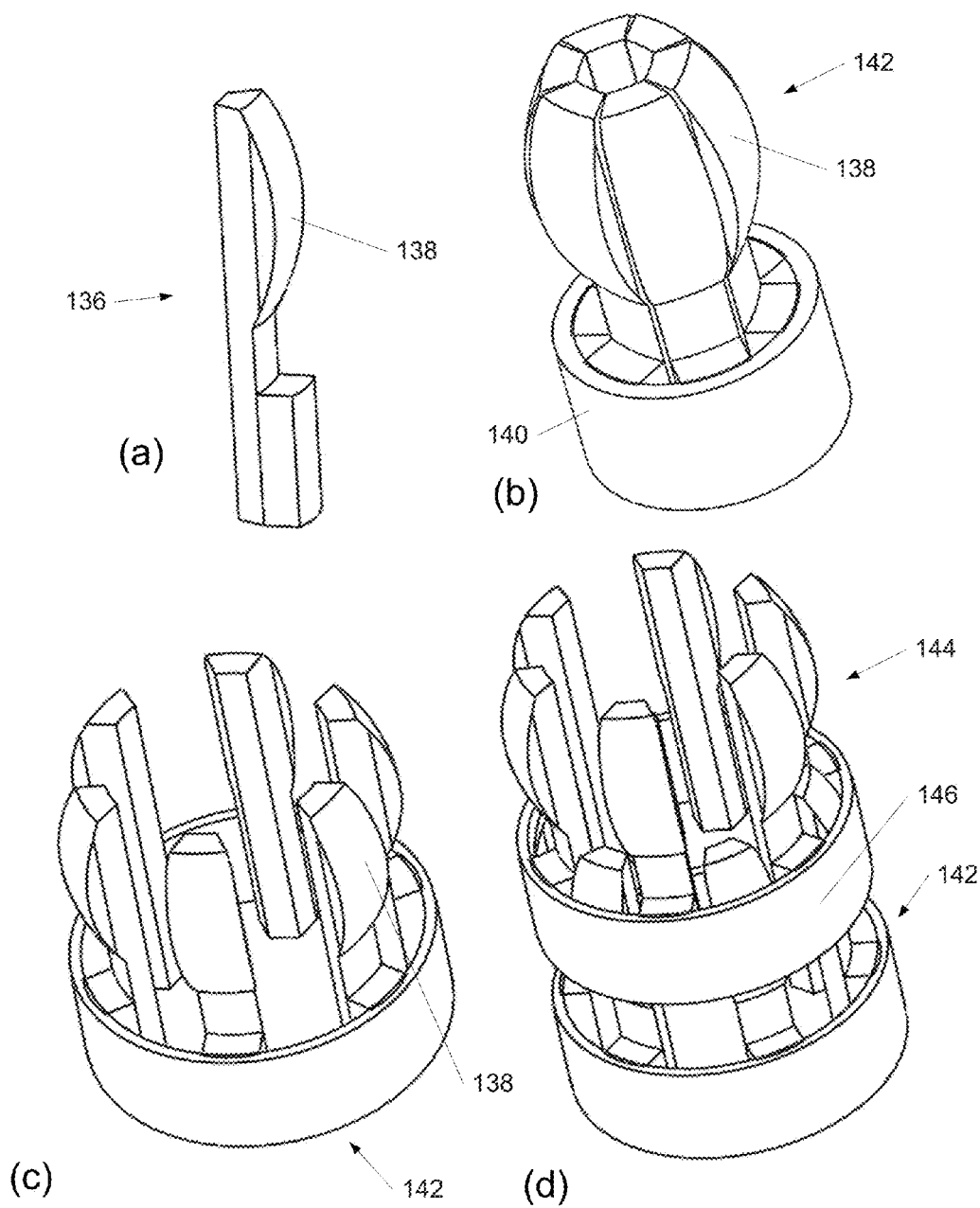
FIGS. 11(a)-(d) show an embodiment of a distally assembled device.

FIG. 11 is an isometric view of a 5th embodiment of the invention similar in some aspects to previous embodiments and in particular, the 4th embodiment. Each section in the 5th embodiment is comprised of pie-like segments 136 as in FIG. 11(a). Each segment in some embodiment variations has a distal surface 138 that is a section of a sphere. Multiple (e.g., 6) segments are joined to a stretchable (e.g., elastomer) band 138 as shown in FIG. 11(b), forming a section 142.

In the configuration shown in FIG. 11(b), the section has a relatively small OD. However, by stretching band 138, section 142 can expand considerably as in FIG. 11(c). As shown in FIG. 11(d), once band 140 is expanded, another section 144 initially in a compressed configuration (similar to that shown in FIG. 11(b)) can pass distally through section 142, then expand its OD, and then move in a proximal direction such that the proximal ends of segments in section 144 can fit in between the segments of section 142 as shown in FIG. 11(d). At that time, band 146 of section 144 can also make contact with surfaces 138 of section 142.

In some embodiment variations, friction between band 146 and surfaces 138 of section 142 can join sections 142 and 144 together with sufficient stiffness. In other embodiment variations, other means of interlocking are used. In some embodiment variations, after all sections are distally assembled into an instrument, the OD of the most proximal section (which has been maintained by a suitable mechanism) is reduced, causing the ODs of all the more distal segments to also be reduced. As the OD of a section is reduced, the proximal ends of a given segment come into contact with the distal ends of the section just proximal to it. Such contact, as the segments clamp one another, leads to additional friction and in some embodiment variations other interlocking features may be provided. For example, protrusions on the sides of the proximal ends of segments in section 144 may fit into holes on the facing surfaces: the distal end of segments from a section 142. Interlocking mechanisms such as this preferably are designed to allow for positive interlocking regardless of the relative orientation of neighboring sections.

6th Embodiment

Figure 12:
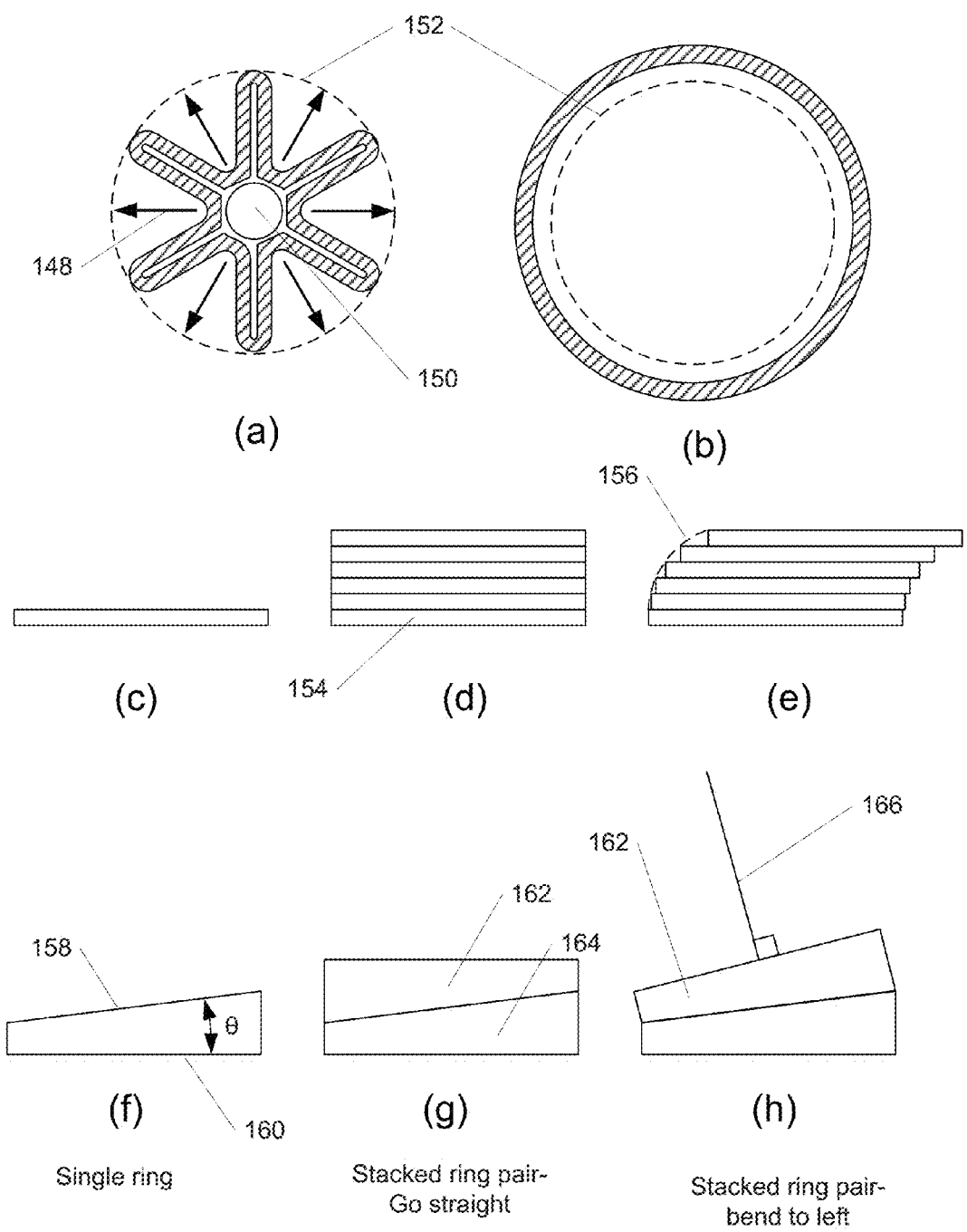
FIGS. 12-15 depict an embodiment of a distally assembled device.

FIG. 12 shows a 6th embodiment of the invention similar in some aspects to previous embodiments. In the 6th embodiment, the instrument is distally assembled from a set of rings (e.g., circular or polygonal) made from a deformable material (e.g., a metal). FIG. 12(a-b) show plan views of rings. A ring initially unexpanded/compressed into a small OD 152 as in FIG. 12(a) can expand as shown in FIG. 12(b), e.g., through the use of balloon 150, to form a ring with an ID (internal diameter) larger than OD 152. This allows another ring in compressed form to pass through it in a distal direction; in some embodiment variations rings can be transported through other rings while supported by the balloon, similar to other embodiments already discussed.

FIG. 12(c) shows an elevation view of a single expanded ring in some embodiment variations, and FIG. 12(d-e) show elevation views of multiple rings in the same embodiment variation. In FIG. 12(d), rings have been stacked, beginning with proximal ring 154, with no offset between them, forming a straight cannula. In contrast, in FIG. 12(e), rings have been stacked with offsets to follow curve 156. With a large enough number of rings (which may be thicker than shown in the figures) and appropriate offsetting (not so much as to make the lumen through the ring stack smaller than is needed to pass a collapsed ring), a long cannula may be distally assembled to follow a complex 3-D path.

FIG. 12(f) shows an elevation view of a single expanded ring in some embodiment variations, and FIG. 12(g-h) show elevation views of two rings in the same embodiment variation. In this embodiment variation, the top surface 158 and bottom surface 160 are not parallel, giving the ring a wedge shape with a wedge angle theta between the surfaces. Such rings may be paired as in FIG. 12(g-h). When paired and relatively oriented such that the thinnest section of distal ring 162 overlies the thickest region of ring 164, the top and bottom surfaces of the ring pair are parallel. Distally assembling a cannula from a set of paired rings arranged as in FIG. 12(g) would yield a straight cannula. In contrast, as shown in FIG. 12(h), by rotating ring 162 relative to ring 164, the top and bottom surfaces become non-parallel. Distally assembling a cannula from a set of paired rings arranged as in FIG. 12(h) would yield a curved cannula. The amount of relative rotation of two rings in a pair determines the amount of non-parallelism of the ring pair, and the amount of local curvature of the cannula. Meanwhile, the direction of the normal to the top surface 166 determines the direction of the local curvature of the cannula. Unlike the offset stacked rings of FIG. 12(c-e), the lumen through a cannula made from wedge-shaped rings is not reduced by offsetting. Wedge-shaped segments refer to the mating faces of the segments. The non-parallelism of the proximal mating face with respect to the distal mating face on the same segment allows the apparatus to assume a curved shape, and the orientation of the wedge with respect to the next most proximal segment determines the amount of curvature and its direction.

To form a rigid cannula, rings should not move relative to their neighbors. Among the methods available to prevent such movement are interlocking protrusions on, for example, the bottom of odd-numbered rings, which fit into other protrusions, cavities, or perforations on, for example, the top of even-numbered rings. For example, radially-arranged gear-like teeth on both the upper and lower surfaces of rings can engage one another in one of many discrete orientations. FIG.

Figure 13:
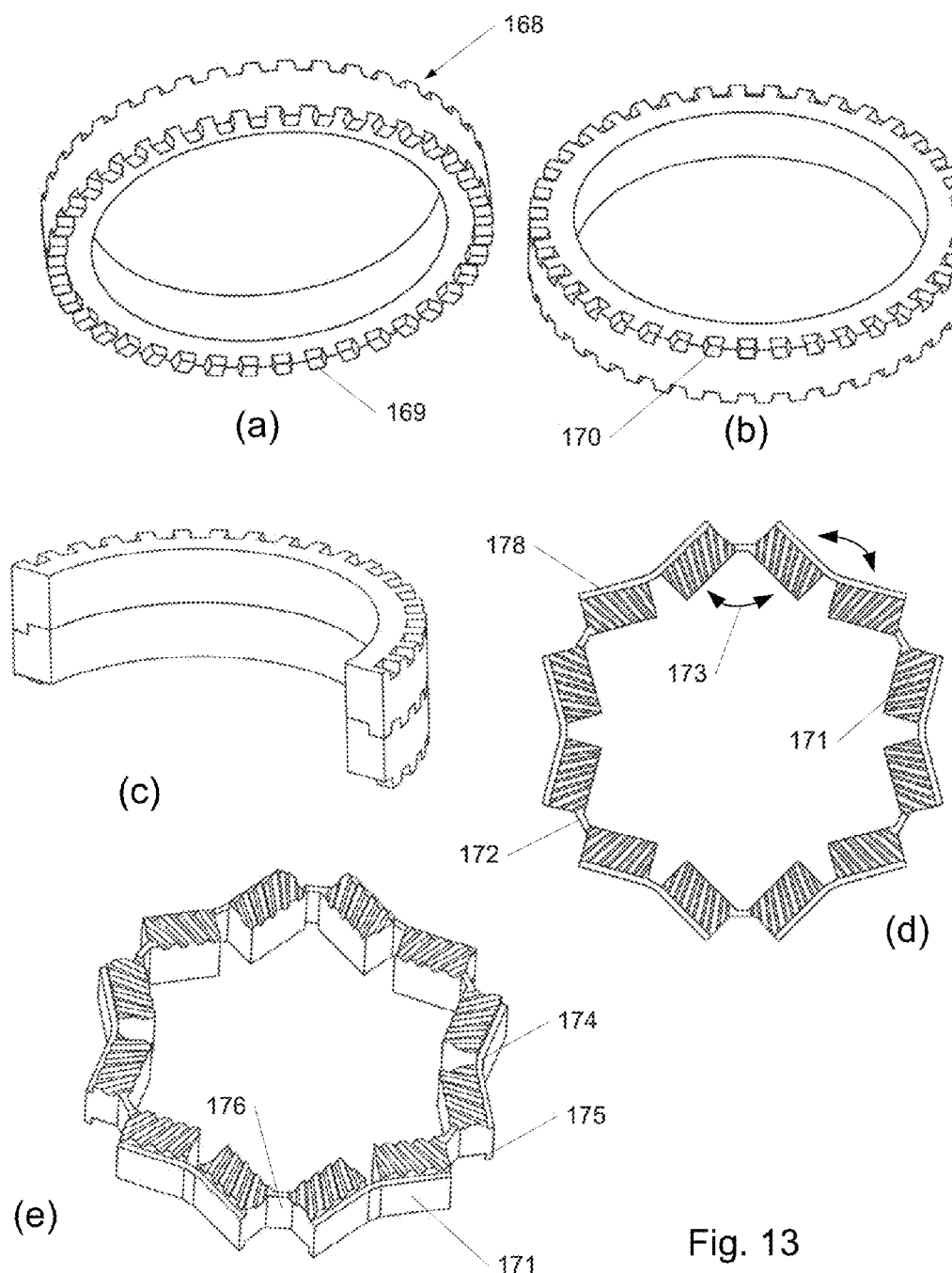
Figure 13:
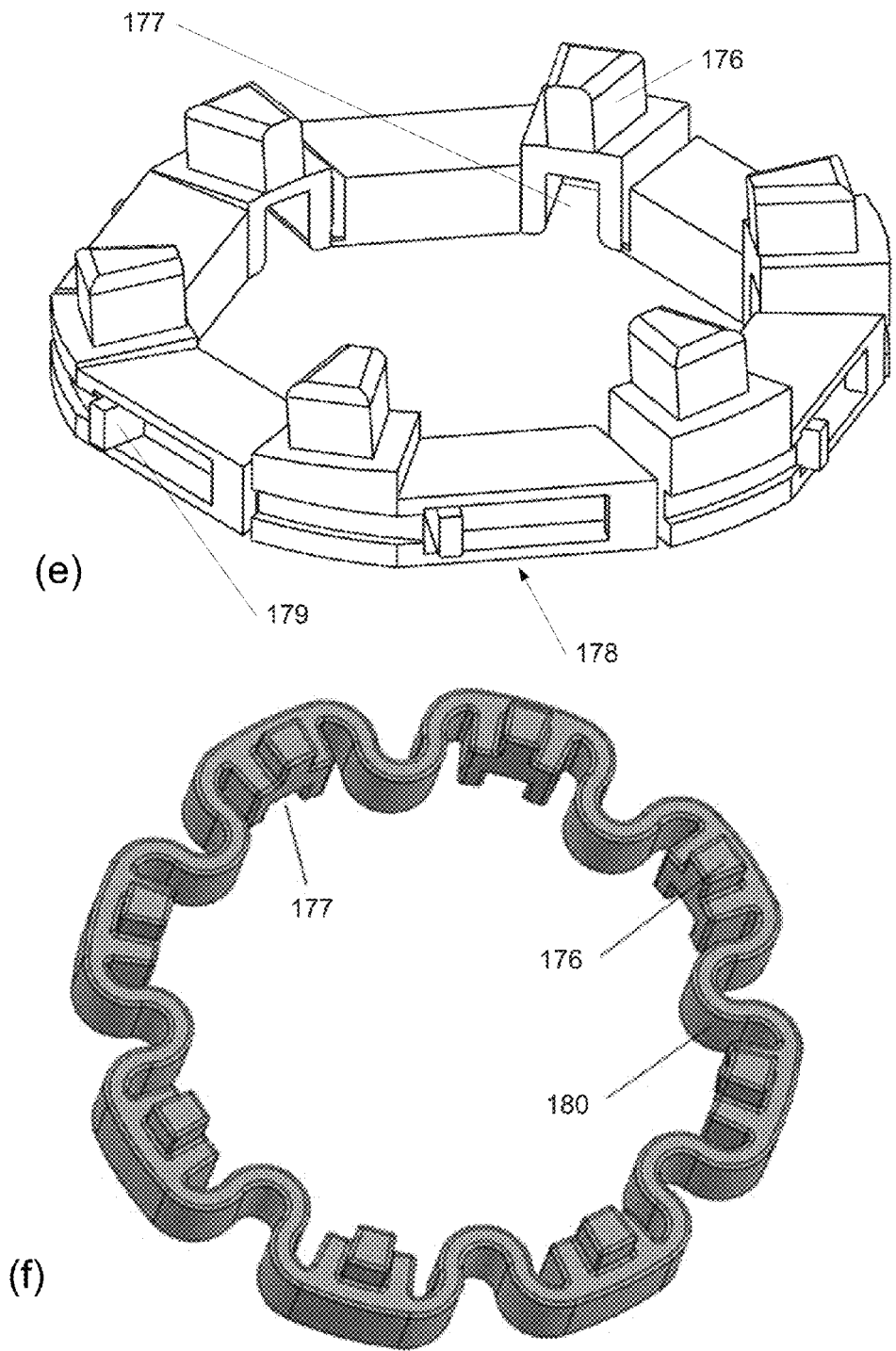

13(*a-b*) show, respectively, bottom and top isometric views of an expanded ring with gear-like teeth 169 along the bottom edge and recesses 170 to accommodate those teeth along the top edge. FIG. 13(*c*) shows a cross-sectional view of two such rings stacked such that the teeth of the upper ring fit into the recesses in to lower one. As shown, the rings are interlocked as long as some axial tension or preload is provided to keep the rings from separating: one cannot rotate with respect to the other, nor can one slide radially with respect to the other, since the teeth recesses for the teeth are only near the edge. It is intended that the rings in FIG. 13(*a-c*) combine in pairs like the rings in FIG. 12(*f-h*) and be wedge-shaped in elevation view as shown in those figures; this taper is not shown in FIG. 13(*a-c*).

Also not shown in FIG. 13(*a-c*) is evidence of the rings having initially been compressed so as to pass through the center of other rings. FIG. 13(*d-e*) show a segmented ring comprising relatively rigid segments 171 and relatively flexible hinges 172, which illustrates, as with FIG. 12(*a*), how a ring can initially be compressed and then open up as shown by arrows such as arrow 173 into a shape similar to that of FIG. 13(*d-e*), or even be further expanded to become more circular. As with the rings of FIG. 13(*a-c*), these rings can have teeth along the outer edges of the bottom surface, and recesses along the outer edges of the top surface, preventing relative rotation of rings when stacked. In the variation shown, the teeth are towards the inner edges on top and bottom, and a groove 174 is provided on the top surface outer edges to receive a ridge 175 on the bottom surface outer edges, preventing radial sliding/shear.

FIG. 13(*f-g*) depict two other variations of expanding rings. In FIG. 13(*f-g*), the rings are shown unexpanded and having cavities 177 to receive bosses 176, allowing rings to join together somewhat like LEGO® blocks. The ring of FIG. 13(*e*) has telescoping sections 178 including travel stops 179. Such a ring could be produced by additive manufacturing, such as the MICA FREEFORM™ process (Microfabrica, Van Nuys, Calif.) or other processes having adequate resolution, depending on ring size. When expanded, the telescoping sections extend to enlarge the ring and allow an unexpanded ring to pass through it; the travel stops prevent the ring from over-expanding and/or breaking into separate parts. The ring of FIG. 13(*f*) includes flexures/living hinges 180 which allow it to be elastically (or plastically) deformed into a shape in which the flexures are far less bent, and in some cases, straight, again allowing an unexpanded ring to pass through an expanded ring. Such a ring could be produced by high-resolution injection molding from a material such as polypropylene, by companies such as MTD Micro Molding (Charlton, Mass.), depending on ring size.

In some embodiment variations, the rings of FIG. 13 are normally contracted, but can be stretched by a balloon (or other device) into an expanded configuration as shown in FIG. 13(*d-e*). In such an embodiment variation, the teeth and recesses of FIG. 13(*a-c*), and the ridge and groove of FIG. 13(*d-e*) also maintain the rings in an expanded configuration once the rings are stacked and the balloon has been removed, much like the 4$^{th}$ embodiment. Before moving proximally to stack a ring against another ring, the balloon can be rotated (e.g., by twisting the shaft to which it is attached) so as to adjust the relative orientation of each ring, thus achieving the desired amount and direction and curvature, as already discussed. In some embodiment variations, the rings of FIG. 13(*d-e*) are made from superelastic nickel-titanium or a polymer such as polypropylene or polyethylene such that the hinges can bend easily and without fracture. In some embodiment variations, the hinges can rotate at pivot points, not simply bend compliantly. In such embodiment variations, an elastic member (e.g., a band) may be provided to spring the ring either open or closed, or springs (e.g., torsional or leaf) may be incorporated at the pivot joints.

In some embodiment variations, rings may interlock using interlocking textured surfaces such as VELCRO® or an array of small mushroom-like protrusions (e.g., the DUAL LOCK™ fastener from The 3M Company, St. Paul, Minn.). The gear teeth already discussed provide a finite, quantized number of relative angles between rings, but in some embodiment variations, even fewer (e.g., 3-6) relative angles may be required. In such cases, providing rings with just a few protrusions on one surface and corresponding depressions on the opposite surface may suffice.

In some embodiment variations, rings may be held tightly against one another by one or more tensioned wires which run through the rings from most proximal to most distal; as a new ring is added, the wire(s) are transferred to the most distal ring. In some embodiment variations, rings are held against one another by magnetism. For example, the rings may be made of a ferromagnetic material, and placed in a magnetic field, or a magnet may be in contact with the most proximal ring and the magnetic flux conducted through the entire stack as more rings are added, making each new ring hold onto the previously-added ring. In some embodiment variations, magnetically-assisted contact may be used during the distal assembly process, but when all rings are deployed, another means of clamping the rings tightly against one another may be employed, such as one or more wires which run the length of the stack.

In some embodiment variations, the rings or at least one of their mating surfaces are compliant (e.g., an elastomer) such that when the rings are in contact, a seal is made between rings, thus allowing liquid or gas to be channeled without leakage from one end of the ring stack/cannula to the other.

In some embodiment variations, rings that are both offset as in FIG. 12 (*c-e*) and wedge-shaped as in FIG. 12(*f-h*) may be used.

Figure 14:
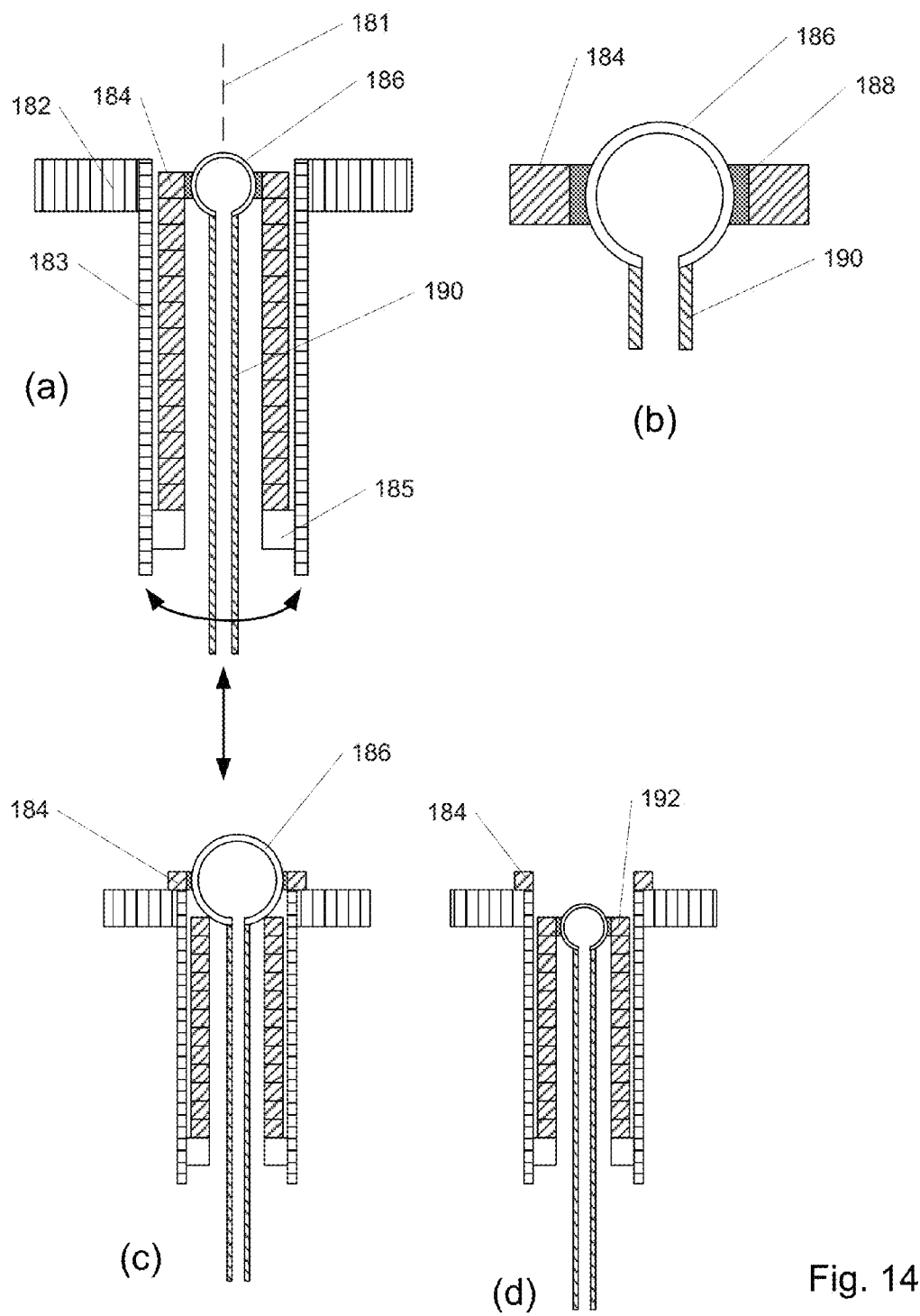

FIG. 14 shows in cross-section apparatus used in some embodiment variations to deliver a distally-assembled cannula comprised of rings, such as that described in FIG. 12(*f-h*) or FIG. 13. The geometry shown is rotationally symmetric around axis 181. As shown in FIG. 14(*a-b*), a plate 182 is connected to a tube 183 in which a stack of unexpanded rings such as ring 184 is loaded, supported by support 185. Balloon 186 is provided with gripping shoes 188 (shown in FIG. 14(*b*), a detail view of FIG. 14(*a*)) which engage one ring at a time in the stack (currently ring 184) when the balloon is slightly inflated as shown. Balloon 186 is attached to flexible hollow shaft 190, which can rotate and translate as indicated by the arrows.

In FIG. 14(*c*), balloon 186 has been translated distally, carrying with it ring 184, and then inflated by passing fluid through shaft 190, expanding ring 184. Ring 184 is rotated to the correct orientation by torqueing shaft 190 and placed against plate 182 (which may have features that keep the ring expanded) and balloon 186 is then collapsed and retracted distally where shoes 188 can fit into ring 192, the next ring on the stack. If the device is deployed within tissue, the balloon may also serve to dissect (e.g., blunt dissection) and/or displace tissue to as to make room for additional rings and create a pathway for the device. The distal assembly process is then repeated, with ring 192 being stacked in expanded form and with the desired orientation onto ring 184, where it is slightly more distal than ring 184. The process is further repeated until as many rings are stacked in expanded form as are needed. Disassembly of the cannula involves a process of approximately reversing the steps required to assemble it, and in some embodiment variations unexpanded rings end up inside tube 183 as before.

In some embodiment variations, rings may be pre-oriented or pre-selected such that when assembled, they form a cannula of the desired 3-D curvature, and little or no balloon rotation is required. In such variations, is may be important to prevent the rings from inadvertently rotating to an improper orientation before being assembled. One means of accomplishing this is to make the rings a shape other than round (e.g., polygonal) on their OD and make the inside of tube 183 have a matching shape that prevents ring rotation. In some embodiment variations, for example in the case of pre-oriented rings which require little or no rotation, the rings can have different wedge angles, rather than have all the same wedge angle.

In some embodiment variations, rings may not have substantially co-planar tops and bottoms. For example, segments such as segment 174 in FIG. 13 can have different heights, thus influencing the stacking orientation of adjacent rings.

Figure 15:
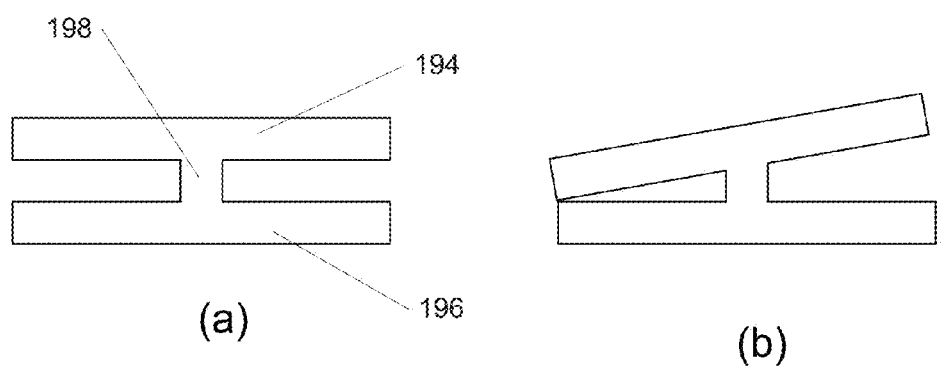

FIG. 15 shows a partial method of manufacture for wedge-shaped rings. In FIG. 15(*a*), a ring is produced in one piece, and then machined to form an upper ring 194, a lower ring 196, and a bridge 198 joining them. Then, in FIG. 15(*b*), the upper plate is reoriented relative to the lower plate by plastically deforming the bridge.

In some embodiment variations, in lieu of rings expanded radially as shown in FIG. 12(*a*), rings may be in the form of flat spirals, which are expanded (or contracted) by twisting them, balloon expanding them, etc. In the expanded, strained configuration, if not plastically deformed, they may be maintained in that configuration by ratcheting mechanisms, clips, etc.

7th Embodiment

We now turn to a set of embodiments which may be more suitable for producing steerable instruments which are not necessarily rigid on their own (if unsupported by surrounding tissue or other material) and may therefore be better suited for applications in which it is desirable to access a target region embedded in surrounding tissue.

Figure 16:
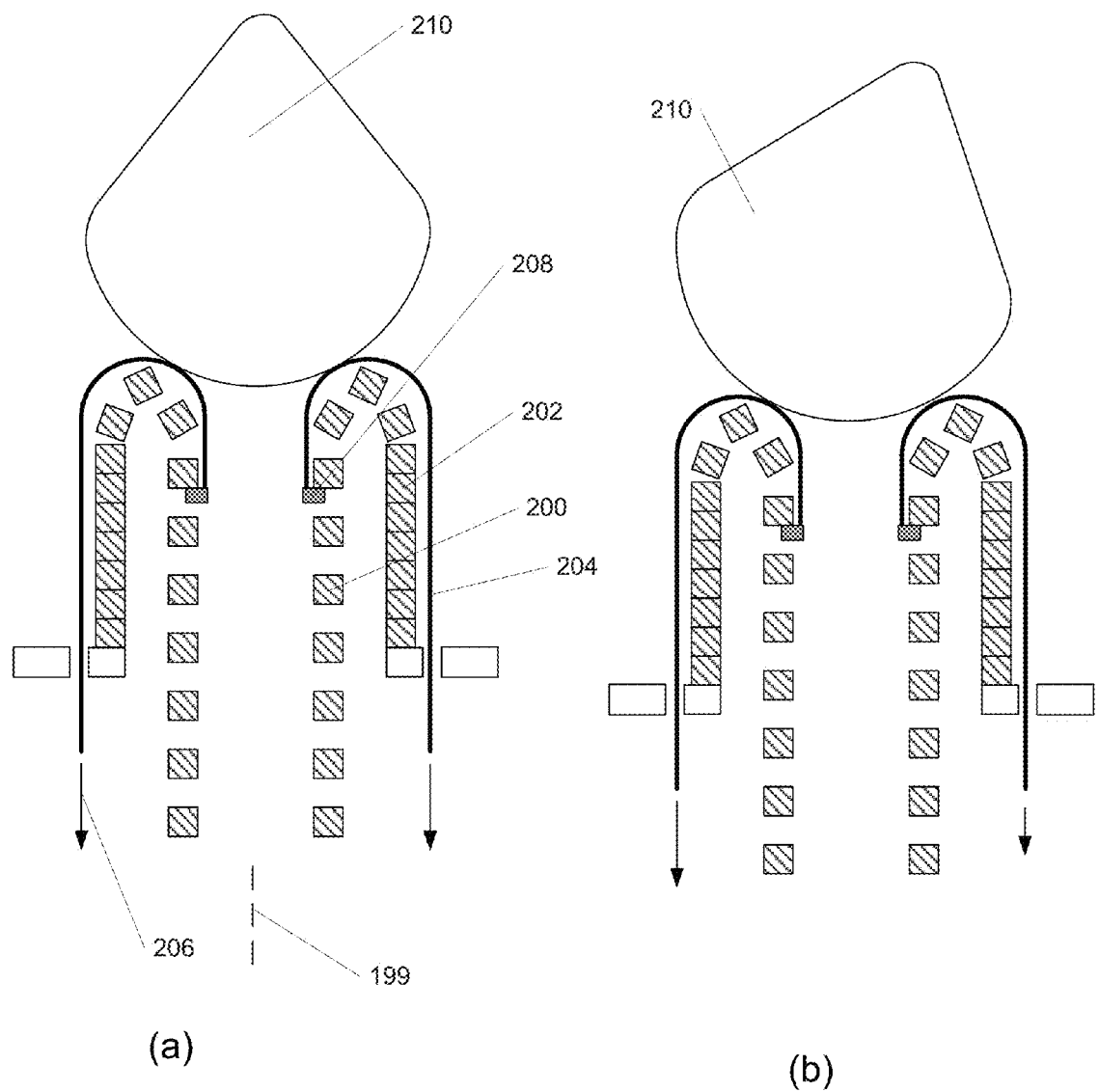
FIGS. 16(a)-(b) show an embodiment of a distally assembled device.

FIG. 16 shows a cross-sectional view of a 7th embodiment of the invention similar in some aspects to previous embodiments. The geometry shown is rotationally symmetric around axis 199. As shown in FIG. 16(*a*), a tube (e.g., a braided tube of Nitinol (nickel-titanium) wire) is everted and has both inner walls 200 and outer walls 202, the latter forming a cannula. Wire turns of the tube 200 located on inner walls are axially expanded and radially collapsed, whereas wire turns 202 on outer walls are radially expanded and axially collapsed. If the wire turns 202 are fully collapsed, the cannula may be self-supporting and suitable for use surrounded by fluid. As the inner walls move distally in the process of extending the cannula, inner turns 200 evert and are transformed into outer turns 202. In some embodiment variations, the distal motion may be implemented by pushing inner turns 200 distally (e.g., if surrounded by a tube, not shown, to prevent inner turns from prematurely collapsing axially and expanding radially). In other embodiment variations, the motion may be implemented by pulling on wires 204 in the direction 206. The distal ends of wires 204 engage inner turns 200 through the use of repositionable hooks 208 or other means, such that pulling on wires 204 pulls inner turns distally. Wires 204 are curved over the everting tube as shown, with the tube acting to reverse their direction of motion. In some embodiment variations, a ring or set of rollers, not shown, located between wires 204 and everting tube reduces friction between wires 204 and tube and prevents deformation of tube. At the distal end of the instrument is a tip serving to penetrate tissue with minimal force, and acting as a stylet to prevent tissue coring (tissue entering the lumen formed by the inner walls). Once the cannula has obtained the full length desired, tip 210 can be collapsed and removed, displaced, drilled through, etc. if it interferes with the procedure.

To extend straight ahead, penetrating through tissue, wires 204 are pulled an equal distance. In order to extend the instrument along a curved path, not all wires are pulled an equal distance or with an equal tension. For example, as shown in FIG. 16(*b*), the left wire is pulled more or tensioned more than the right wire. This has the effect of forcing turns on the left side to pile up faster on the outer tube, tending to tilt the tube to the right. Moreover, tip 210, if in contact with the wires as shown, can be rotated by them even though there is some slip between wires 204 and tip 210; the direction of tip rotation, with bottom of tip 204 (which may be a section of a sphere) acting as a pulley, is also toward the right. As the cannula lengthens and penetrates into tissue, the biasing of the everting tube and tip caused by uneven wire motion or tension causes the cannula to curve in its trajectory. As the cannula extends, it forms a liner for the tunnel through the tissue, reinforcing it and supporting it against collapse. In some embodiment variations, the liner may be largely or completely non-porous, allowing fluid transport. In some embodiment variations (e.g., when a braided tube is used), a thin, separate continuous liner is provided which everts along primary tube and provides a leak-proof conduit.

The length of the everting tube can be adjusted prior to cannula delivery such that inner turns 200 are completely everted and the resulting lumen is larger—determined by the ID of the outer turns—than it would be if not completely everted.

Refraction of the cannula can be accomplished by pulling the tube formed by inner turns 200 proximally. Or, if the tube has completely everted in order to maximize the lumen, wires can be provided that are affixed to the proximal ends of the tube; pulling these can reverse the eversion of the tube.

8th Embodiment

Figure 17:
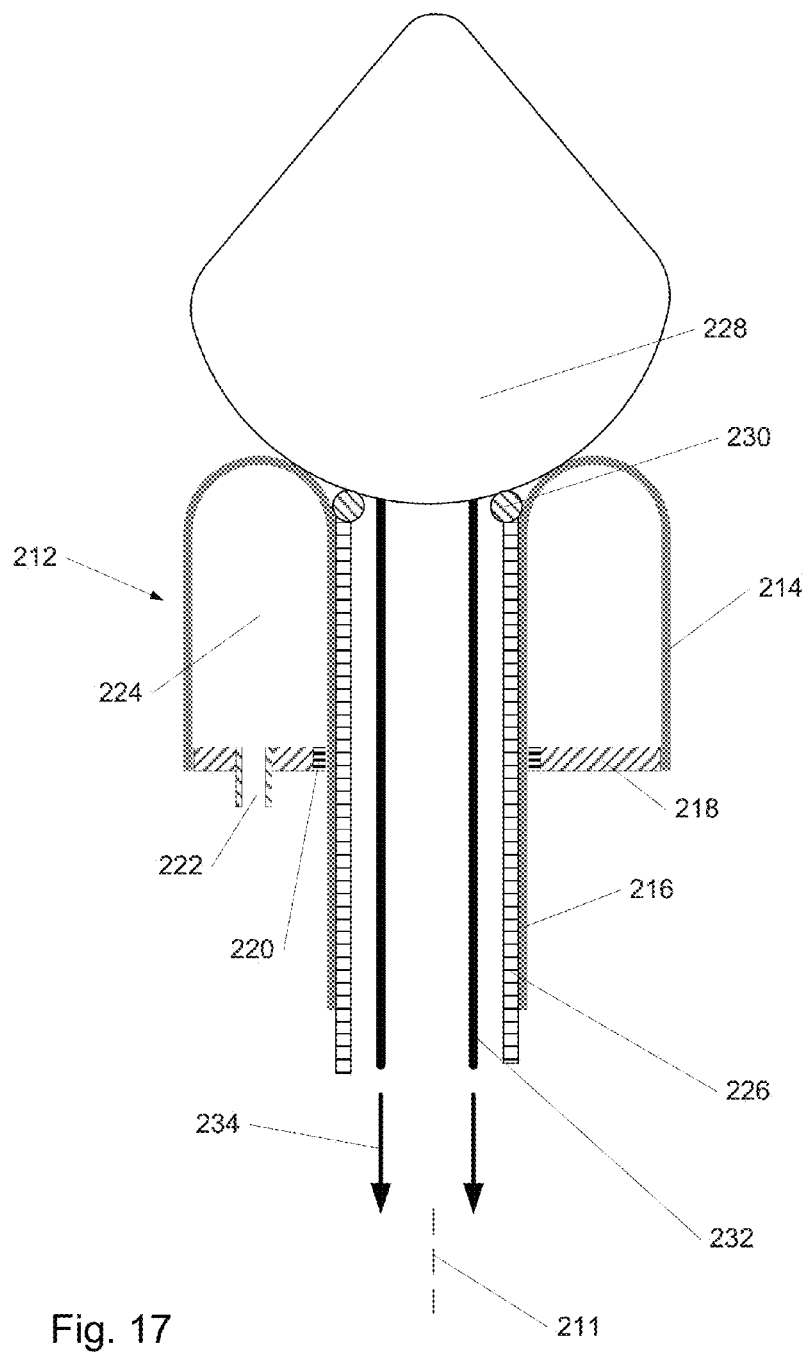
FIG. 17 shows an embodiment of a distally assembled device.

FIG. 17 shows a cross-sectional view of an 8th embodiment of the invention similar in some aspects to previous embodiments. The geometry shown is rotationally symmetric around axis 211. An everting flexible tube 212 (e.g., silicone rubber, Goretex) is provided, comprising outer walls 214 and inner walls 216. Outer walls 214 and inner walls 216 are bridged by rigid ring 218 which is optionally equipped with sliding seal 220 on its inner edge. Ring 218 is perforated to form a fluid inlet 222. When fluid (e.g., having a lubricating, low-friction property) is pumped into space 224 between outer walls 214 and inner walls 216, the pressure causes tube 212 to evert further and elongate. Outer walls 214 may in some embodiment variations be reinforced (e.g., by braid) to minimize bulging due to the fluid pressure. Also, in some embodiment variations, radially stiff and strong tube 226 is provided adjacent to inner walls 216 to prevent inward bulging and loss of ring/seal contact pressure. In some embodiment variations, compartment formed by tip 228 (see below) and inner walls 216 may be pressurized to minimize inward bulging of inner walls 216 and loss of ring/seal pressure. Tube 226 may also help to support tip 228, in some cases through ring 230. While tube 212 everts, tip 228 may be tilted and steered by applying differential tension to wires 232 attached to tip, in direction 234.

9th Embodiment

Figure 18:
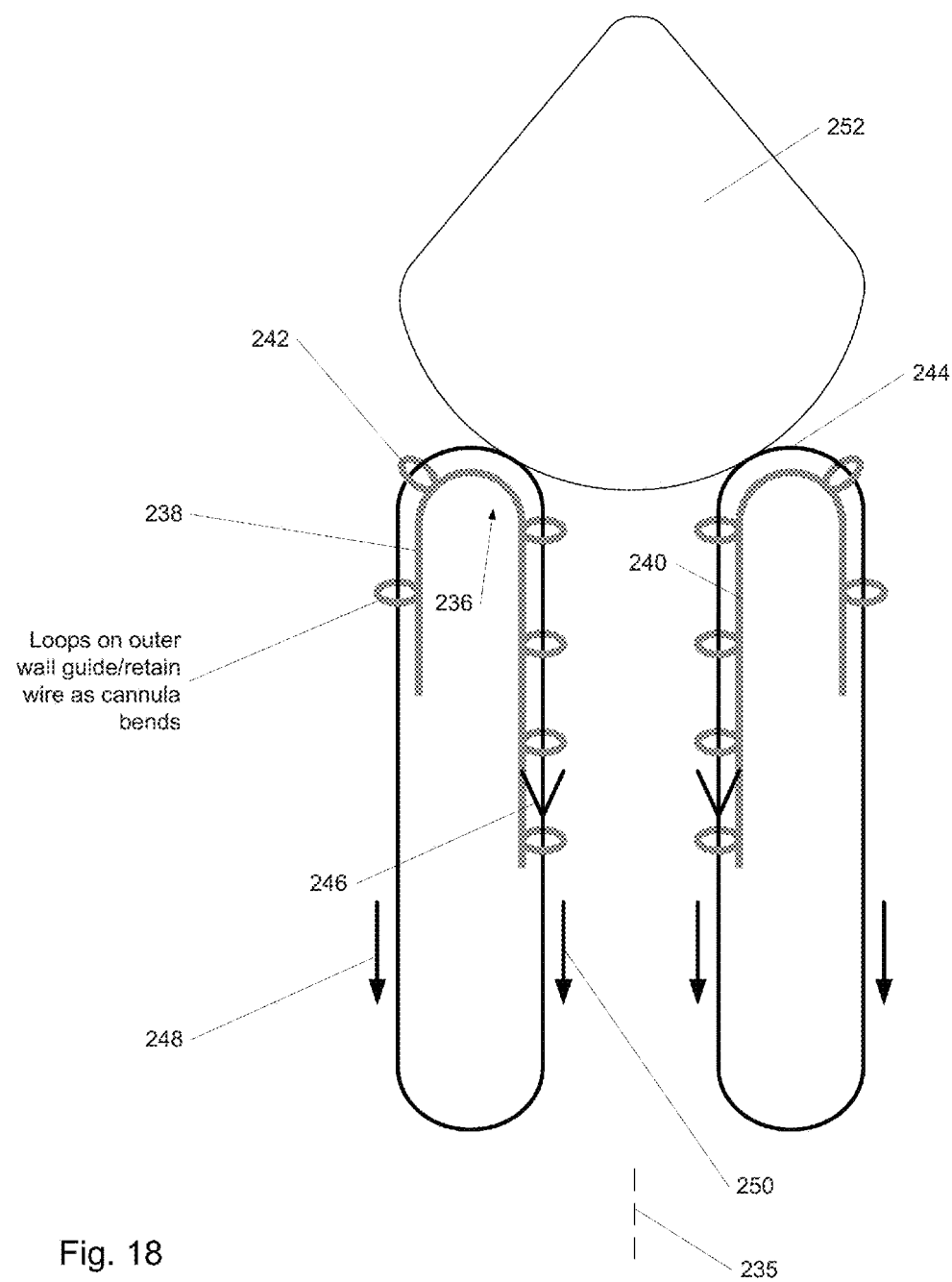
FIG. 18 shows an embodiment of a distally assembled device.

FIG. 18 shows a cross-sectional view of a 9th embodiment of the invention similar in some aspects to previous embodiments, and particularly to the 7th embodiment. The geometry shown is rotationally symmetric around axis 235. An everting flexible tube 236 is provided, which may for example be a continuous elastomeric tube or a braided metal wire tube, and having outer walls 238 and inner walls 240. In some embodiment variations, loops 242 are spaced (e.g., regularly) along the inside of inner walls 240, ending up on the outside of outer walls 238 as tube 236 everts. Running through loops 242 are wires 244 equipped with barbs 246. Wires 244 extend proximally and may be joined into continuous loops as shown. Loops 242 serve to advance inner walls 240 distally, extending the instrument, and also guide wires 244 on the outside of outer walls 238, such that when the instrument curves, wires 244 remain adjacent to outer walls 238.

When wires 244 are pulled in direction 248, barbs 246 engage loops 242 and pull inner walls 240 distally, further everting tube 236. After thus pulling inner walls 240 a short distance, wires 244 are then pulled in direction 250 a short distance such that barbs 246 pass in a proximal direction (i.e., proximally) through the next most proximal loops, engaging them in preparing for the next cycle, in which wires 244 are again pulled in direction 248. When all wires 244 are manipulated (e.g., alternating between pulling in directions 248 and 250) at the same rate, tube 236 everts and extends straight, forcing tip 252 into tissue. When wires 244 are not all manipulated at the same rate, tube 236 will tend to bend away from the direction in which the rate is higher, forcing tip 252 into tissue in a new direction. In some embodiment variations, tip 252 may also be tilted, e.g., through the use of wires such as wires 232 in FIG. 17. In some embodiment variations, in lieu of loops 242, if tube 236 has openings or recesses in its side (e.g., as a braided wire tube would), a ball (or bead or other shape) affixed to wire 242 can be used to pull inner walls 240 directly. In such a case, the ball can be maintained within the openings/recesses by a stylet or tube (possibly elastomer) adjacent to the wires inside the instrument, or by a balloon. Such a balloon may periodically be lowered in pressure to allow the ball to be easily repositioned by pulling wire 244 in direction 250 so it can engage a more proximal opening/recess.

10th Embodiment

Figure 19:
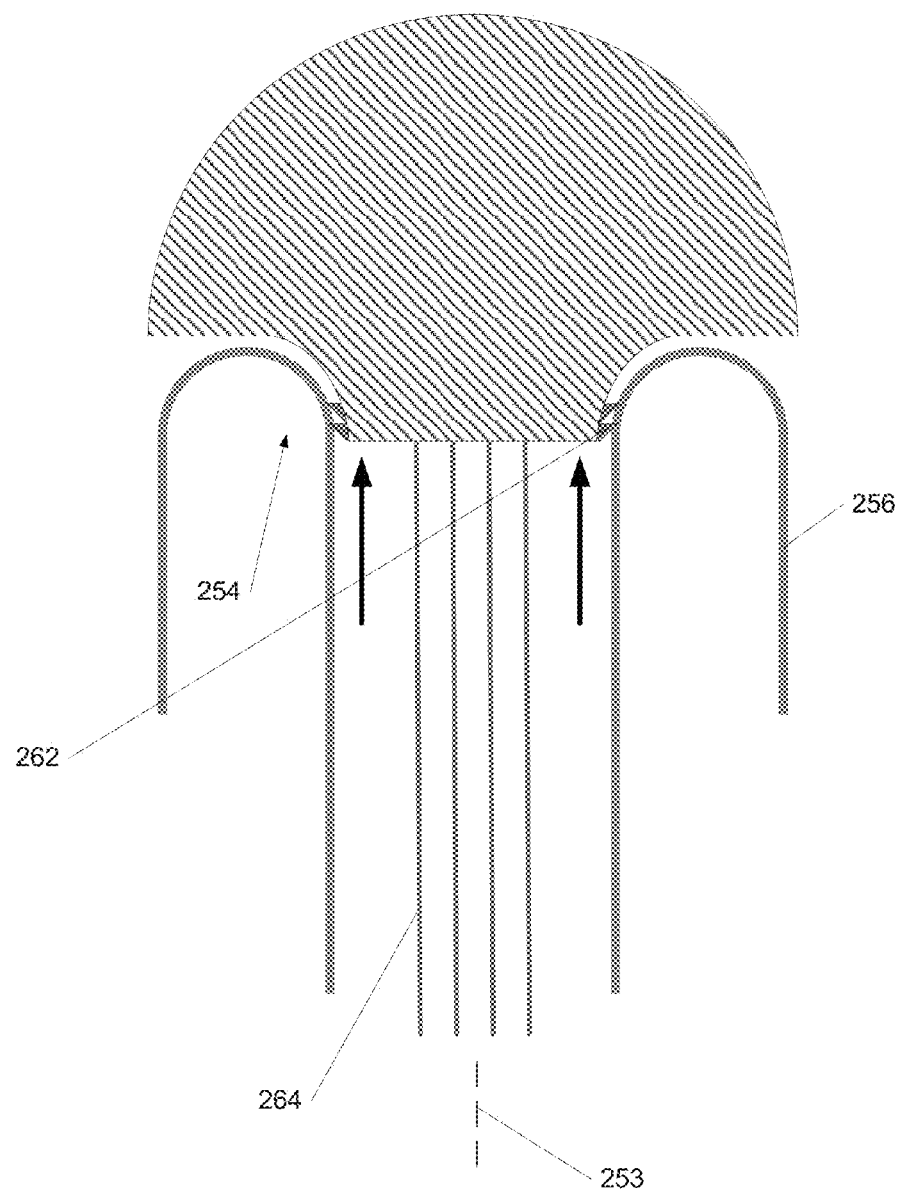
FIG. 19 shows an embodiment of a distally assembled device.

FIG. 19 shows a cross-sectional view of a 10th embodiment of the invention similar in some aspects to previous embodiments, and particularly to the 9th embodiment. The geometry shown is rotationally symmetric around axis 253. Again an everting tube 254 is provided, having outer walls 256 and inner walls 258. A distal tip 260 (here shown rounded, however other shapes are possible, such as that of FIG. 18) is provided with actuators 262 which make contact with inner walls 258 and pull them in a distal direction (e.g., using an inchworm or rolling motion). Actuators 262 receive power through electrical wires 264. When actuators 262 are actuated at a uniform rate, tube 254 everts uniformly and extends distally along a straight path. When actuators 262 are actuated at a non-uniform rate, the distal extension is along a curved path whose direction and radius of curvature depend on the relative actuation rates.

11th Embodiment

Figure 20:
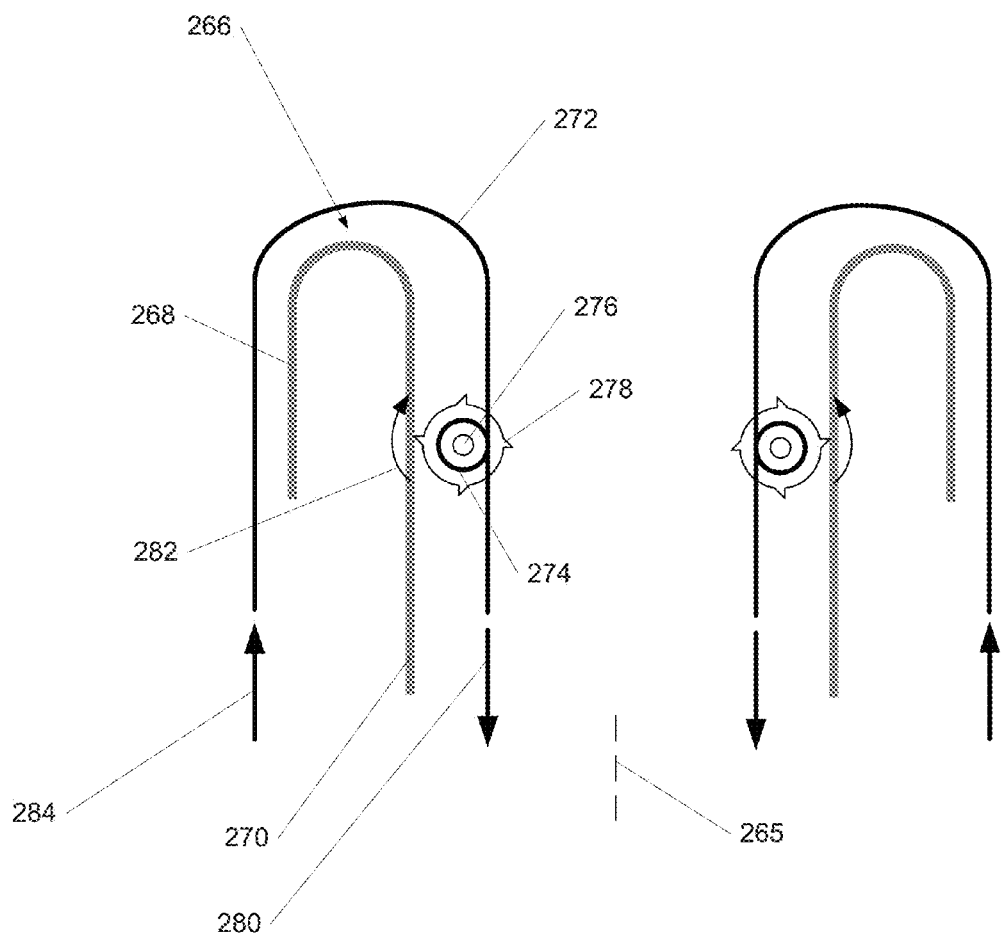
FIG. 20 shows an embodiment of a distally assembled device.

FIG. 20 shows a cross-sectional view of an 11th embodiment of the invention similar in some aspects to previous embodiments, and particularly to the 9th embodiment. The geometry shown is rotationally symmetric around axis 265. Again an everting tube 266 is provided, having outer walls 268 and inner walls 270. Wires 272 are provided, which run in the direction shown, and which may be joined into loops as in FIG. 18. A distal tip (not shown) may also be provided. Wires 272 are wrapped around wheels 274. Wheels 274 turn on axles 276 mounted to distal tip or to a flexible tube or shaft (not shown) running down the lumen of the instrument, adjacent to the wheels. Wheels may be provided with teeth 278. When wires 272 are pulled in direction 280, wheels 274 are rotated in direction 282, causing inner walls 270 to be pushed distally, thus further everting tube 266. Wire motion can be continuous in one direction in some embodiment variations. In other embodiment variations, in which wheels 274 are provided with a ratcheting mechanism that only allows rotation in direction 282, wire motion can be reciprocating, alternating between motion in direction 280 and motion in direction 284. In such embodiment variations, retracting of the device requires removing or reversing the ratcheting mechanism.

When wires 272 are pulled or cycled at a uniform rate, tube 266 everts uniformly and extends distally along a straight path. When wires 272 are pulled or cycled at a non-uniform rate, the distal extension is along a curved path whose direction and radius of curvature depend on the relative pulling/cycling rates.

12th Embodiment

Figure 21:
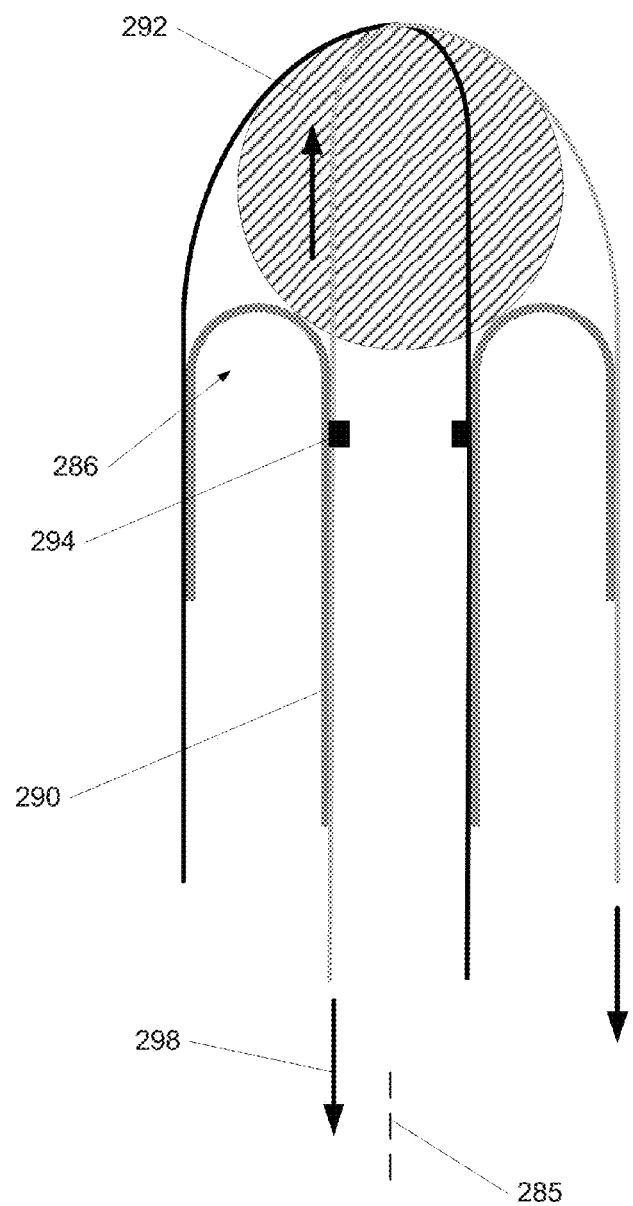
FIG. 21 shows an embodiment of a distally assembled device.

FIG. 21 shows a cross-sectional view of a 12th embodiment of the invention similar in some aspects to previous embodiments and particularly to the embodiments of FIGS. 16 and 18. The geometry shown is rotationally symmetric around axis 285. Again an everting tube 286 is provided, having outer walls 288 and inner walls 290. Wires 292 are provided which extend upwards along outer walls 288 and over a surface 292 which redirects them downwards, where they attach to temporary anchors 294 and then continue proximally out of the instrument. Wires 292 may be joined into loops such as wires 244 in FIG. 18. Surface 292 may be, for example, spherical, and may be the distal tip of the instrument, or a portion thereof. Anchors 294 may be of the type described in the 9th embodiment (e.g., balls which enter depressions in inner walls 290) or of another design, such that anchors 294 will securely grasp inner walls 290 when wires 292 are pulled in direction 296, but will loosen their grip when pulled in direction 298.

When wires 292 are pulled in direction 296, anchors 294 grasp inner walls 290 and pull inner walls 290 distally, further everting tube 286. After pulling inner walls 290 a short distance, wires 292 are then pulled in direction 298 a short distance such that anchors 294 can grasp a more proximal region on inner walls 290 in preparation for the next cycle, in which wires 292 are again pulled in direction 296. When all wires 292 are manipulated (e.g., alternating between pulling in directions 296 and 298) at the same rate, tube 286 everts and extends straight, forcing the tip into tissue. When wires 244 are not all manipulated at the same rate, tube 236 will tend to bend away from the direction in which the rate is higher, forcing the tip into tissue in a new direction. In some embodiment variations, the tip may also be tilted, e.g., through the use of wires such as wires 232 in FIG. 17.

13th Embodiment

Figure 22:
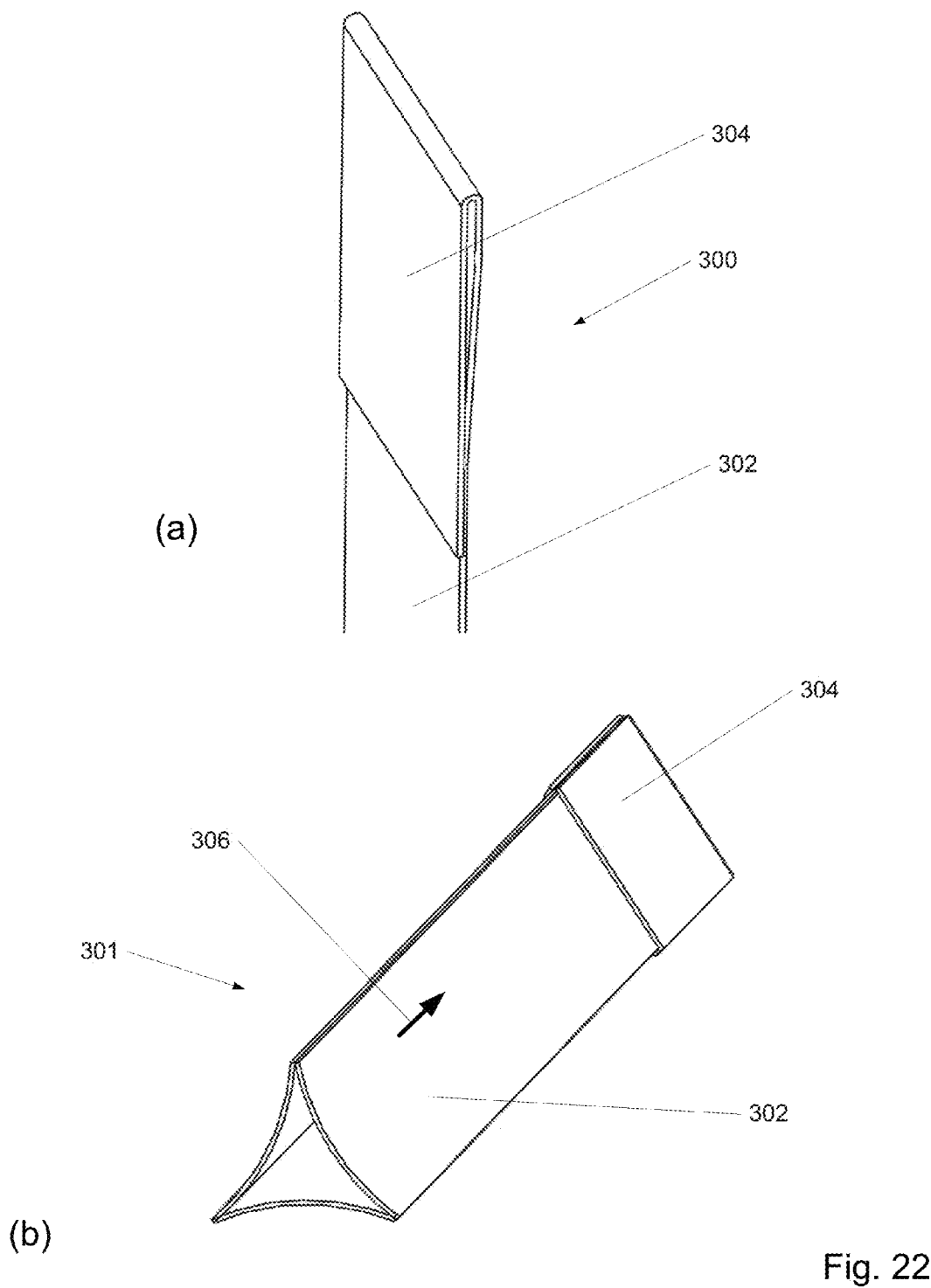
FIGS. 22(a)-(b) show an embodiment of a distally assembled device.

FIG. 22 shows a cross-sectional view of a 13th embodiment of the invention similar in some aspects to previous embodiments. In FIG. 22(a) a strip 300 of flexible material is provided. A curved region 302 of strip 300 is folded back on itself to form a substantially flat region 304. Three strips 300 are shown in FIG. 22(b) joined into a triangular tube 301, with regions 304 on the outside and regions 302 on the inside. Strips 300 are curved in regions 302 to allow strips 300 sufficient space inside flat regions 304 when assembled into tube 301.

If regions 302 are fed distally in direction 306, regions 304 will elongate in direction 306 as material from region 302 flows to the distal end of the tube 301, around the bend, and ends up on the outside as part of region 304. Strips 300 are joined by adhesive, seam welding, VELCRO®, DUAL LOCK™, etc. in such a way that if all strips 300 are fed distally at the same rate, the tube 301 resulting from joining them at their edges is straight. However, if strips 300 are fed at different rates, the tube 301 resulting from joining them at their edges will be curved. By adjusting the relative feed rates, evolving/everting tube 301 can thus be made to curve along a 3-D path. In some embodiment variations, more than 3 strips are used. For example, 6 strips may be fed distally, folded back onto themselves, and joined along their edges to form a tube with a hexagonal cross section. In such a case, the strips need not be curved initially, since there is adequate room to accommodate their width. Since unlike a triangular tube a hexagonal tube can collapse, appropriate bracing or reinforcement can be used, such as joining the strips using a method that provides rigid seams that maintain the strips at the correct relative angles.

14th Embodiment

Figure 23:
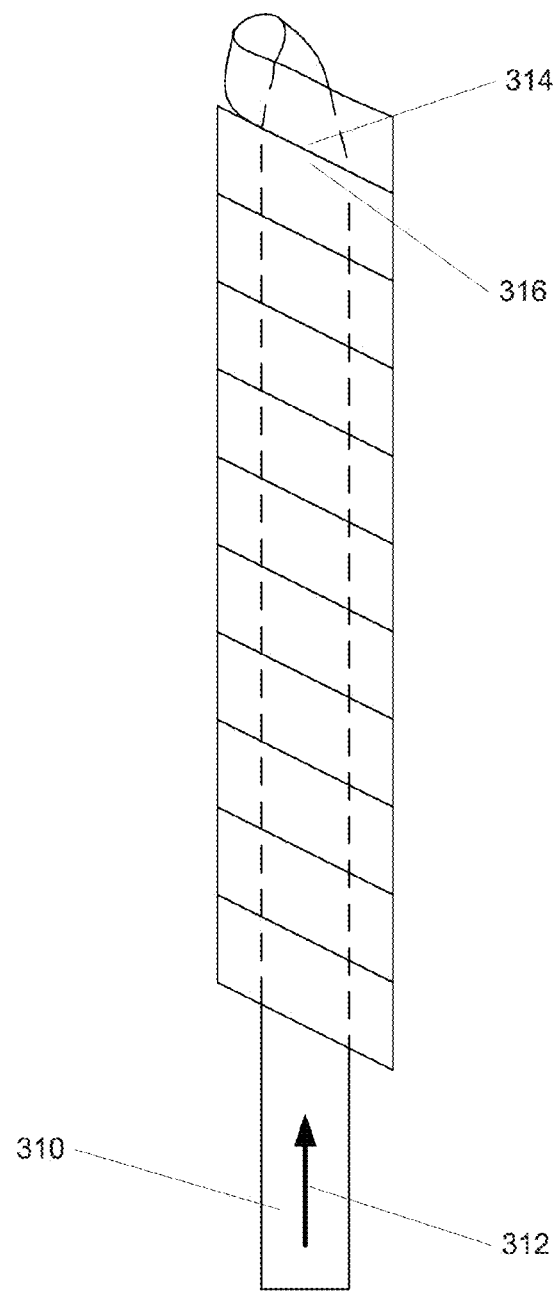
FIG. 23 shows an embodiment of a distally assembled device.

FIG. 23 shows a cross-sectional view of a 14th embodiment of the invention similar in some aspects to previous embodiments, and particularly, the 13th embodiment. In the figure, a relatively narrow strip 310 of flexible material is provided. The strip is fed distally in direction 312 through the lumen of a tube (e.g., round in cross section) that is formed by wrapping the strip in a helical pattern and joining the proximal edge 314 of the most distal wrap and the distal edge 316 of the next most distal wrap, with some degree of overlap (not shown) of the edges. Edges of strip 310 may be joined by adhesive, welding, VELCRO®, DUAL LOCK™, or other methods. The resulting tube 308 has a structure similar to a roll used to hold paper towels. As the seam is formed, the amount of overlap may be adjusted locally. If the overlap is circumferentially uniform, the tube will grow distally along a straight path. However, if the overlap varies around the circumference of the seam, the tube will bend and follow a non-straight path.

15th Embodiment

Figure 24:
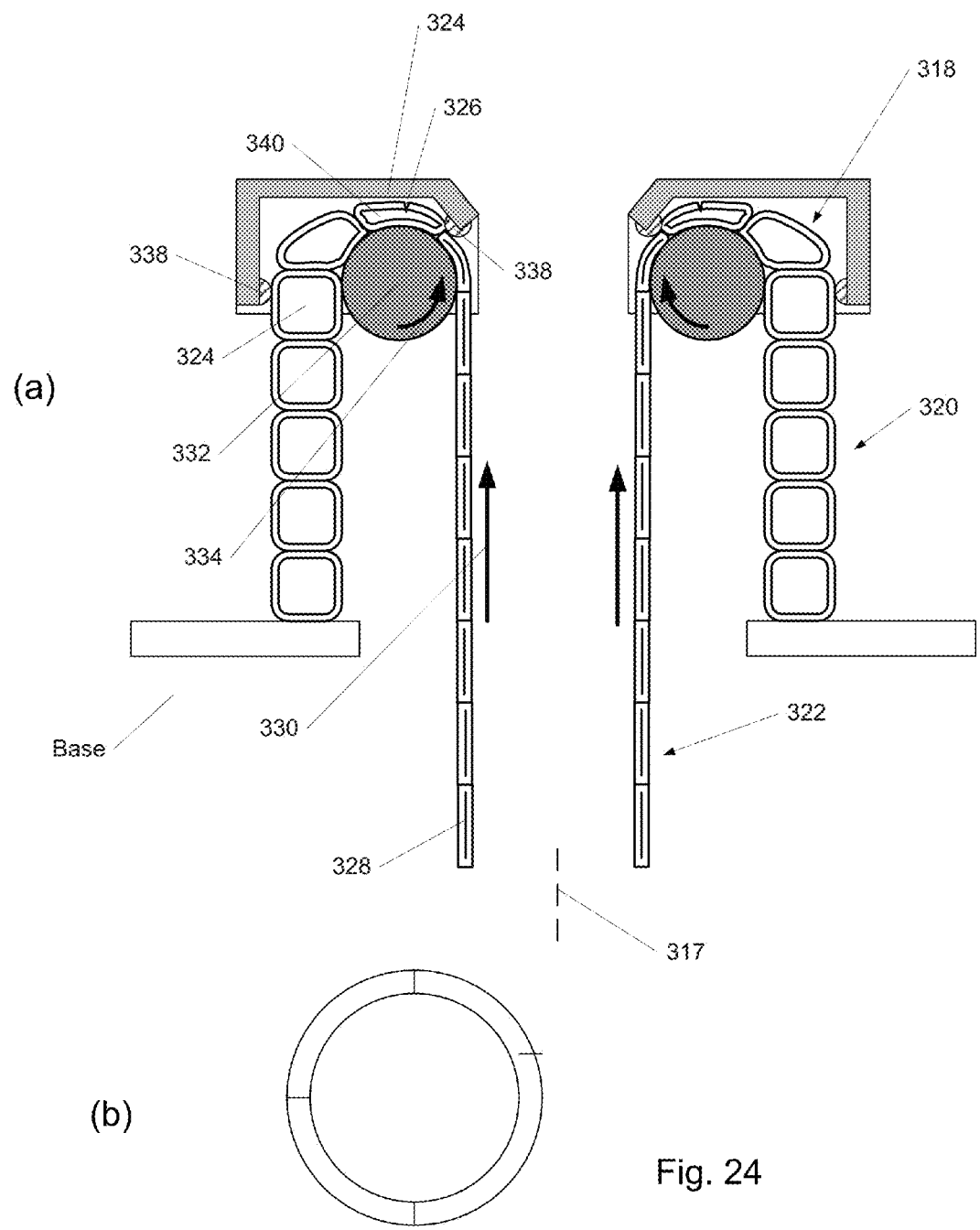
FIGS. 24(a)-(b) show an embodiment of a distally assembled device.

FIG. 24(a) shows a cross-sectional elevation view of a 15th embodiment of the invention similar in some aspects to previous embodiments. The geometry shown is rotationally symmetric around axis 317. In the figure, tube 318 is able to evert, having outer walls 320 and inner walls 322. The walls of tube 318 are comprised of flexible (e.g., elastomeric) sacs, which can be inflated with fluid such as sac 324. As shown in FIG. 24(b), in some embodiment variations, sacs have a partial-toroidal shape; in plan view, they appear as sections of tori spanning less than the normal 360 degrees for a full torus: for example, 90 degrees (as shown) or 120 degrees. Sacs are provided on their surface with slits 326 that allow them to be filled when slits 326 are widened as shown in the figure. Initially, forming at least part of inner walls 322, sacs are unfilled such as sac 328. As sacs move distally in direction 330, either pulled by rotating rollers 332 rotating in direction 334, they ride over rollers 332 (driven, for example, by motors, not shown) and enter chambers 324 sealed at its entrance and exit by seals 338. Within chambers 324, sacs such as sac 340 are inflated with fluid (in the figure, all sacs are shown equally inflated for simplicity). For example, while sac 340 is bent over roller 332, slit 326 on upper surface is widened and fluid can enter sac. When sac 340 has progressed further (e.g., to a position such as sac 324 exiting the chambers), slit 326 will have closed, trapping fluid inside sac 340. Chambers 324 are also of a partial-toroidal shape, each corresponding to a partial toroidal sac. The pressure to each of chambers 324 can be varied, such that the pressure inside each sac when it exits chambers 324 can also vary. If sacs are elastomeric, an increase in pressure will cause them to increase in size. In some embodiment variations, the increase in size is somewhat isotropic; however, in other embodiment variations, the increase in size is anisotropic, and primary along the direction of axis 317. This may be accomplished through the use of reinforcing bands in each sac wall, or other structures, and may be preferred, in that it allows sac height along axis 317 to vary more dramatically.

If all sacs at a given level (i.e., position along eversion/symmetry axis 317) are inflated to the same pressure, then assuming they are equivalent, tube/cannula 318 will grow in a direction parallel to axis 317. However, if the pressures are not equal, sacs with higher pressure and greater axial height will bend the growth direction away from themselves, causing the cannula to bend or curve as desired, along a 3-D path.

Retraction of the cannula can be accomplished by reversing rollers 332; sacs will enter chambers 324 and be emptied of their fluid contents and collapsed as they return to form inner walls 322 moving proximally.

In some embodiment variations, rather than providing sacs with a slit that can open to admit fluid, and chambers to fill sacs with fluid, sacs can be sealed and pierced by a needle (e.g., protruding from the surface of rollers 332). While so pierced, fluid can be injected into each sac. When the needle retracts, the sacs (e.g., if elastomeric) can re-seal, maintaining their charge of fluid within.

16th Embodiment

Figure 25:
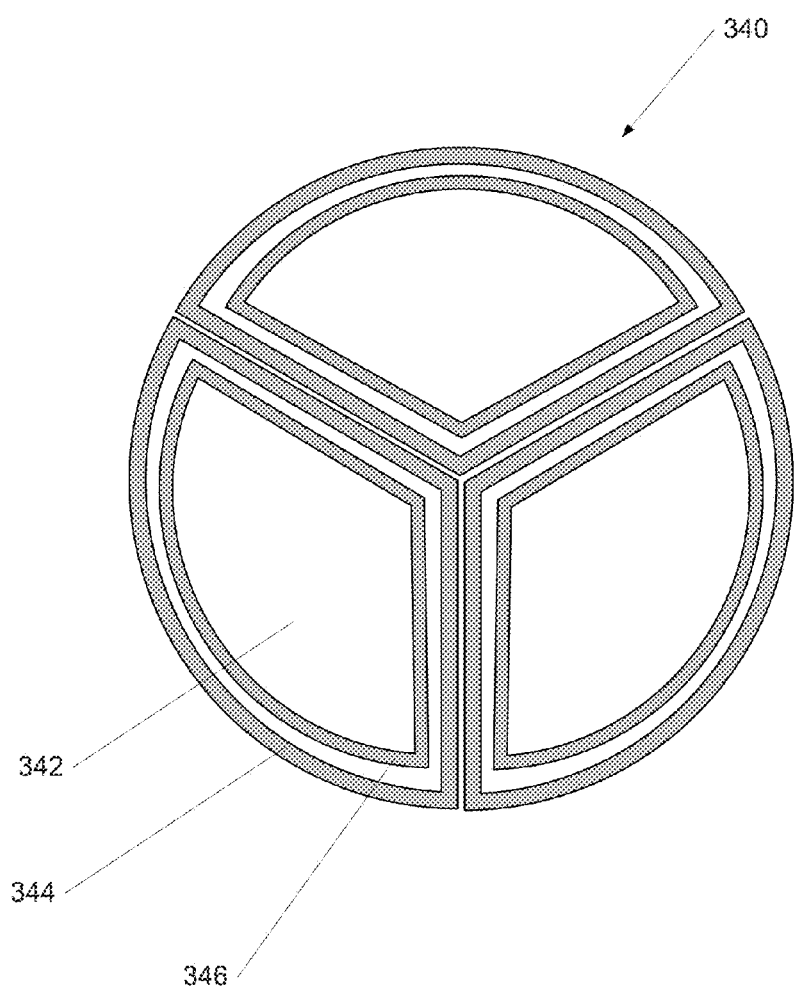
FIG. 25 shows an embodiment of a distally assembled device.

FIG. 25 shows a cross-sectional axial view of a 16th embodiment of the invention similar in some aspects to previous embodiments. Tube 340 is comprised of several (e.g., 3-4) smaller tubes 342 joined or grouped together, each of which itself is cable of everting, e.g. in the manner shown in FIG. 17. Each tube 342 has outer walls 344 and inner walls 346. If each tube 342 everts at the same rate as it grows distally, tube 340 will grow to follow a straight path. But if the tubes do not all evert at the same rate, tube 340 will grow to follow a curved path. Adjusting the relative growth rates of tubes 342 thus causes tube 340 to follow the desired 3-D path in space. Tube 340 can be equipped at its distal end with a tissue-penetrating, non-coring tip (not shown).

17th Embodiment

Figure 26:
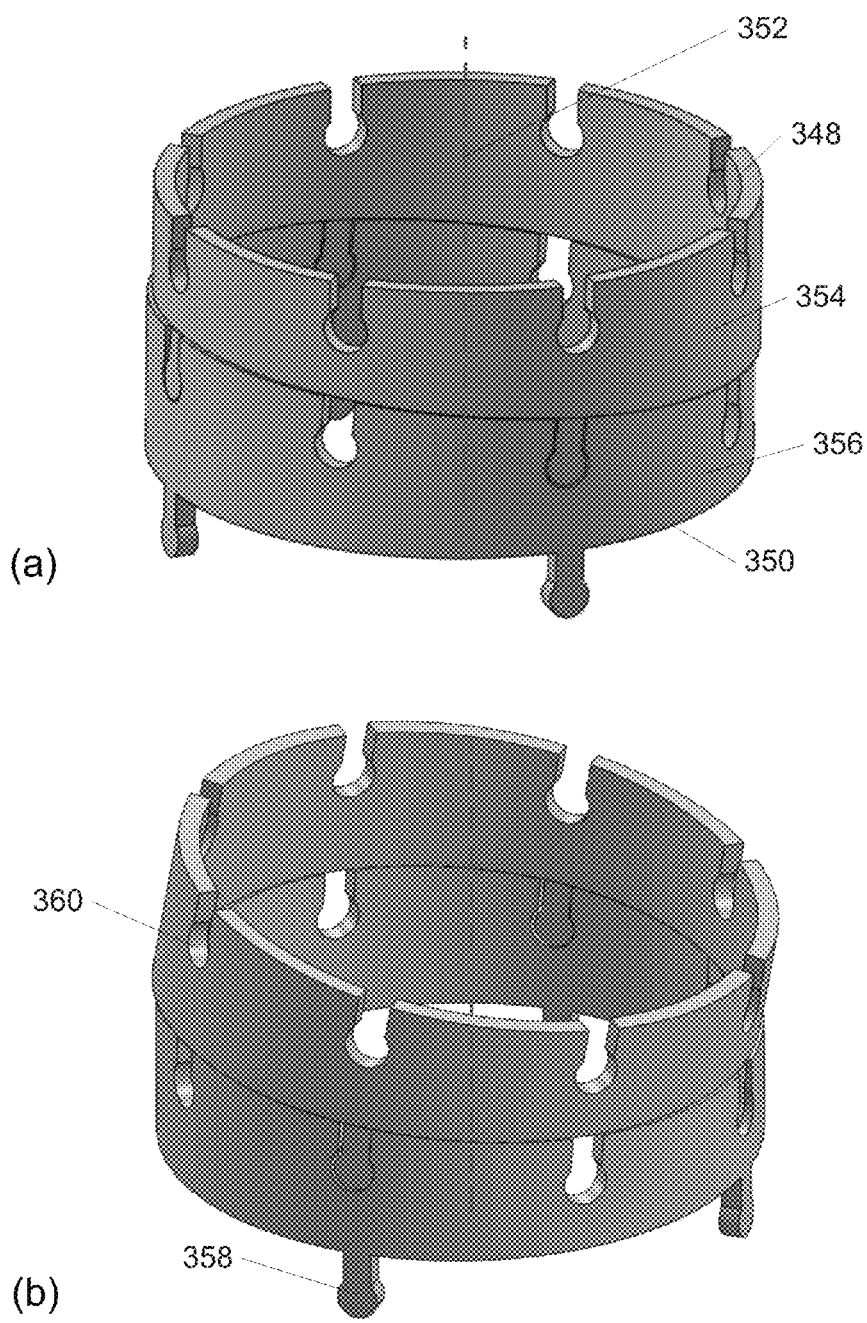
FIGS. 26(a)-(b) show rings associated with shows an embodiment of a distally assembled device.
Figure 27:
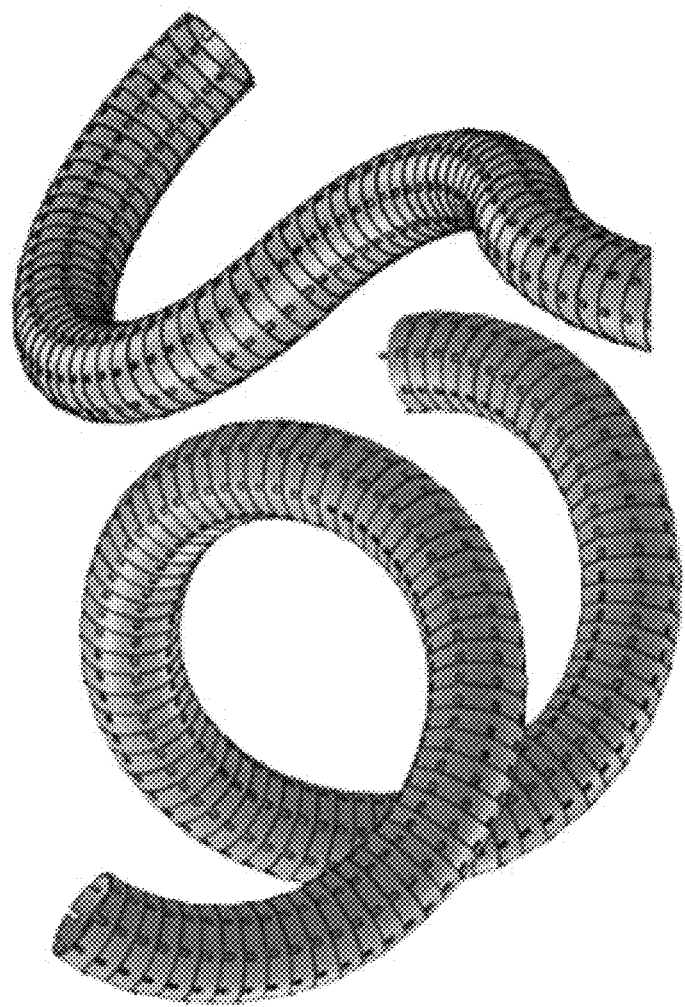
FIG. 27 shows cannulas produced using multiple rings.

FIGS. 26-41 depict a 17$^{th}$ embodiment of the invention similar in some aspects to the 6th embodiment. To distally grow DASC, material must be supplied to the distal end, preferably through the cannula. FIG. 26 shows a design in which material is provided in the form of rings with a wedge-shaped profile and which can couple or interlock. Preferably though not necessarily, these rings are of two different types as shown in the figures, and are used in alternation (i.e., in pairs), allowing straight cannula sections to be formed when the rings are suitably aligned as in FIG. 26(a). The distal face 348 or proximal face 350 of each rings is formed at a specified wedge angle relative to ring axis 352 (e.g., 5° as in FIG. 26), and are therefore not parallel. For distal ring 354 of the pair, distal face 348 is normal to the ring axis and proximal face 350 is at an angle other than 90 degrees; for proximal ring 356, proximal face 350 is normal to the axis and distal face 348 is at an angle other than 90 degrees (typically the same angle as that of the distal ring's proximal face). The relative orientation of the rings can be set so proximal face 350 and distal face 348 are parallel (FIG. 26(a)), at twice the wedge angle (FIG. 26(b)), or at intermediate angles. The angle between proximal and distal faces dictates the local curvature of the cannula, while the orientation of proximal ring 356 dictates the tilt direction of distal face 348 of distal ring 354. Thus, by adjusting the orientation of both rings independently, both curvature and direction can be controlled. With the eight-hole rings shown, five unique curvatures, each with eight directions, are possible. Each ring has four male coupling elements or tabs 358 extending perpendicularly from its proximal face and is perforated with a set of female coupling elements or holes 360 (here, eight) communicating with distal face 348 (in some embodiment variations, tabs 358 are provided on distal face 348 and holes 360 are provided communicating with proximal face 350). Tabs 358 and holes 360 mechanically interlock rings 354 and 356, providing stability in shear, torsion, and tension, and enabling a strong, rigid structure to be built. Two of tabs 358 are located close to the minor axis of the deformed, elliptical ring, and two close to its major axis. The wall thickness of the rings and tabs must be great enough to allow the rings to interlock, since tabs 358 will not necessarily be flush or tangent to the ring surface. Since the proximal face of ring 354 and the distal face of ring 356 may not be circular in shape due to the wedge angle (e.g., if the rings are cut from a tube), in some embodiment variations the rings are slightly deformed (e.g., plastically) to make these faces circular in shape. If a second pair of rings is mated to the first pair, the first pair's distal face establishes the plane of the proximal face for the second pair, and so on. FIG. 27 shows two cannulas, the lower one helical, both having complex 3-D shapes comprising dozens of rings such as rings 354 and 356. Notably, these cannulas differ only in the relative orientations of their rings.

Figure 28:
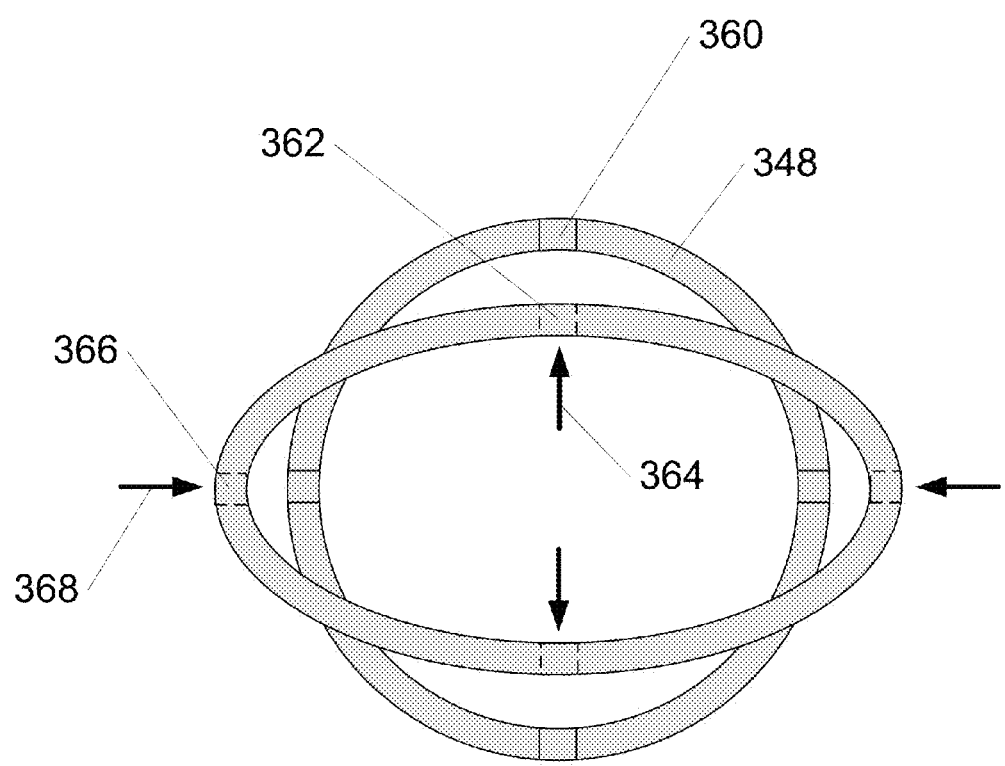
FIG. 28 shows how rings couple together.

Unlocking or locking the rings requires one ring to be temporarily compressed into a substantially elliptical shape. FIG. 28 is an axial view of a deformed elliptical ring in contact with a circular ring below. When the upper ring is allowed to relax into a circle, two opposite tabs 362 (shown in phantom view) from the top ring, located along the minor axis of the ellipse, move outwards in the direction of arrows 364 to enter holes 360 communicating with distal face 348 of the lower ring from the inside. Simultaneously, the remaining two opposite tabs 366 move inwards in the direction of arrows 368 to enter holes 360 from the outside. The four tabs thereby lock the rings together, and keep them interlocked until and unless at least one ring of the pair is deformed so as to cause tabs and holes to separate. In some embodiment variations, one of the tabs may be eliminated, yet the rings may still be interlocked and stable in shear, while in some embodiment variations, two of the tabs may be eliminated and an interior or exterior tube is provided, such that the rings when interlocked are still stable in shear. In some embodiment variations, more than four tabs may be used; for example, tabs may be provided in pairs, with the members of each pair relatively closely spaced. Typically the upper ring is unlocked by re-compressing it to extract tabs 362 and 366 from holes 360, after which the upper and lower rings can be separated.

Figure 29:
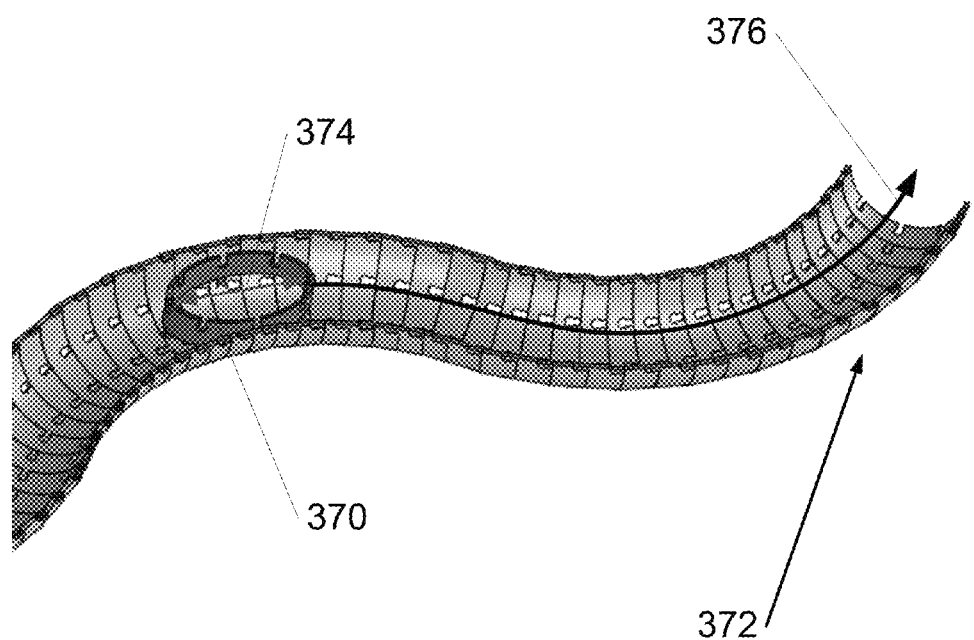
FIG. 29 depicts how rings are transported through the cannula.
Figure 30:
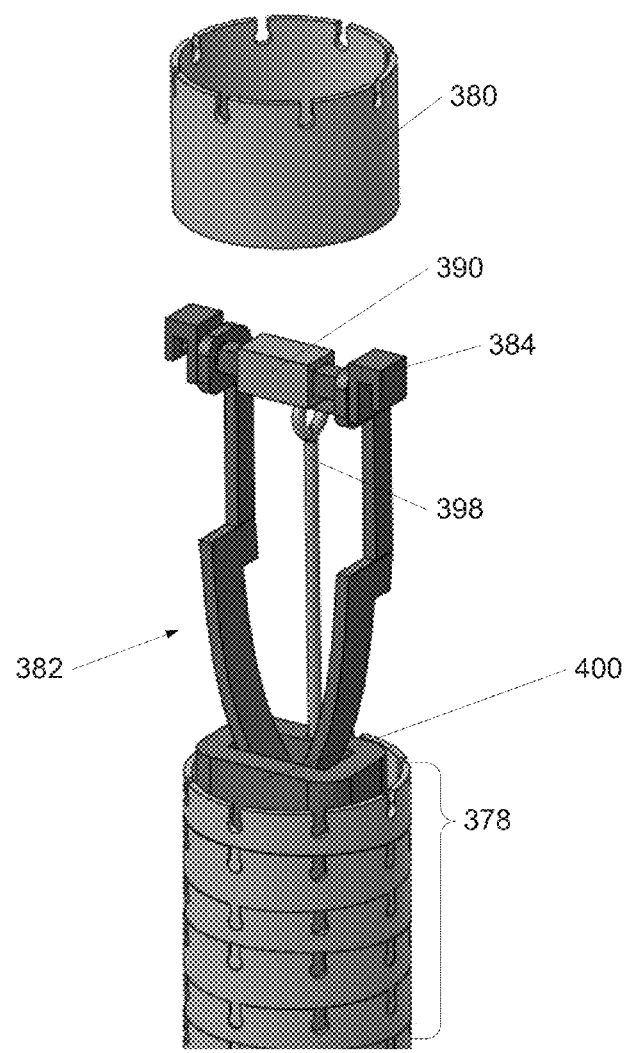
FIG. 30 depicts the head of a stylet and other components.

In the compressed state rings 370 can be transported through the cannula lumen toward distal end 372 (or towards the proximal end) by swiveling them so that the major axis 374 of the ellipse is substantially aligned with the direction of travel 376 (FIG. 29). Assembling/disassembling the cannula is accomplished using a robotically-actuated stylet that can compress, swivel, transport, and rotate rings based on high-level commands (e.g., "bend with 10 mm radius in a 7 o'clock direction"). The stylet includes a flexible shaft that is push-able and torqueable within the cannula, and a distal head. FIG. 30 shows the head of the stylet, along with stack of rings 378 ready for use, and base 380 that serves as a foundation for the cannula. Stack of rings 378 may be incorporated into a cartridge, not shown, that is easily loaded and unloaded from the DASC system; the rings may held ready for use either interlocked as shown in FIG. 30, or held separate from one another. Cartridges may vary in the size of rings they contain, the number of rings, the type of rings (e.g., hole count), ring radiopacity, etc. For access to deep anatomy, base 380 may be very long and rigid or flexible. In some embodiment variations, base 380 comprises a standard straight, flexible, or pre-shaped catheter. In some embodiment variations, stack 378 may be internal to the patient, not external, speeding assembly.

The stylet head includes deformable fork 382 tipped with two swiveling grippers 384. Each gripper 384 has a cylindrical boss 386 allowing rotation with respect to fork 382, a non-rotating (e.g., square as shown in FIG. 31(a)) boss 388 that slides within swivel block 390 (FIG. 30), allowing the fork to expand and compress, fin 392 tapered for easy insertion into the slot-shaped distal portion of hole 360 in ring 394, and cylindrical boss 396 which engages the circular portion of hole 360 in ring 394 (near ring 394's minor axis). Boss 396 enters the circular portion of hole 360 when gripper 384 is pulled inwards by compressing fork 382 (FIG. 31(b)), securely grasping ring 394; fin 392 allow grippers 384 to rotate ring 394 without slippage when a swivel wire 398 (FIG. 30) is slid to rotate swivel block 390 and thus rotate grippers 384. Passing over the proximal region of fork 382 is compression tube 400; when this is advanced, the flexible regions of fork 382 are compressed and grippers 384 are forced inwards, capturing and compressing ring 394. Not shown are flexures (e.g., attached to the stylet head) that center the stylet within the cannula and can help it glide through.

Assembly of the cannula (e.g., within a hollow region) proceeds in a preferably-automated fashion as follows: In FIG. 32(a), the stylet has retracted in direction 402 so that grippers 384 can engage the most distal ring 404 in the stack. In FIG. 32(b), compression tube 400 has compressed fork 382 in direction 406 so that grippers 384 compress ring 404 and unlock it from the remaining rings in stack 378. In FIG. 32(c) the stylet and ring have been advanced in direction 408 toward base 380. In FIG. 32(d), ring-swiveling wire 398 has been advanced in direction 410, causing swivel block 390 to pivot ring 404 as shown by arrow 412 until its major axis is roughly parallel to the substantially cylindrical axis of base 380, allowing ring 404 to move as shown by arrow 414 through base 380 until ring 404 has passed through base 380 as in FIG. 32(e). In FIG. 32(f), wire 398 has been retracted as shown by arrow 416, swiveling ring 404 as shown by arrow

418 until its major axis is roughly orthogonal to the axis of base 380. The stylet has also been rotated as shown by arrow 420 about its long axis to orient ring 404 at the correct angle relative to base 380; this operation may also be done prior to the stylet head and ring entering the cannula, or during the distal travel of the head and ring (e.g., to save time).

Figure 32:
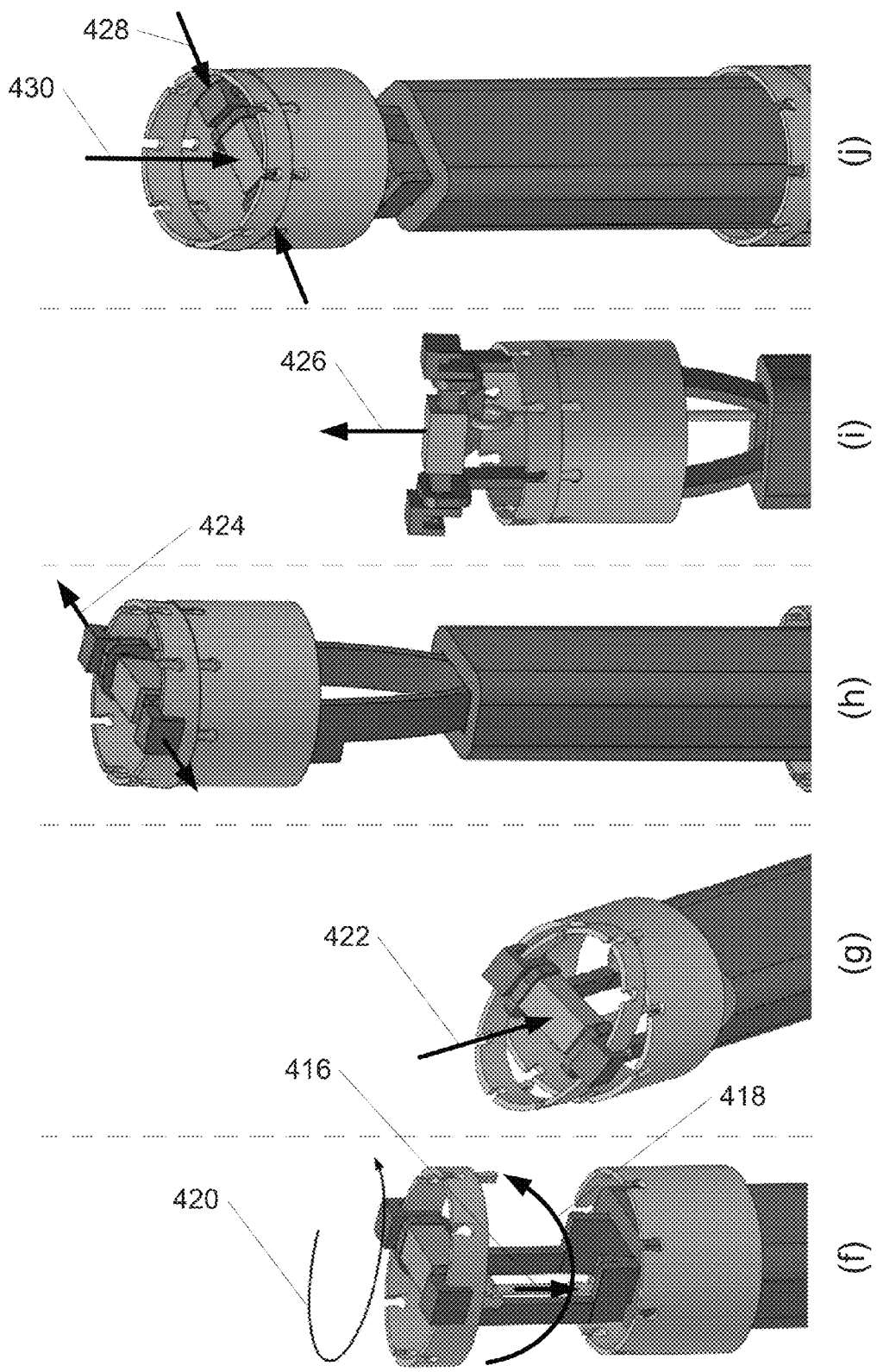
FIGS. 32(a)-(j) show a deployment sequence for a distally assembled device using rings.

In FIG. 32(*g*) the stylet has been pulled proximally in the direction of arrow 422, mating ring 404 and base 380 (ring 404 may be allowed to pivot freely, or swiveled to the required angle); a tensile load cell can be used to detect this event. In FIG. 32(*h*), compression tube 400 has been retracted, letting fork 382 and ring 404 expand as shown by arrows 424; as ring 404 expands, its tabs enter the holes of base 380, locking ring 404 and base 380 together. In FIG. 32(*i*), the stylet has advanced in direction 426 until grippers 384 are past the distal edge of ring 404. In FIG. 32(*j*), the tube has been advanced to compress fork 382 in direction 428 to fit through the lumen of ring 404 and base 380, after which the stylet is withdrawn in direction 430 to fetch the next ring in the stack. This cycle repeats for every ring, with newly-added rings coupled to rings already coupled to one another, or in the case of ring 404, to base 380. With all rings delivered and the cannula thus assembled, the stylet is retracted to open the lumen for the procedure; before use, a liner (e.g., a PTFE, silicone elastomer, polyethylene, or polypropylene tube) can be pushed through the cannula to render it fluid-tight if needed; the liner outside diameter may be close to or significantly smaller than the cannula/ring inside diameter. In some embodiment variations, the liner may include multiple lumens, be deployed into the cannula by everting, and/or be reinforced by a braid or coil. In some embodiments, the liner is anchored to one or more rings (e.g., the most distal ring) and then pushed distally or pulled proximally so as to help stiffen the cannula, by pre-loading rings against one another. In some embodiment variations, the rings stored in the stack may be advanced gradually as rings are removed, such that the most distal ring is always as close as possible to distal end of the cannula; this can be accomplished by a compression spring as in an ammunition magazine, etc. In some embodiment variations, rings are not removed from the distal end of the stack, but rather, from the proximal end, and transported through the stack as well as through the growing cannula.

With the procedure completed, disassembly proceeds roughly by reversing this process. The fork is compressed and advanced to the most distal ring, and the stylet rotated to match the ring's orientation when interlocked (the angle is stored in memory). The grippers engage the ring, compress it to unlock it, move it distally to swivel it, then retract and release it into a container (e.g., a waste container if the rings are disposable/single-use).

To maximize the reliability of ring interlocking and ensure that tabs enter holes properly, in some embodiment variations in the step shown in FIG. 32(*h*) the ring may be allowed to return to nearly circular form and the stylet rotated such that the tabs snap into the nearest holes. The angle to which the ring is rotated prior to this snapping behavior can be chosen so that the nearest holes are also the desired holes. Torsional compliance of the shaft can prevent shaft damage after the snapping occurs; in some embodiment variations the torsion on the shaft is measured to determine when the snapping has occurred, and further rotation of the shaft may be temporarily ceased. In some embodiment variations, the risk of incorrect ring orientation can be mitigated by using one or more optical fibers to detect holes in the ring and thus determine the angle at which the ring is orientated before the ring is mated. The holes used for interlocking and/or additional holes provided for optical detection can be detected optically using ambient light or light supplied by a local source or optical fiber (e.g., the same fiber used for detection). A special "index" hole having an unusual aspect (e.g., size, shape, or position) may be provided to provide absolute vs. relative orientation. In some embodiment variations, mechanical methods of aligning the head to the holes may be used. For example, the stylet head may incorporate spring-loaded balls (e.g., four arranged in a circle and separated by 90 degrees). The balls can be pressed against the inside of the most distal ring before mating a new ring; as the stylet head is turned, the balls "pop" in and out of the holes, using them as detents to align the head/new ring to the distal ring, and ensuring that the new ring can reliably interlock to the distal ring.

Methods of determining the orientation of the stylet head relative to the distal ring may also be used to ensure that the stylet head is correctly oriented with respect to the ring before an attempt to re-capture the ring by engaging, compressing, and decoupling it is made. Preferably the correct holes of the ring (i.e., those aligned with the minor axis of the deformed ring) are engaged by the grippers, though in some embodiment variations, holes near the correct holes may be suitable, or other holes used. In some embodiment variations, if ring coupling is completed and it is determined that the wrong or sub-optimal hole was used, the ring may be decoupled, re-oriented, and coupled again; this approach may also be used for iterative assembly of the cannula. DASC can be adjusted once assembled to change its shape by simply decoupling and re-orienting rings relative to one another, then recoupling them.

In some embodiment variations, to verify the ring is interlocked before it is released by the grippers, and mitigate the risk of dropping a ring into the patient, the stylet is advanced and the compressive force on it measured (e.g., using a load cell): if the force is less than expected, the ring can be automatically re-compressed, adjusted if needed, and re-interlocked. A similar method may be used in some embodiment variations during disassembly to minimize the risk of dropping the ring: to verify the ring is captured by the stylet head before the ring is decoupled from the next most distal ring, the stylet may be advanced proximally and the compressive force on the stylet measured.

Figure 33A:
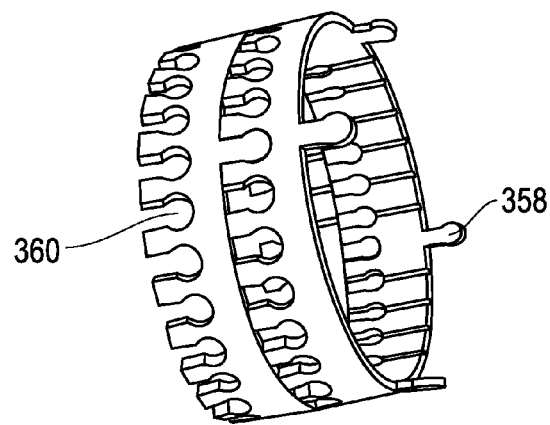
FIGS. 33(a)-(b) comprise photographs of scaled up rings and stylet head.
Figure 33B:
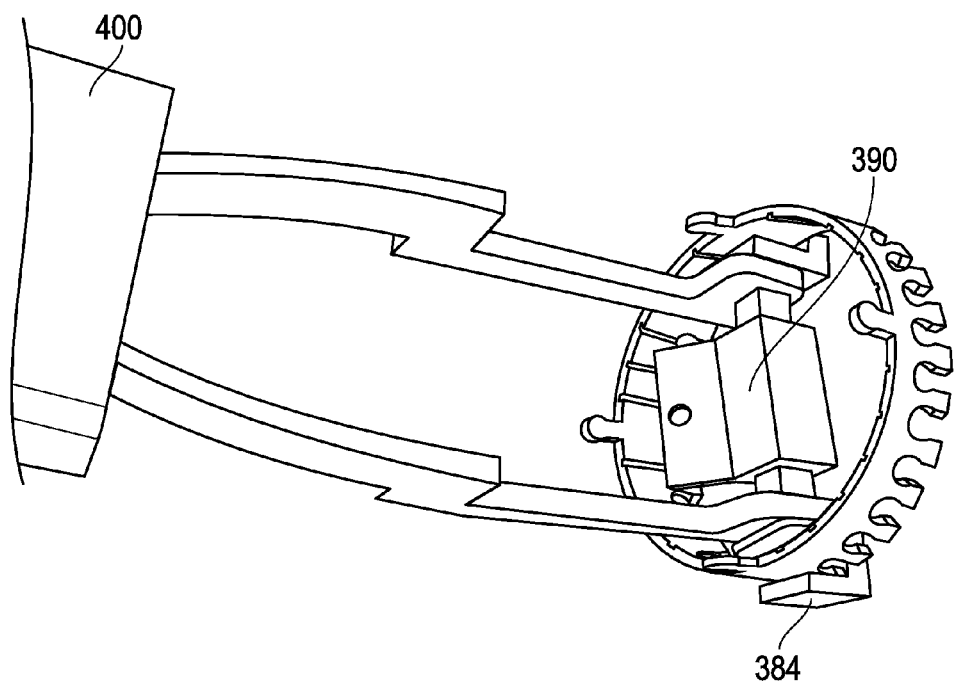
Figure 34:
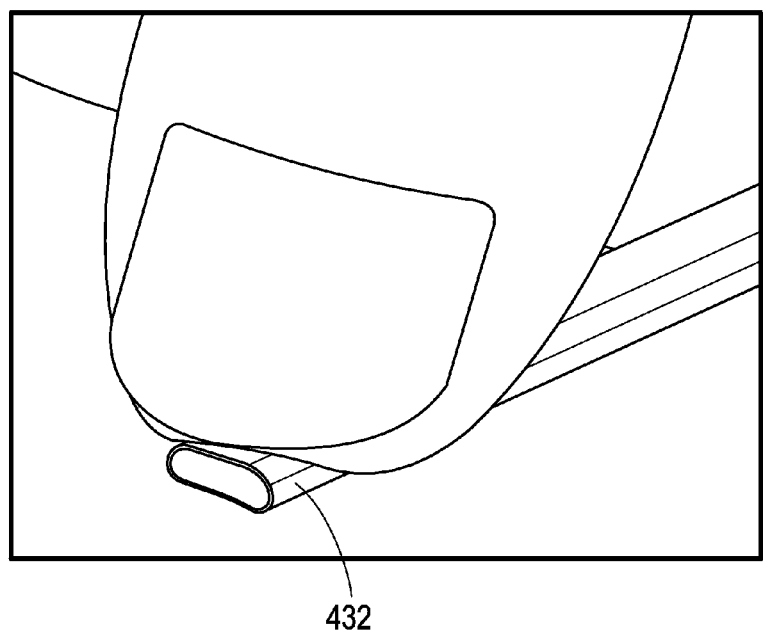
FIG. 34 is a photograph of a compressed Ni—Ti tube.
Figure 35:
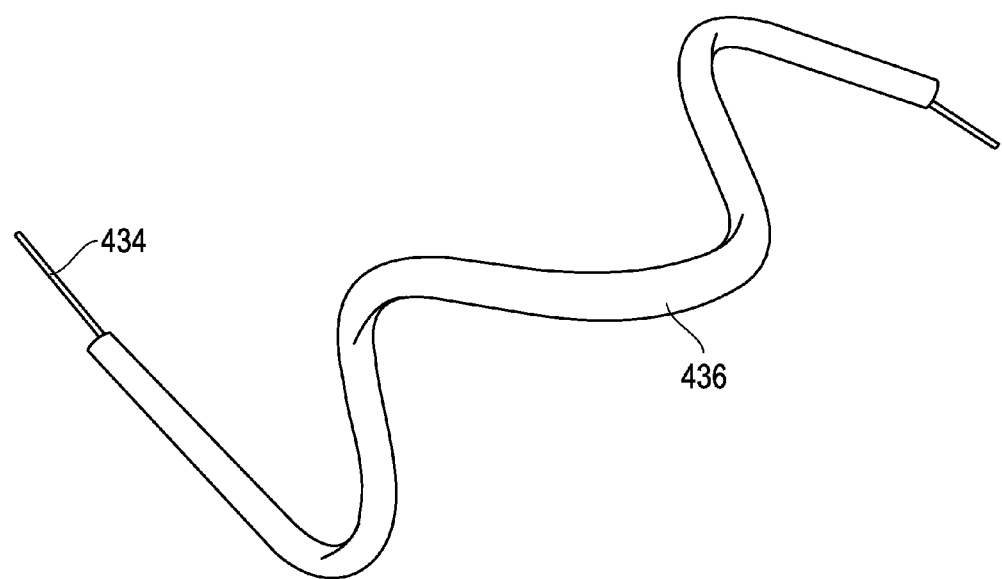
FIG. 35 is a photograph of a cable tube in an aluminum tube.
Figure 36:
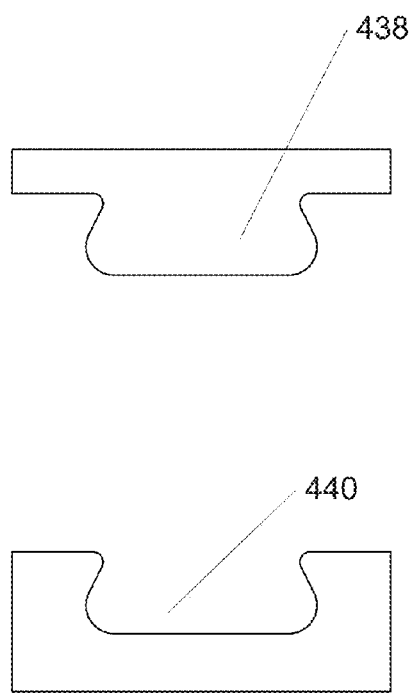
FIG. 36 depicts a tab and hole.

Scale models of rings and stylet head similar to those in FIG. 30 were made using additive manufacturing as shown in FIG. 33(*a-b*). As shown in FIG. 33(*a*), rings having tabs 358 and holes 360 interlocked securely. A ring was also fitted to grippers 384 (FIG. 33(*b*)), swiveled by swivel block 390, and compressed by compression tube 400. Rings preferably elastically recover when compressed, although in some embodiment variations, rings can be plastically deformed when compressed and expanded (expansion should then account for springback), or can be hinged. While polymer rings can be useful, metal is in many cases preferable for strength. Experiments were performed with 304 stainless rings cut from 14 gauge/0.003" wall and 8 gauge/0.008" wall hypotube; these plastically deformed when compressed. In contrast, 0.172" outer diameter (O.D.)/0.004" wall superelastic Ni—Ti tube 432 (Johnson Matthey, Wayne, Pa.) recovered elastically and completely even when squeezed more than needed (FIG. 34). Superelastic Ni—Ti is a good choice for metal DASC rings as it is widely-used in medical devices, strong, suitable for MRI-guided interventions, long-term implantable, and laser-machinable. As a potential stylet torqueable, flexible shaft, tests were performed using 0.035" O.D./0.019" I.D. superelastic Ni—Ti cable tube 434 (ACTONE®, Asahi Intecc USA, Santa Ana, Calif.); this was easily passed through bent aluminum tubing 436 about 9" long with 0.132" inner diameter (I.D.) (FIG. 35). Cable tube 434 could be rotated smoothly with good torque control.

One design parameter is the number, size, and shape of the holes (and the corresponding size and shape of the tabs). While eight (or as few as four) are adequate for some cannula shapes, other shapes (e.g., spirals) need more rings (e.g., 20-30 holes) for finer control of ring relative orientation, allowing a smoother shape. Fewer holes allow for stronger tabs such as the design of FIG. 36. In general, tabs and holes do not require a slot-shaped section as with the tabs and holes of FIG. 26; all that's needed is an undercut shape, which might be circular, truncated circular, T-shaped, L-shaped, keyhole-shaped, trapezoidal as in FIG. 36, where tab 438 fits into hole 440, etc. Another design parameter is wedge angle, which affects minimum radius of curvature. The wedge angle can vary widely; however, angles in the range of 2-10° may be preferable.

Rings can be manufactured from tubular stock by CNC milling, laser cutting, laser/waterjet cutting (e.g., using the LASER-MICROJET® process of Synova S.A. of Ecublens, Switzerland), micro-waterjet, photochemical machining, and other methods. As shown in FIG. 26, the sidewalls of the holes and tabs are preferably substantially perpendicular to a plane tangent to the ring at the centerline of the hole or tab, since sidewalls with significant draft/taper make it difficult to insert tabs into holes from both the inside and outside. Two tabs of the distal ring of FIG. 26(*a*) are not in the plane of the tubing from which they are cut, and need to be bent and/or heat set after cutting to make them perpendicular to the proximal face. The compression tube and fork (both as short as possible to navigate small cannula radii), grippers, swivel block, and any other parts that must fit inside the rings can be manufactured by methods including computer numerical control (CNC) milling, micro electrical discharge machining, laser cutting, and photochemical machining. For future 1-2 mm O.D. cannulas, the microscale metal additive manufacturing process known as MICA Freeform may be applicable to manufacturing such parts, given MICA FREEFORM™'s small features, 2 µm tolerance, and ability to produce working assemblies. Materials for these components include metals, polymers, and ceramics; magnetic resonance imaging (MRI) compatibility may be a consideration in choosing the best materials.

Figure 37:
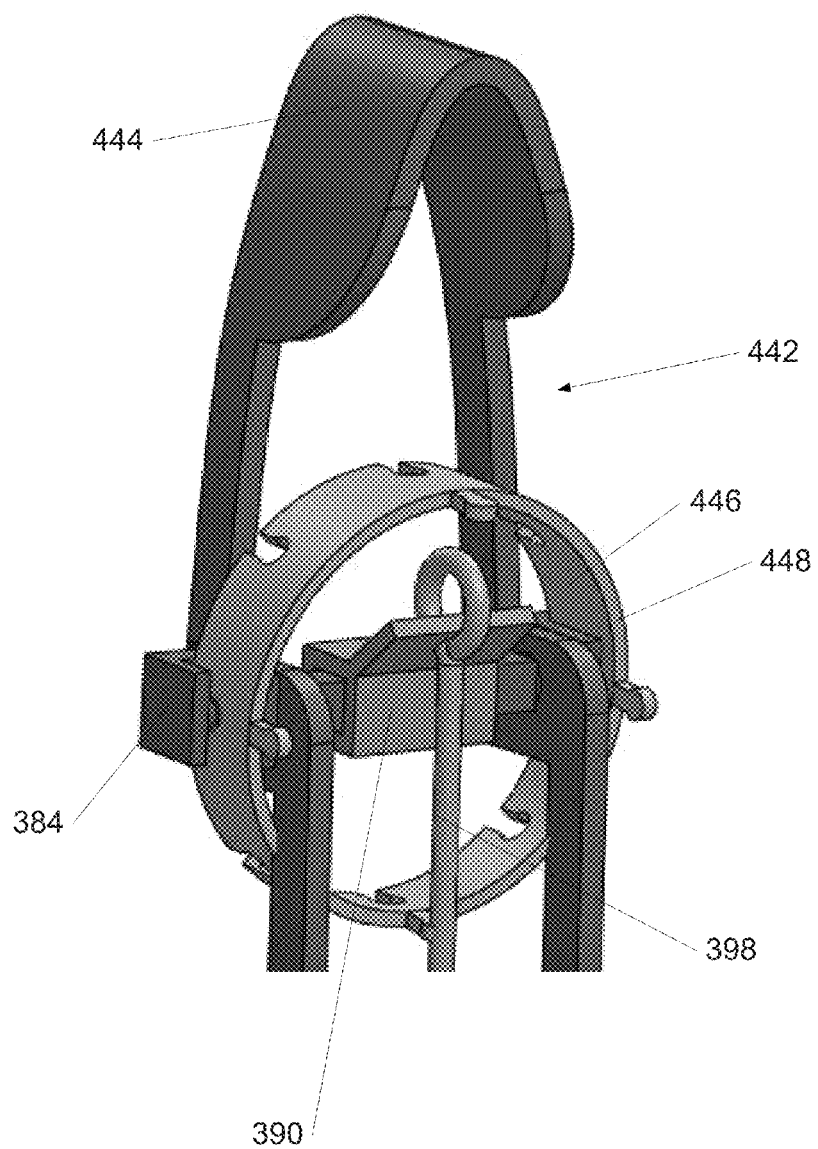
FIG. 37 depicts a stylet head.

In some embodiment variations, for example, those in which DASC grows within solid tissue vs. a liquid or gas-filled space, the fork may be modified to facilitate penetrating, cutting, and/or displacing tissue and to prevent tissue from interfering with the motion of the rings and other components. FIG. 37 shows a stylet head in which the distal end of fork 442 has been extended distally and the two flexures brought together to form a distal tip 444 which can penetrate, cut, dissect, and/or displace tissue, and which is large enough to shield ring 446 and other moving components from tissue contact, but which still allows fork 442 to be compressed or expanded. In some embodiments the distal head is rotated to enhance tissue penetration or cutting. In some embodiment variations in which the distal ring can make contact with tissue, tissue may be cut or displaced by swiveling ring 446 (which may have one edge/surface, such as the proximal face 448 sharpened at least partially) or spinning the distal head with the ring at a particular angle. In some embodiment variations, other devices for tunneling or burrowing through tissue may be provided at the distal end of the stylet, such as RF ablation electrodes, microdebrider-like teeth, pressurized water jets, or lasers.

Figure 38:
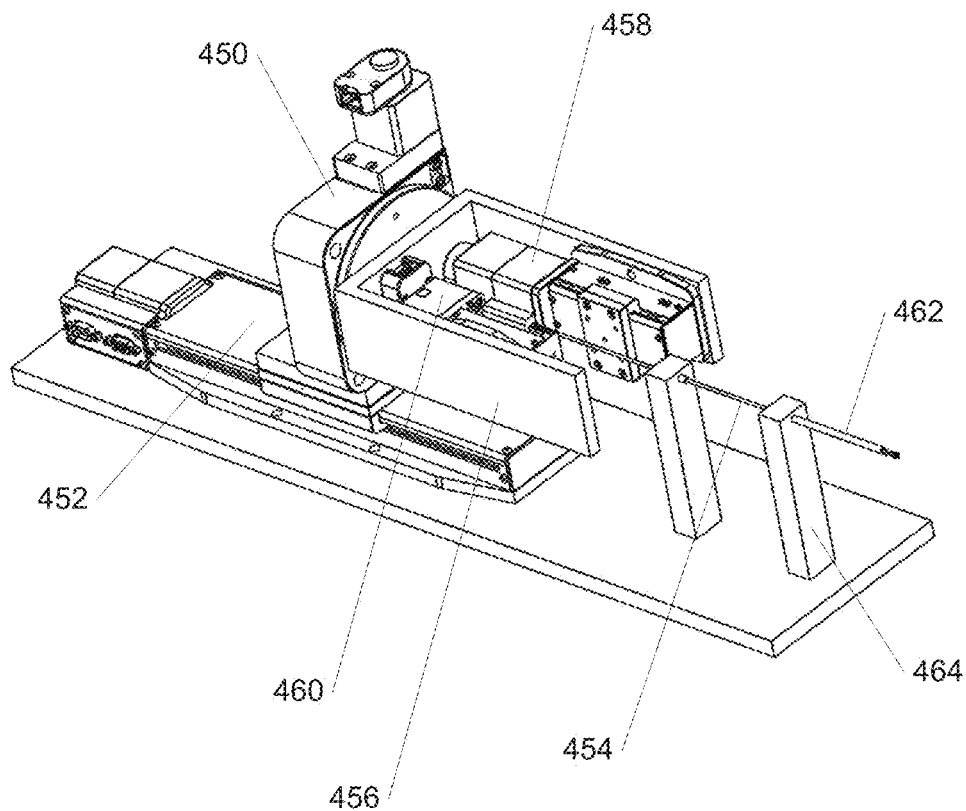
FIG. 38 depicts a robotic system.

FIG. 38 depicts a robotic system for DASC in which a set of reusable components such as stages and brackets—ultimately housed in a console unit—are interfaced to the stylet which may be disposable/single-use. A single console may accommodate different rings and accompanying stylets, which vary in ring diameter, type, length, etc. A single console may assemble and disassemble multiple cannulas. The console actuators may also be used to actuate a device used in conjunction with DASC, such as a steerable catheter passed through the DASC lumen. The console is preferably fixed in position relative to the patient. As shown in the figure, the required motions for ring assembly and disassembly can be provided, for example, by four motorized stages. Rotary stage (e.g., with slip rings) 450 mounted on linear stage 452 can serve to rotate stylet shaft 454 about its longitudinal axis to orient each ring before mating. Linear stage 452 can serve to translate the stylet distally and proximally. Rotary stage 450 can also have mounted to it, e.g. through bracket 456, two small linear stages or actuators: stage 458 to actuate the ring-swiveling wire, and stage 460 to translate the compression tube which compresses the fork. Assembled cannula 462 may be supported by support 464. In some embodiment variations, in lieu of a linear stage, the stylet shaft may be wound around a spool which is rotated to extend or retract the shaft and thus translate the stylet head, i.e., a winch configuration. The spool can itself be rotated around an axis substantially parallel to the unwound shaft, twisting the shaft to reorient rings before mating/interlocking To facilitate this with a shaft that is springy such as ACTONE cable tube, means such as a pad in contact with the wound shaft may be provided to keep the shaft in close contact with the spool.

In some embodiment variations, the stylet head is rotated by means other than twisting the stylet shaft. For example, the head can incorporate female threads with a steep pitch, and a region of the stylet shaft with matching male threads passes through the female threads. By translating the shaft axially, the head would be forced to rotate. Proximal axial translation can be achieved by pulling on the shaft with distal translation achieved by a return spring, or by a lengthening and shortening of a small bellows (e.g., Servometer, Cedar Grove, N.J.) using fluid pressure/suction.

In some embodiment variations, procedures needing more than a single cannula can use one set of actuators to assemble several cannulas in sequence. In some embodiment variations, the same actuators used to assemble/disassemble the cannula can be used to manipulate surgical tools inside the assembled cannula, or can steer the cannula's distal end in real time if flexible rings and pull wires are provided.

In some embodiment variations, the edges and corners of stylet and rings can be radiused to minimize the risk of stylet or ring catching while traversing other rings, or excessive friction (e.g., in areas of small radii). In some embodiment variations, the style head axial length is made as short as possible. In some embodiment variations, the most distal portion of the stylet head is designed to easily glide past rings when the stylet head moves distally, while keeping other components away from the inner surfaces of the cannula, where they might get caught; a proximal portion of the head might be used for a similar purpose when the head is moving proximally. In some embodiment variations, the stylet head is coated with parylene or AMC148-18 (Advanced Materials Components Express, Tyrone, Pa.)—a hard, biocompatible, low-friction coating, or provided with a biocompatible lubricant to reduce friction. In some embodiment variations, the stylet shaft is twisted by a known amount while it moves through the cannula to reduce static friction. In some embodiment variations, the stylet head is vibrated (e.g., axially) to reduce friction while passing through the cannula. In some embodiment variations, the shaft is covered with a low friction coefficient (e.g., polytetrafluoroethylene (PTFE)) sheath to make movement easier. In some embodiment variations, a liner, preferably of a low friction coefficient material such as PTFE is provided in the cannula to make movement easier. The liner can be extended gradually more distally as each ring is added (e.g., by the stylet or ring pulling it along) and can be withdrawn prior to or during cannula disassembly, for example, by pulling the liner from its proximal end. In embodiments in which the liner is not needed to aid cannula assembly but provided to make the cannula watertight, etc., the liner can be deployed after all rings are assembled, attached to the final/most distal ring, etc., and can be made from materials with higher friction coefficients such as silicone.

In some embodiment variations, the stylet head is pulled forward using a screw-like motion. The head can include a thread-like element (e.g., male or female), which engages projections or another thread (e.g., female or male) that is continuous or discontinuous on the inside of the rings or the inside of a liner. By twisting the stylet shaft, the head is twisted and advances distally or retracts proximally inside the rings. Once the head has moved distally past the most distal ring, it is free to rotate to orient the next ring or to prepare to decouple the most distal ring.

In some embodiment variations, rings may vary in size, shape, type, or function. For example, the most distal ring may incorporate a closed or partially-closed end, as long as the ring can still be deformed to pass through the cannula (unless added separately). A ring may include multiple apertures and mounting surfaces for smaller rings, allowing a single cannula to branch into one or more smaller cannulas, or allowing a steerable catheter or other device to be passed through it in a controlled fashion. The most distal ring and most proximal rings in the cannula may only have tabs but no holes, or vice-versa.

Figure 39:
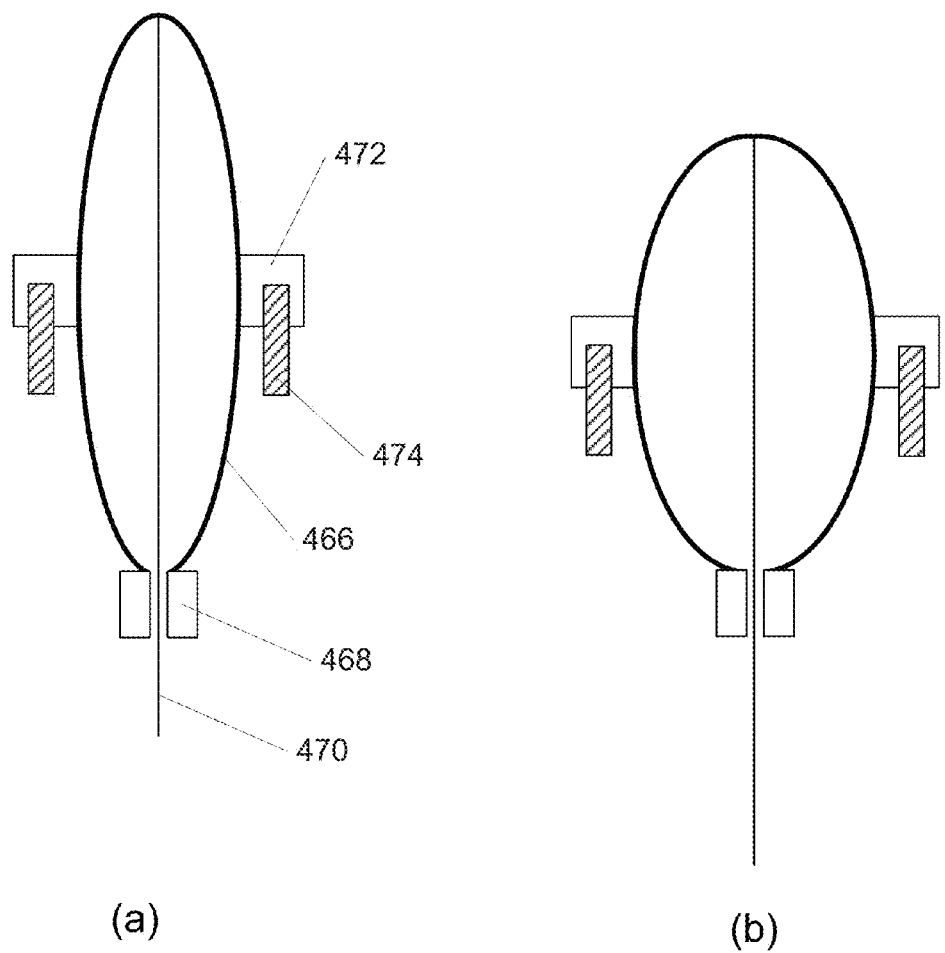
FIGS. 39(a)-(b) show apparatus for changing the shape of rings.

In general, the stylet/ring combination should be as flexible as possible so as to best navigate the cannula when moving both distally and proximally. In some embodiment variations, alternatives to a compression tube may be used to compress and expand the rings. For example, two concentric tubes may be used. One tube is fixed to the stylet shaft (and may be the shaft) while the second is coupled to the grippers through spiral leaf springs such that when the second tube is rotated relative to the first tube in the direction that tightens the spiral, the grippers are pulled radially inwards (and possibly also rotated; this can be compensated). Both tubes can be ACTONE™. Alternatively as shown in the cross-sectional view of FIG. 39, the grippers can be attached to a flexible loop or band 466 (e.g., elliptical in shape as shown) that is supported proximally by hollow stylet shaft 468 (e.g., a cable tube) and whose distal end is attached to pull wire 470. In its relaxed/unstressed state, loop 466 is elongated axially as shown in FIG. 39(*a*), causing grippers 472 to collapse ring 474: the force supplied by loop 466 is enough to deform ring 474. In FIG. 39(*b*), pull wire 470 has been pulled proximally, shortening loop 466 axially but widening it radially, and allowing ring 474 to expand to its normal circular shape. Such an arrangement may be less stiff than the compression tube arrangement described above and involves less friction as it is purely compliant. Loop 466 also may serve to penetrate, cut, dissect, and/or displace tissue, and shield ring 474 and other moving components from tissue contact as in the embodiment of FIG. 37. Other approaches may be used, such as an expanding mechanism which expands the ring along the as-expanded major axis of the ellipse by pushing against the ring from its inside; an expanding balloon with bell cranks or other linkages to modify the direction of force; a balloon that is coupled to the grippers and contracted by reducing its internal pressure; flexible elements such as wires coupled to the grippers and pulled into a tube to draw the grippers inwards, and so forth.

Figure 31:
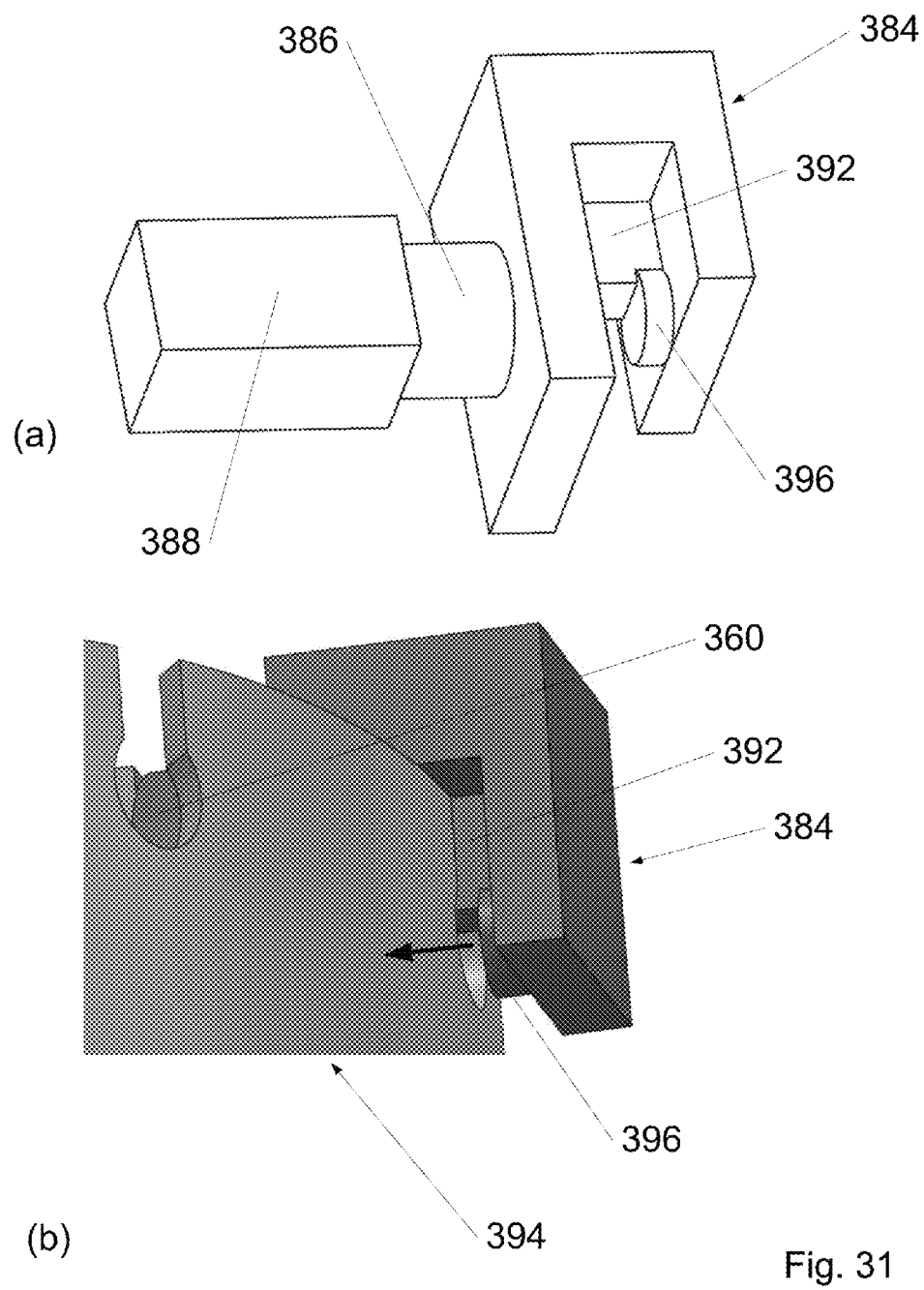
FIGS. 31(a)-(b) show details of grippers and ring.

In some embodiment variations, the gripper of FIG. 31, which is shaped so as to pass over the distal edge of the ring and compress by pushing its exterior surface inwards, is replaced by means of gripping the ring using holes, from its inside, or from its edges. For example, features may be provided on the inside of the ring, which can be grasped by suitable features on the stylet head to compress the ring. Or, a shape capable of expanding (e.g., a flexible tube or split cylinder with a translating wedge or ball) can be inserted through the holes in the ring, and then expanded to grasp the ring from its edges and pull it inwards. Or, a split cylinder having an inner region and an outer region eccentrically mounted can be inserted through a hole in the ring from the inside, and the outer portion rotated by an angle less than 360 degrees so that it can no longer be withdrawn from the hole and can pull the ring inwards along with it.

In some embodiment variations, the rings are deformed into a shape which allows movement through the cannula using a mechanism that pushes them outwards rather than pulls them inwards; such a mechanism would normally have the axis of pushing perpendicular to the axis of swiveling (which is normally parallel to the minor axis of the deformed, elliptical ring).

In some embodiment variations, the rings are elliptical in their relaxed/unstressed state and are held circular by virtue of adjacent rings or preferably, a locking mechanism. However, rings dependent on adjacent rings to maintain their shape may not interlock stably. Moreover, the force applied to rings that are more proximal by rings that are more distal and elastically deformed will tend to distort these more proximal rings. It may therefore be preferable that rings have the shape desired for the cross section of the cannula (e.g., circular) while in their relaxed state.

In some embodiment variations, in lieu of four tabs that interlock the rings three tabs may be used; this too may provide stable interlocking of the rings. However, it is challenging to deform the ring into a shape that enables it to pass through the cannula and also allows easy locking and unlocking of the tabs.

In some embodiment variations, in lieu of four tabs just two are provided, preferably parallel to either the major or minor axis of the elliptically-deformed ring. If the tabs and rings both have draft in the correct directions to allow the tabs to be inserted into the holes, the interlocked rings may be stable. However, with only two tabs holding the rings together, the cannula may be weaker, especially when subject to a bending force, compared with one having more tabs. In some embodiment variations, rather than use the tabs to provide stable interlocking in all axes (including shear), the rings are provided with additional features to provide stability that would otherwise be missing. For example, if rings include a smaller diameter tube at their proximal end which fits into the next most proximal ring distal end, stability in shear is provided, and a tab design similar to that of FIG. 26 can be satisfactory using only two tabs approximately 180 degrees apart.

In some embodiment variations, all the holes or all the holes incorporate a thin (e.g., stamped) region which prevents tabs entering holes from the outside from exiting the holes from the inside, or vice-versa, or comprise holes that are blind. In either case, stability can be achieved with just two tabs.

Figure 40:
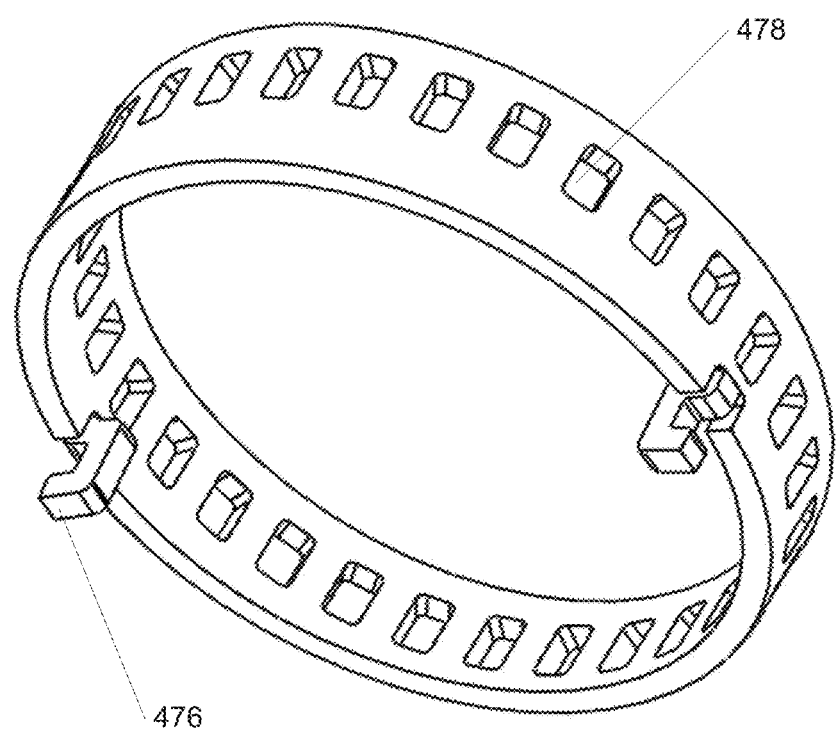
FIG. 40 shows a ring.

In some embodiment variations, the tabs can have a more complex form than those shown in FIG. 26 such that only two tabs can provide stability in shear, torsion, and tension. FIG. 40 shows a ring having tabs 476 that are C-shaped and which extend partly into the ring lumen (alternatively, such tabs can be on the outside of the ring). Such tabs can be manufactured after cutting the ring from tubing via bending. When the ring is deformed inwards at the tabs, the tabs are able to enter holes 478 in the adjacent ring from the inside, and interlock the rings stably. Or, tabs 476 can have a chamfered/ramped profile such that they are pushed inwards as the mating surfaces of the rings approach one another, allowing tabs 476 to snap into holes 478 without compressing the ring.

In some embodiment variations, the rings are not stable in shear when interlocked but are stabilized by a separate element, such as a tube (e.g., PTFE) or rod, which is slid incrementally over or through the cannula as rings are added or removed. An internal tube may be preferable to an internal one, as it avoids liquid contact with the rings if liquid is being transported by the cannula, creates a smooth, low-friction lumen through which to pass instruments, and reduces the risk of traumatizing tissue when passing a tube over the cannula. The tube could be advanced or retracted by a separate actuator or intermittently engaged and released by the stylet to advance and retract it.

In some embodiment variations, the proximal end of the ring has male threads and the distal end has female threads (or vice-versa) such that one ring can be screwed into another to interlock them, and also serve to adjust the relative angle of the rings. The axis of each thread should be perpendicular to the surface of the ring at the end that is threaded; thus, the axes of the two threads will not be parallel. In some embodiment variations, even-numbered rings have male threads at both ends or throughout, and odd-numbered rings have female threads at both ends or throughout, or vice-versa.

In some embodiment variations the cannula isn't circular in cross section, but elliptical, and the rings aren't deformed to pass through the cannula, but are elliptical in their relaxed state and simply re-oriented to fit through the cannula. Such rings can only mate with one another in two possible orientations (e.g., forming a zero or maximum curvature pair), limiting the range of possible DASC shapes if all rings are identical. However, if multiple versions of the rings are provided in which the orientation of the wedge angle relative to the ellipse major and minor axes varies, more complex 3-D shapes can be provided if the DASC robotic system is able to select and deliver the appropriate ring at each location.

In some embodiment variations—rather than being deformed into an elliptical shape prior to passing through the cannula (or having an elliptical state in their relaxed state), rings can be circular or otherwise shaped and sufficiently compliant such that when oriented with the ring axis approximately 90 degrees to the cannula axis, the ring is compressed into a sufficiently narrow shape by the cannula itself (i.e., the rings that comprise it) so it can pass through it. When rings are so oriented, their distal/leading surface is curved, facilitating passage and compression. To enhance this effect, rings may be stiff axially but flexible radially.

Figure 41:
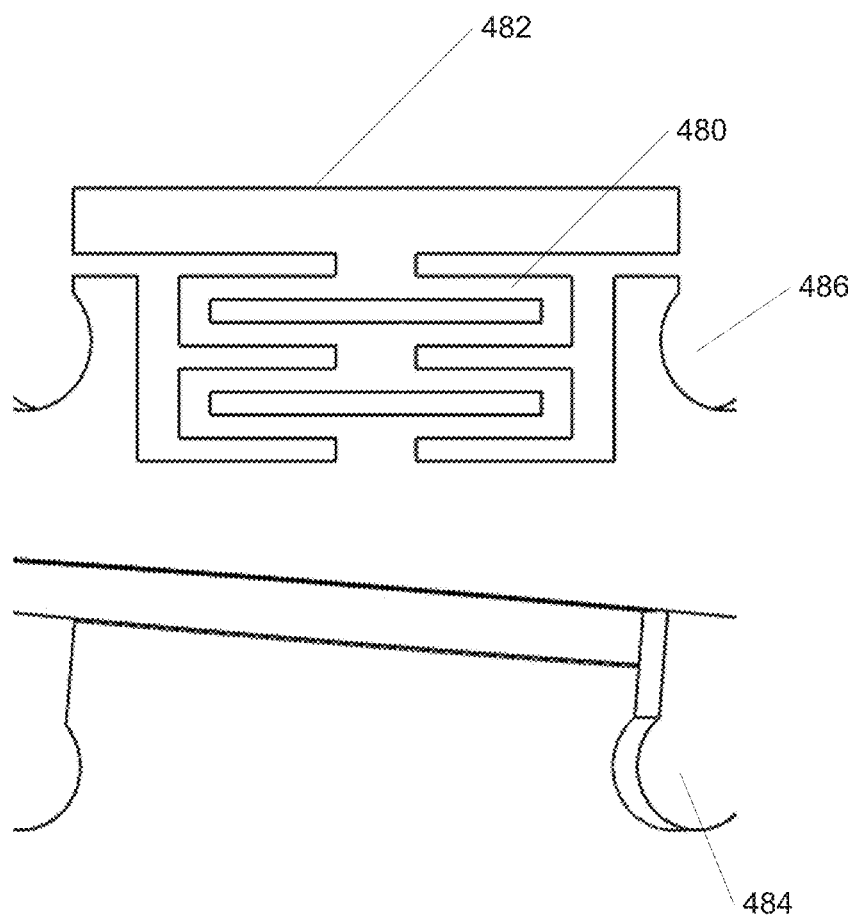
FIG. 41 shows a detail of a ring with flexures.

In some embodiment variations, cannula rigidity may be enhanced by reducing clearances between rings and/or by designing the rings to be mutually preloaded as-assembled (e.g., by tensioning the stylet shaft), and/or by post-tensioning the rings using wires running from the most proximal to the most distal ring. In some embodiment variations, rings may not be coupled (e.g., by tabs and holes) but simply held together by tension in one or more wires. FIG. 41 shows a close-up view of a ring incorporating side flexures 480 (e.g., laser-cut) to provide preloading of distal face 482 against the adjacent ring when the rings are interlocked. The mating, preloaded ring faces minimize axial backlash, while the simultaneous preloading of circular tab 484 against the circular (or v-shaped) distal surface of hole 486 preloads the joint in shear and torsion. In some embodiment variations, tabs such as tab 484 may be made flexible so that they may be preloaded against holes such as hole 486. If desired, means of preloading such as the flexures of FIG. 41 may also be used to couple rings together if suitable (e.g., L-shaped) catches and holes are provided: rings may be pushed together, given a twist, and then released.

In some embodiment variations, a single cannula is comprised of rings that are different from one another. Such variations may include shape, diameter, height, and wedge angle; number, shape, and type of tabs and holes; incorporation of flexural and/or preloading features; and material, among other variations. For example, some regions of the cannula, such as the distal end, may incorporate metallic rings that are flexible due to the incorporation of flexural elements (e.g., like the flexures of FIG. 41) or because they are made from a flexible material such as an elastomer. Such regions can be passively flexible, allowing compliance and reduced trauma if contacting tissue, during a procedure, for example, or in an implanted device. Or, if provided with means of actuation, such regions can have adjustable stiffness or be able to be articulated or steered. For example, a flexible region near the distal end of the cannula can allow the distal tip to be deflected in real time, much like a flexible endoscope tip, by providing tension wires or cables to at least one ring and pulling on these with appropriate tensions. Flexible regions may be entirely comprised of flexible rings (e.g., with parallel faces), or have only some of the rings flexible, e.g., a series of alternating flexible and (axially) rigid rings may be used.

In some embodiment variations, in lieu of the ring shapes of FIG. 26 in which one face is normal to the ring axis and one is at another angle to the axis, both faces can be an angle other than 90 degrees to the axis.

In some embodiment variations, direct imaging of the cannula as it is being extended can be achieved by incorporating a fiber optic bundle in the stylet, such as surrounding the stylet shaft, or forming the shaft. Alternatively, an imaging sensor such as, e.g., a complementary metal-oxide-semiconductor (CMOS) or charge coupled display (CCD) device, or an ultrasonic transducer, could be incorporated into the stylet, such as attached to the top surface of the swivel block, allowing panning and tilting of the field of view to be achieved by swiveling the block and tilting the stylet shaft, respectively. For example, while the block is oriented as in FIG. 32(f), a sensor mounted parallel to the currently most distal surface of the block would image the path ahead, allowing the clinical controlling the cannula to select a ring orientation, through an appropriate interface, before mating/coupling the ring. In the stylet head configuration of FIG. 37, the tip of the fork can incorporate an imaging system, such as an imaging sensor and optics. To aid in visualization, fluid such as saline or air can be provided to the region between imaging sensor and tissue to wash away debris, displace blood, etc.

In some embodiment variations, DASC can be assembled over a guidewire or other structure, or within a catheter or other structure. To allow for assembly over a structure, the stylet can be designed differently than shown in FIG. 30 and may be hollow, and the rings can be notched to allow them to be swiveled as much as in FIG. 32(d), or simply swiveling to a different angle so as not to intersect the structure. With appropriate sensing (e.g., optical, mechanical) the local direction of the structure (e.g., guidewire or cannula) can be sensed and the appropriate ring orientation selected such that the trajectory of the DASC cannula substantially matches that of the structure inside or surrounding it. In the case of the structure being an anatomical structure such as a blood vessel, duct, or cochlea, DASC can be extended so as to remain centered in the lumen, minimizing wall contact and potential issues such as damage to the intimal surface, thrombus, and inflammation.

In some embodiment variations, DASC rings may be pre-oriented according to the desired cannula shape such that they may be delivered through the cannula and joined to the growing distal end with little or no rotation by the stylet required.

In some embodiment variations, DASC rings may comprise a shape memory allow and transform from one shape into another by heating or cooling. For example, a ring may be circular in axial cross section at elevated temperature, and elliptical in axial cross section at a lower temperature. For example, the ring may remain relatively cool while it is transported through the cannula, but upon exiting and coming into contact with body tissue or fluid, the ring may warm and transform its shape. A source of heating or cooling may also be used; for example, the stylet may be heated or cooled and by contact with a ring thereby heat or cool the ring.

In some embodiment variations, DASC rings comprise different numbers of tabs and holes, and transform into shapes that are not substantially elliptical. For example, a ring may transform into a rounded triangular shape having tabs at the vertices and at the midpoint of each side, and couple with another ring (e.g., circular) by deforming such that the tabs at the vertices enter holes in the other ring from the outside, and the tabs at the midpoints enter the holes from the inside.

In some embodiment variations, DASC rings are designed for low radial stiffness but high axial stiffness. For example, a ring can be corrugated or scored (e.g., by etching, milling, laser engraving) so that it deforms easily into an ellipse. The corrugation and/or scoring can be very localized since the major and minor axes of the ellipse are normally the same for all rings: as few as two scoring lines aligned with the major axis can be sufficient.

In some embodiment variations, the proximal end of DASC is outside the patient's body, while in other embodiment variations, the proximal end is within the patient's body, for example, attached to a rigid tube, flexible catheter (e.g., one that is anchored), anatomical structure such as bone, implant, etc.

In some embodiment variations, the holes in the rings are blind so that the rings may form a substantially leak-proof conduit when assembled. Alternatively, the holes may be through holes, but a liner is affixed (e.g., by bonding) to the rings on the interior and/or exterior to provide sealing. To improve sealing, the rings may be made from a soft material such as an elastomer, or have elastomeric mating surfaces. In some embodiment variations, rings made from a hard material such as metal alternate with rings made from a soft material such as silicone rubber, to provide sealing. In some embodiment variations, the soft rings are essentially gaskets which are individually placed during DASC assembly or attached to rings on either the proximal or distal faces, or both.

In some embodiment variations in which DASC remains in the place, e.g., as an implant, DASC can be detached once deployed, by methods including mechanical decoupling, fracturing, electrolytic dissolution, melting, and so forth.

18th Embodiment

A corrugated, bellows-like tube may be provided initially in an axially-compressed state, compressed configuration. The tube may be extended by advancing the distal end distally, carrying with it the folded corrugations, while allowing corrugations to unfold and lengthen from the proximal end. By varying the extent of unfolding at different circumferential locations, the direction in which the distal end moves can be controlled, steering the tube as it lengthens.

19$^{th}$ Embodiment

An everting flexible tube as in the 8$^{th}$ Embodiment, comprised of a material that can be stiffened locally can be deployed into a cannula of complex 3-D shape by incrementally or continuously feeding the inner walls in a distal direction by an amount that may differ circumferentially, and stiffening the tube locally upon its eversion to form outer walls. For example, the tube may comprise a photopolymer that is initially flexible but which is rigidified by exposure to ultraviolet or visible light, e.g., produced by a ring-shaped light that surrounds the inner walls at the growing distal end. The resulting outer walls are thus rendered stiff, retaining the local curvature, if any, produced when the inner walls were everted and passed the ring. Unless the stiffening is reversible, such a cannula may be permanently deployed.

In a similar manner, the outer walls of a braided everting tube (e.g., made from superelastic nickel-titanium) may be locally stiffened and locked into position once formed by locking the wires of the braid to one another, preventing relative motion. For example, selected wires may be resistance or laser welded to one another on the outer walls; this can be done as the inner walls are fed distally by an amount that may differ circumferentially, and everted to form the outer walls.

Ramifications:

In lieu of a DASC instrument that is substantially constant in diameter as has been illustrated herein, in some embodiments DASC has a tapered shape (e.g., smaller at the distal end). If the taper angle is relatively large, rings may be transported through the cannula without the need to compress and swivel them to fit, or require less compression and/or swiveling.

In some embodiments, multiple DASC devices may be used simultaneously in a procedure, either with the distal ends in different target regions or in the same target region but (e.g., with different approach angles). For example, two DASC devices in the same region with different approach angles can allow for triangulation useful in suturing, tissue, retraction, etc.

In lieu of transporting material to the distal end of DASC through a lumen to extend it, in some embodiments material can be transported over (on the outside of) DASC, or alongside DASC, e.g., using DASC as a rail or guide for the material transport. In some embodiments, material necessary to extend DASC is obtained from the environment.

In some embodiments, the DASC lumen can be subdivided by inserting tubing after the desired shape has been assembled, or gradually as it is being assembled. For example, four tubes may be passed through the cannula: one for irrigation with saline, one providing a working channel for an instrument, and one providing a channel for an endoscope, and one providing a channel for a fiber optic illuminator. The remaining space in the lumen can then be used for aspiration.

In some embodiment variations, to minimize the time required for the stylet to connect a ring and/or make a long trip back to the ring stack to pick up another ring (or drop off another ring if disassembling the catheter), the rings can be stored more distally within the gradually-extending cannula. For example, rings can be held in a compressed state (e.g., within a tube, one behind the other) located inside the cannula. Such rings could be pushed out by a plunger. Or, rings could be held within a frame designed to allow the grippers to engage them and separate them from the frame: the rings may need to be oriented with the major axis of the compressed, substantially elliptical ring at an angle to the cannula axis to facilitate this.

In some embodiments, rather than storing rings proximally as in FIG. 30 and transporting them through the entire assembled length of the cannula (e.g., from the groin to the heart) as in FIG. 29 to reach the distal end where they are assembled, the rings may be stored within the cannula such that the most distal of such stored rings is stored far closer to the distal end. This can speed the assembly and disassembly processes, especially when it difficult to store rings in a stack such as stack 378 inside the body.

Figure 43A:
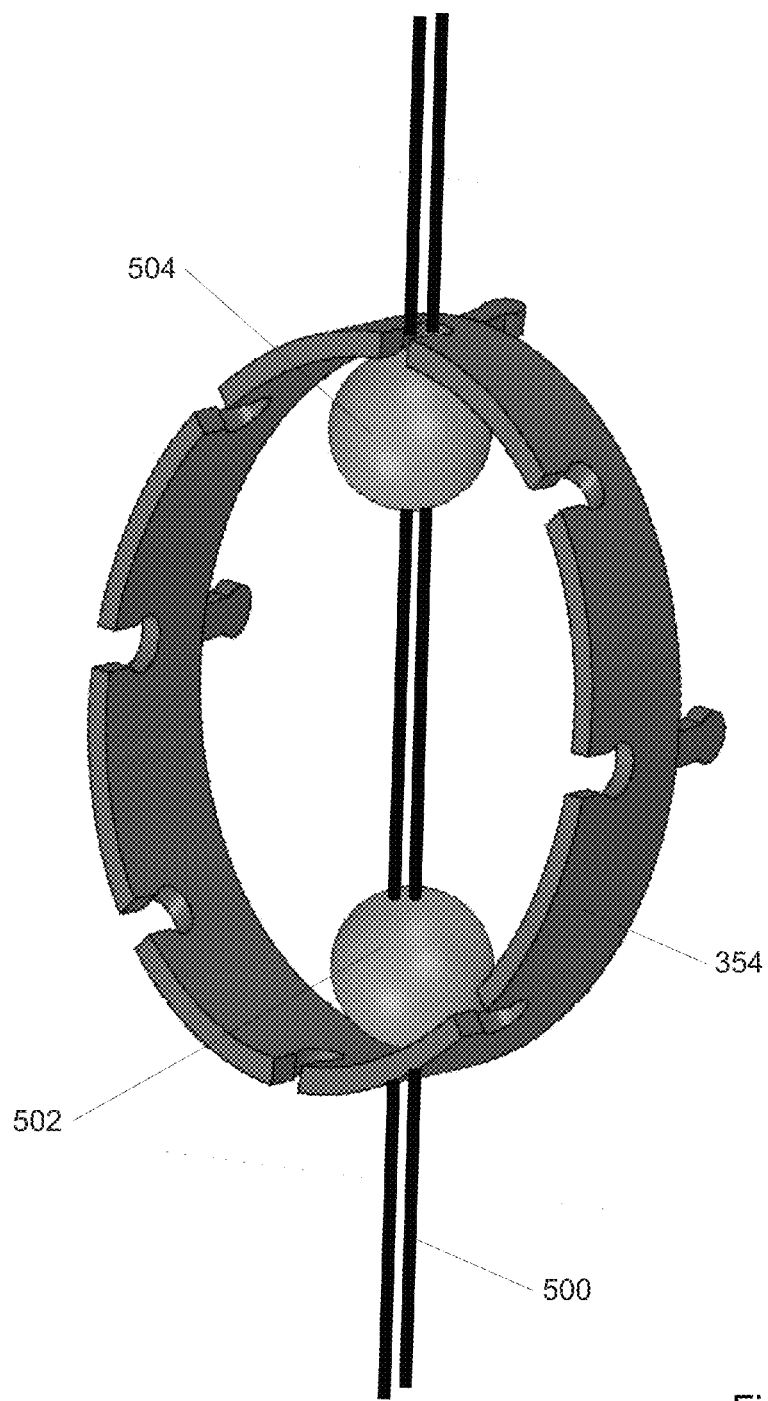
FIGS. 43(a) and 43(b) show a storage element for rings.
Figure 43B:
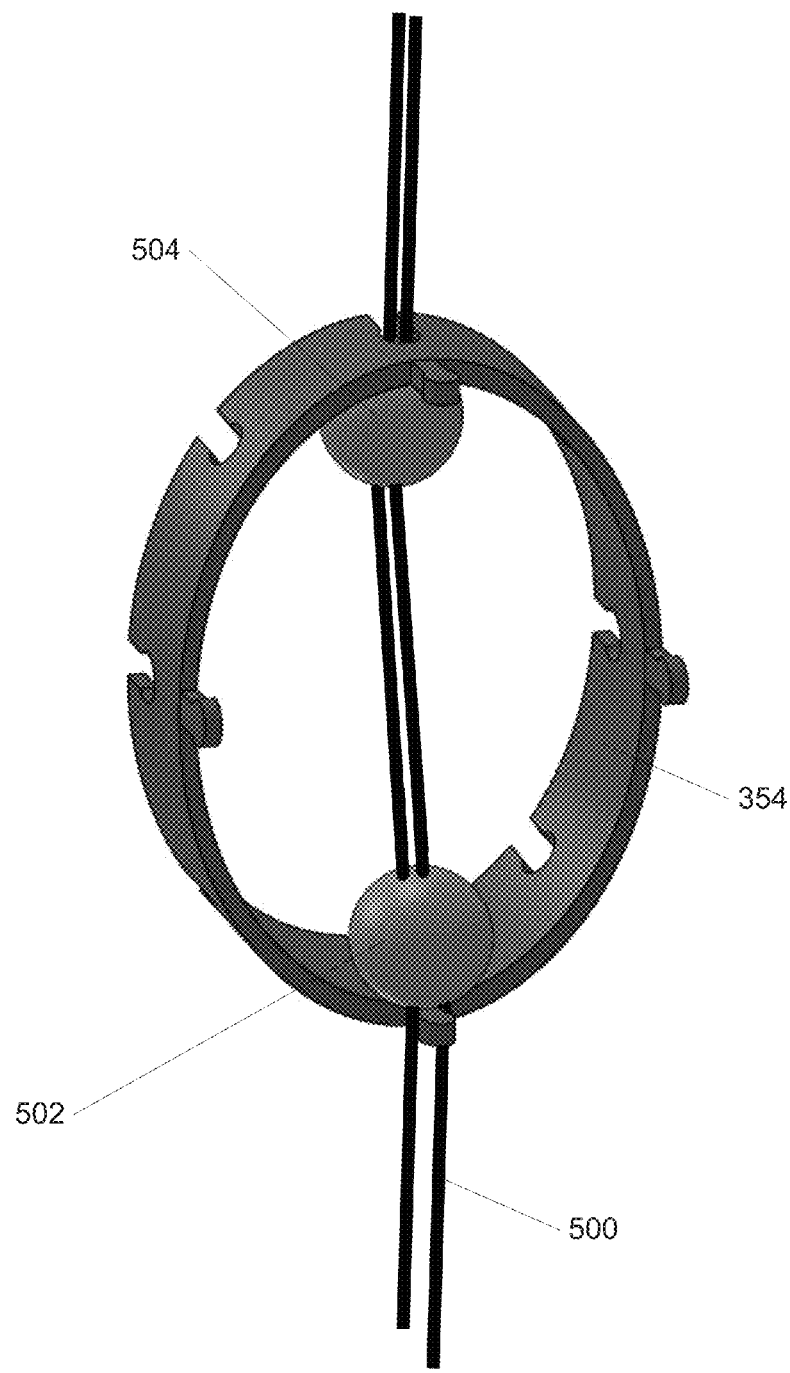
Figure 44:
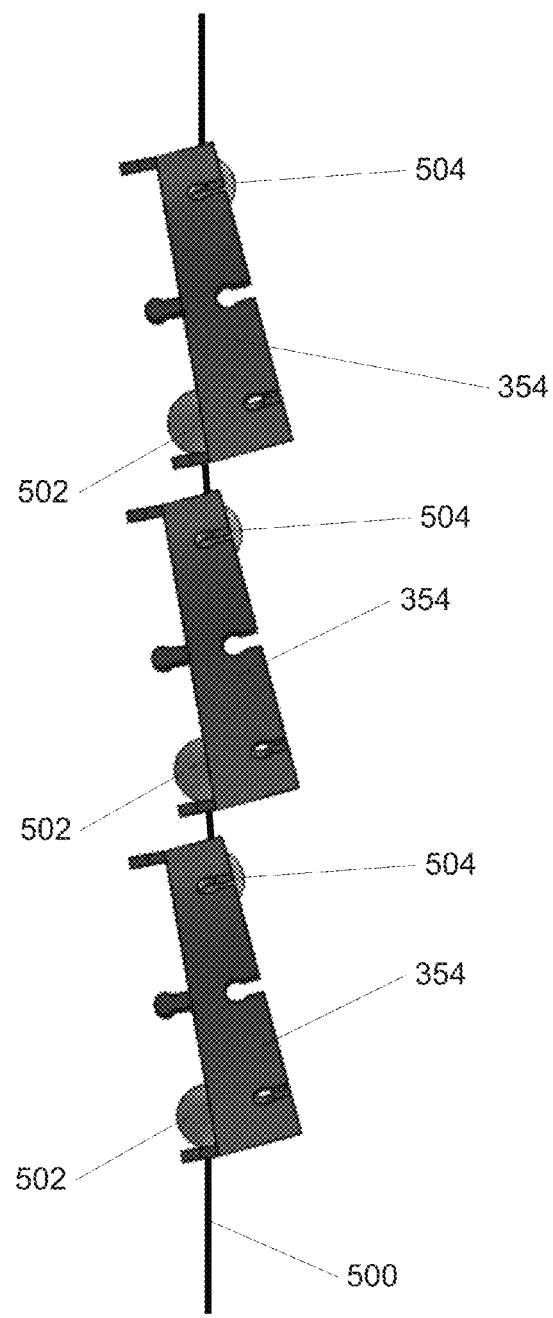
FIG. 44 shows a group of rings in a cannula.

In some embodiment variations, rings may be plastically deformed into a compressed form that allows them to be stored within the cannula adjacent to one another, or if their major axes are tilted with respect to the local cannula axis, with some overlap. In other embodiment variations, the rings are elastically deformed into an elliptical shape and retain that shape within the cannula without the aid of the stylet by means of a storage element. For example, as shown in FIGS. 43(a) and (b), the storage element may comprise a pair of cables with a set of suitably-spaced bumps, knots, or other projections (e.g., balls 502 and 504 as shown) along its length. If the cables pass through a ring, then by rotating and deforming the ring into an elliptical shape, it may be retained in that shape (if the cables are under tension) by fitting the cables into hole 360 at the distal end and around tab 358 at the proximal end, such that balls 502 and 504 press against the proximal and distal inner surfaces of the ring, respectively. Multiple deformed rings can be placed along the storage element as in FIG. 44, and the element and rings can be located within the cannula, such that a suitably designed stylet can grasp the most distal ring (e.g., compressing it slightly to make it more elliptical and loosen the pressure of the balls) and transport it distally to the distal end of the growing cannula, where it can be assembled. As the cannula lengthens, the storage element may be advanced so that the most distal stored ring is close to the distal end of the cannula. Disassembly from the distal end may also be performed, with the stylet returning the rings to the storage element, and if desired, the element can retract gradually as the cannula shortens. FIG. 44 depicts rings of the same kind; in practice rings of both types shown in FIG. 26 may alternate.

In some embodiment variations, the cables in the storage element are replaced by rigid segments terminating in balls such as balls 502 and 504, and a flexible element connects ball 504 of one segment with ball 502 of the next most distal segment. In such variations, the overall storage element need not be under tension, since the rigid segments and balls maintain the rings in the proper elliptical shape, and the storage element can bend in 3-D to follow the cannula shape.

In some embodiment variations, features such as notches may be added to the rings to engage the cable or rigid segments. For example, slots may be added to the proximal and distal edges of the rings adjacent to the holes and tabs used for interlocking, and the storage element can engage these. In some embodiment variations features may also be added to rings and/or balls (or other protrusions) to positively secure the rings (e.g., not releasing them until they are made even more elliptical). In some embodiment variations, a single cable may be used, with tab 358 slotted to allow the cable to enter it.

Figure 45:
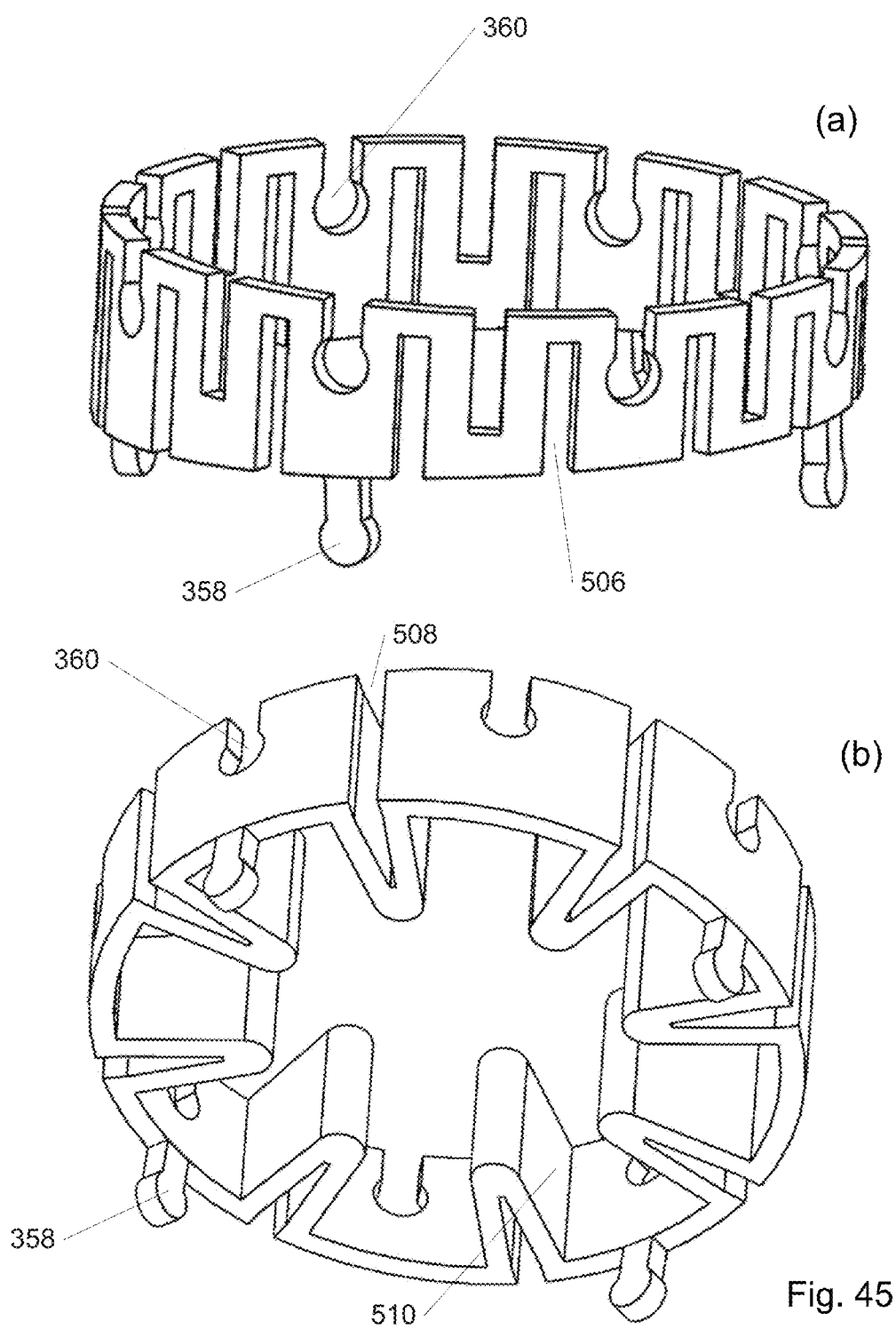
FIG. 45 shows expandable rings.

FIG. 45 depicts wedge-shaped rings having tabs and holes similar to ring 354 of FIG. 26, but which can be expanded from a smaller diameter, shown in the figure, to a larger diameter (not shown), thus allowing unexpanded rings to pass distally through the lumen of the cannula comprising already-assembled rings, and then, at the distal end of the cannula, be oriented at the desired angle, expanded, and interlocked to the cannula. The expansion of the ring(s) can involve plastic deformation, or if a locking mechanism is provided, can involve an elastic deformation. Over-expansion of the ring(s) to accommodate spring-back of the material can also be provided. FIG. 45(a) depicts a version of the expandable ring comprising four tabs and eight holes (however, the number of each can vary) wherein cuts 506 in the wall of the ring (which normally would have filleted corners for stress reduction) allow the ring to be stretched to a larger diameter, somewhat like a stent (e.g., through plastic deformation). FIG. 45(b) depicts a version (also comprising four tabs and eight holes, for example) wherein cuts 508 are provided and the cut edges of the ring are joined by internal hinges (e.g., plastically-deformable) 510 which also allow the ring to be stretched to a larger diameter. The stretching may be performed by a balloon or other expanding element, or by other means, and the assembly of the rings can be performed in a process similar to that of FIG. 14, but in which each rings is oriented such that the tabs enter holes in the next most proximal ring as the expansion occurs, locking the ring in place. Since, due to the wedge angle at which the ring mates with the next most proximal ring varies according to the ring orientation, the balloon or other element should accommodate the variable wedge angle, e.g., through compliance in the balloon or its attachment to a shaft or stylet such as tube 190. A cannula produced this way can be permanent (e.g., for use in an implant), or if the rings are plastically deformed as-stretched and means of re-compressing and withdrawing them through the cannula are provided, then the cannula can be disassembled after use.

Since the rings can change in diameter, there is no need to deform them into elliptical shapes and swivel them as in the 17$^{th}$ Embodiment. This can facilitate use of a cannula comprising such rings within solid tissue or within other environments in which there is little or no room beyond the circular confines of the distal cannula end as it evolves. If a balloon is used to expand the rings, it can serve a further purpose in displacing surrounding material (e.g., bluntly dissect tissue) to make room for the ring.

In some embodiments, rings such as those in the 17$^{th}$ Embodiment may be tethered to cables or wires to that they may be retrieved in case they are dropped inside a patient. The cables may be remain attached as long as the cannula is assembled (e.g., with the cables lying alongside the inner wall of the cannula, possibly sandwiched by a liner), or removed after assembly.

In lieu of using tabs and holes such as those shown in FIG. 26 to interlock rings, in some embodiments rings may have features which lock together when the rings are mated are twisted through a small angle. Or, in some embodiments rings may be elliptical in shape when unstressed, and be joined together in pairs such that a smaller outside diameter on the face of one ring can fit inside a larger inside diameter of an adjacent ring. Initially the rings may be mated with their major axes substantially parallel, after which one may be rotated relative to the other through an angle (e.g., 90°) such that both rings are both forced into substantially circular shapes, and remain interlocked by virtue of friction or the inclusion of locking features. In lieu of the rings of FIG. 26 having solely holes or tabs on their opposite faces, in some embodiments they may have a mixture of tabs and holes.

In some embodiments rings have built-in curvatures (including rings of zero curvature in which the distal and proximal faces are parallel), much like groups of at least two rings of the kind shown in FIG. 26 have built-in curvatures. Appropriate selection and oriented assembly of such rings can produce a complexly-curved cannula.

In some embodiments, rings may be compressed and remain compressed when desired, or expanded and remain expanded when desired, by designing them to be bistable, with stable configurations of different diameters. For example, a ring may have an expanded shape similar to that of an open umbrella, and a compressed shape similar to that of an umbrella which has turned inside out.

The various embodiments of the invention, set forth explicitly herein or otherwise ascertained from the teachings herein, may be used alone or in any combination.

Medical Applications:

A variety of medical procedures may benefit from the use of instruments such as those described herein to introduce and/or remove fluid, or provide a conduit for the delivery or retrieval of implants or instruments to or from a target region of the body. For example, cancer patients may have brachytherapy seeds implanted in or near tumors, have tissue biopsied or fluid aspirated for analysis, receive chemotherapy agents, or have tumors removed or ablated. Brachytherapy seeds are normally implanted at multiple sites. Biopsies or fluid aspiration may be performed in multiple locations. Chemotherapy is often delivered intravenously but can be more effective if delivered locally to the site of a tumor, minimizing systemic effects. Patients with atrial fibrillation may be treated by electrical ablation of selected regions of heart tissue. Patients in need of neuromodulation may be implanted with electrodes or other devices.

Devices such as those described herein may be made in different sizes, ranging from sub-millimeter in diameter to several centimeters or even larger.

As noted, devices such as those described herein may be used to deliver brachytherapy seeds. In some embodiments, multiple seeds may be loaded into the inner walls of a cannula at a desired axial spacing, and retained by the walls. As the instrument everts, it lengthens and delivers seed after seed into tissue. Such an instrument may extend for a distance, then retract, then extend in a different direction.

Devices such as those described herein may deliver other implants to tissue surfaces or sub-surface; delivery need not be through solid tissue.

Devices such as those described herein may be used to deliver devices which remove or ablate tissue—mechanically, or through laser, thermal, RF, microwave, or cryogenic means, for example.

Devices such as those described herein may deliver drugs such as chemotherapy drugs or pain medication, for example, or embolic particles, microspheres, and other materials. A device might tunnel through tissue and selected regions of organs such as the liver to form a complex 3-D shape that is "space filling" and dispense a drug or ablation agent through holes along the device, in a process akin to drip irrigation. Such a 3-D device might also be used to simultaneously ablate large volumes of unwanted tissue using chemical, radio frequency, ultrasonic, cryogenic, or other means.

Devices such as those described herein may be used for lung biopsy, avoiding delicate structures and minimizing the risk of pneumothorax.

Devices such as those described herein may be used for fine needle aspiration.

Devices such as those described herein may be used to deliver electrodes, or as implanted electrodes for neurostimulation, including deep brain stimulation. For example, a cochlear implant electrode that is atraumatically delivered within the cochlea and which has a large number of discrete electrodes can be distally assembled in a tapered or small diameter cylindrical shape matching that of the cochlea. Such a device may be based on an everting tube, a set of discrete tubes or rings, etc. If comprised of metal (e.g., Pt—Ir, stainless steel, nickel-titanium) rings as in FIG. 26 or FIG. 45, for example, the rings may be electrically insulated from one another by dielectric (e.g., elastomer) rings or gaskets/spacers, or at least one face (distal or proximal) of at least some rings can incorporate a dielectric material, to electrically isolate rings or groups of rings. Electrical connection to the metal rings can be achieved after the implant is delivered by atraumatically sliding into the lumen of the hollow electrode a multi-conductor cable with, for example, brushes that make contact to the rings from their interior surfaces. Separately, electrodes that grow into or around tissue, such as nerve cuff electrodes that wrap around a nerve as they distally assemble, may be used implemented using approaches discussed herein, so as to minimize the size of incision needed to deliver them, achieve more intimate contact with tissue, etc.

For some applications, devices such as those disclosed herein and their component parts may be perforated, textured, coated, or otherwise modified to improve the reaction or compatibility with tissue, such as minimizing the risk of thrombus, discouraging bacterial growth, encouraging tissue or bone growth, etc.

For some applications, devices such as those disclosed herein—or attached members such as catheters—may be stabilized, positioned (e.g., centered), and/or anchored inside a patient's body at one or more locations by an inflatable balloon, deployment of fixation devices, etc. For example, a balloon may be used on a device in its proximal region, while the distal region grows into the desired shape.

Devices such as those described herein may be used in minimally-invasive procedures such as sinus surgery and arthroscopic surgery.

Devices such as those described herein may be used within the ventricles of the brain to ablate/remove tumors, biopsy tissue, treat hydrocephalus, or provide injections. In addition, such devices may be used to cool the brain after stroke or other trauma: a cooling liquid compatible with cerebrospinal fluid can be introduced through a flexible catheter deployed within the device, with warm fluid withdrawn through the (e.g., annular) space surrounding the catheter. Fluids can pass through holes in the walls of the devices, or the device can be provided with a liner such that flow is directed through the end of the device and/or other locations. The device can be inserted through a small incision in the skull into the anterior horn of a lateral ventricle, and deployed toward the posterior horn and if desired, into the inferior horn. After deployment, or in some embodiment variations, during deployment, fluid exchange can occur, allowing the brain—and only the brain—to be efficiently cooled from within. Appropriate sealing may be used to prevent cerebrospinal fluid loss during deployment/assembly or retrieval/disassembly of the device and during operation.

Devices such as those described herein may be used in spinal surgery, for example, for microdiscectomy or foraminal stenosis, navigating around obstacles in small spaces. A distally assembled cannula might, for example, be used to provide percutaneous access to a laterally herniated cervical disc through a posterior approach while avoiding sensitive structures; this would avoid the need for the vertebral fusion of a frontal approach. Devices such as those described herein may also be used to "grow" an interbody fusion cage (e.g., with a helical shape) between two vertebral bodies. Since such a cage is distally assembled in-vivo, it can be delivered through a small incision.

Devices such as those described herein may be used in the treatment of atrial fibrillation by ablation (e.g., RF or cryoablation) of the wall of the heart. Such devices may be used to position an ablation electrode or other device against the heart wall during a procedure, or provide a stable platform for a steerable catheter, or may themselves act as an ablation device. For example, a device having a circular or other suitable shape can be deployed within the heart around the pulmonary vein and provided with RF energy or cryogenic cooling, and can be anchored to the heart wall during the procedure, so that it moves with the heart, or moved in synchrony with the heart. Force sensing can also be provided, e.g., by incorporating one or more rings with strain gauges into the device.

Devices such as those described herein may be used in the delivery of enteral feeding tubes through the pyloric sphincter of the stomach, to achieve transpyloric placement.

Devices such as those described herein may be used in urology for stone removal and to correct urinary drainage.

Devices such as those described herein may be used to deliver and affix tissue approximation and closure devices, e.g., in cardiology.

Devices such as those described herein may be used in injections of anesthetics, for example, for epidural spinal anesthesia.

Figure 42:
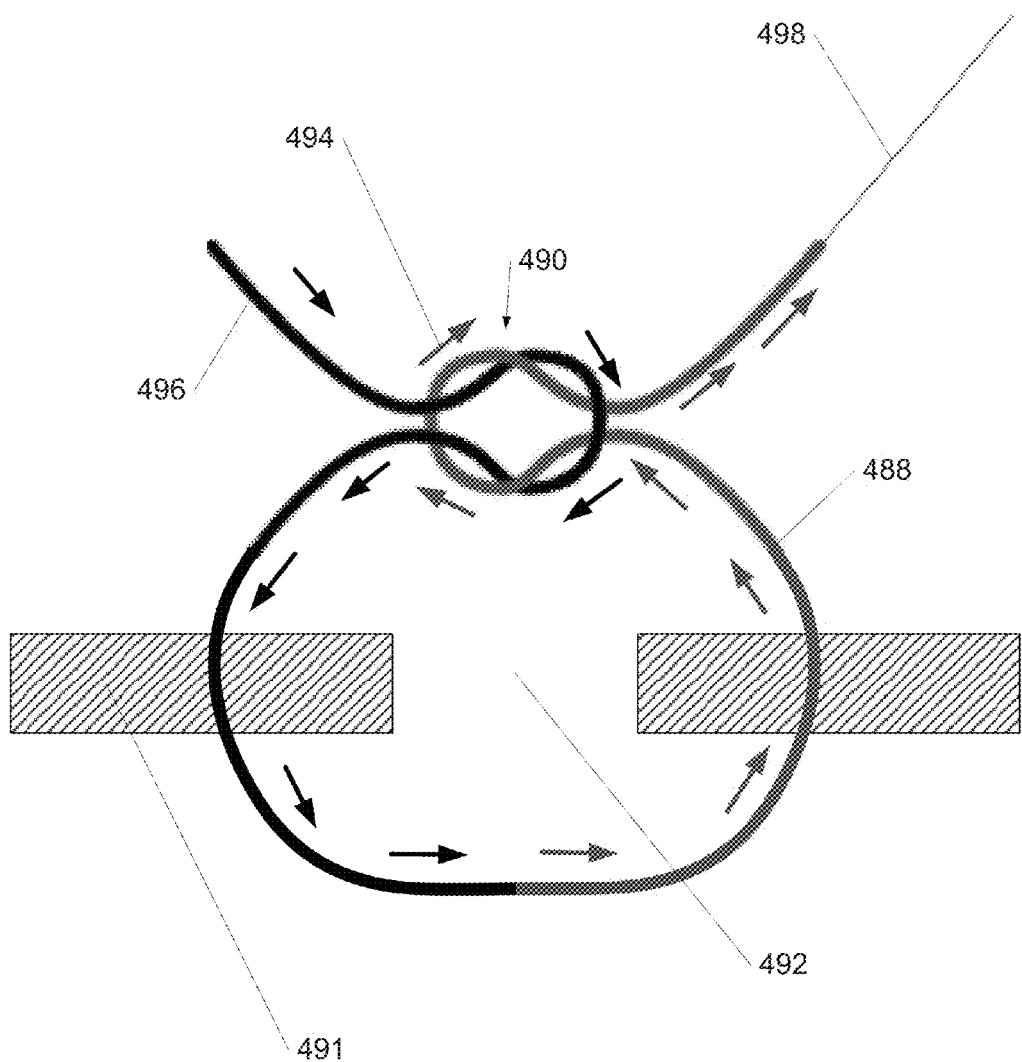
FIG. 42 shows a method of suturing and knotting.

Devices such as those described herein may be used to deliver sutures and similar materials, and form knots in suture. FIG. 42 depicts a cannula formed into a shape that includes a loop 488 and a square knot 490 (or another knot, such as a surgeon's knot). The proximal and distal sections of the cannula are shown differently shaded for clarity. Loop 488 passes through two walls of tissue 491 separated by gap 492, and the clinical objective is to approximate walls 491 to as to close gap 492. To accomplish this, as shown by cannula growth direction arrows 494, the cannula is assembled starting at proximal end 496, then forms a small loop that will later serve as one half of square knot 490, then continues to grow while penetrating through one wall of the tissue (in some embodiments a sharp stylet may be temporarily used to pierce the tissue), then through the other wall of tissue, then finishes the loop and grows to form the other half of square knot 490. Suture 498 is delivered through the cannula either gradually as it is assembled (similar to the way DASC can be assembled over a guidewire, described herein), or after the entire shape has been assembled (e.g., attached to the most distal ring, if DASC comprises rings). Once the distal end of suture 498 is anchored, the cannula can be disassembled over the suture, resulting in suture 498 having the shape of the cannula, i.e., manifesting a loop and tied into a square knot. The loop can then be tightened to approximate the tissue, and the knot tightened to keep the tissue approximated. Thus, the normally complex and difficult procedure of forming a loop and tying a knot when performed endoscopically can be achieved relatively automatically by DASC, and in spaces such as the upper airways where space is highly constrained.

Devices such as those described herein may be used to treat atrial fibrillation for example as follows: The device may be delivered into/extend into the left atrium of the heart and guide/support a steerable catheter, or itself adopt a shape (e.g., loop-like) in the distal region, with the distal region in contact with the atrium surrounding the ostia of the pulmonary veins (more than a single vein can be surrounded at a time). By applying energy (e.g., RF) through the device, tissue can be ablated such that electrical conduction paths contributing to fibrillation are interrupted.

Devices such as those described herein may be used to place epicardial leads on the heart, e.g., for biventricular pacing.

Devices such as those described herein may be used as annuloplasty rings, for example, to correct mitral valve regurgitation. The device can be inserted percutaneously through a small incision, enter the beating or stopped heart, and grow inside the heart into the complex 3-D shape required to reshape the valve annulus. The device would be anchored to tissue by one method of another. For example, if the device comprises rings such as those of FIG. 26, at least some rings can include barbs, clips, or other fixation features which grasp and/or penetrate the tissue. Attachment of tissue to the ring can occur after the ring is fully assembled, or gradually, as the ring grows. Barbs, clips, suture, and mechanisms for attaching the device to tissue can be passed through the lumen of the device, passed over it, or alongside it. In some embodiments, the distal end of the annuloplasty ring can interlock with its side to form a strong, closed loop.

Devices such as those described herein may be used to perform percutaneous bypass surgery, e.g., of peripheral arteries or coronary arteries. The device can create a proximal anastomosis to, for example, the aorta, e.g., by compressing the aorta wall between two rings such as those of FIG. 26, possibly specially adapted for this task. The device can then extend along a 3-D path to reach the target vessel and a distal anastomosis can be created with that vessel, e.g., using similar methods. Means of perforating the vessels can be provided, e.g., a stylet head of the kind shown in FIG. 37, or a separate sharp stylet passed through the device. Compression of vessel tissue between rings may be used to necrose tissue and create a hole. Modified (e.g., sharpened) versions of rings such as those of FIG. 26 can be used to cut holes in vessels, e.g., when rotated by the stylet.

Devices such as those described herein may be used as stents, stent grafts, shunts (e.g., aneurysm bypass shunts), conduits, and other implants through which bodily fluids pass, and which are intended to provide a patent lumen. For example, stents of adjustable length and curvature can be produced using multiple rings of the kind shown in FIG. 26, and stents for bifurcations can be assembled out of separate, coupled rings.

Devices such as those described herein may be used within the lumens of blood and other vessels to help navigate a guidewire or catheter through difficult bifurcations, tortuosity, calcification, or other complex anatomy, for example, in the brain.

Devices such as those described herein may be used in lieu of a guidewire, or in procedures that do not require a guidewire, in interventional radiology and other procedures within body lumens. Devices such as those described herein may be used in navigating tortuous vasculature such as in the brain, and for filling the sacs of neurovascular aneurysms in lieu of detachable coils.

In general, devices used in conjunction with instruments such as those described herein may be may be slid over the instrument. Or, devices and materials may be passed through a lumen in the instrument. Or, the instrument may be used as a platform to support another instrument at its distal end which is desired for a procedure (e.g., a biopsy or ablation device).

Non-Medical Applications:

Devices such as those described herein may be used as robotic arms and manipulators.

Devices such as those described herein may be used for oil and gas exploration and production.

Devices such as those described herein may be used in civil engineering and architecture to create useful structures.

Devices such as those described herein may be used to navigate through irregular debris in search and rescue operations, (e.g., in collapsed mines, collapsed buildings). A device (e.g., with an outside diameter in the range of 10-40 mm) can navigate autonomously or under operator control to grow in a complex 3-D shape through nooks and crannies (e.g., using a camera, laser-based instruments) to reach trapped disaster victims before heavy machinery can remove rubble to free them. It can deploy sensors along the way or upon reaching its destination, allowing its position and that of the victims to be identified. Through the lumen, air, water, food (e.g., in liquid form), and medical supplies can be furnished to the victims, and cameras and two-way communication devices can be delivered, allowing continuous communications. To facilitate its ability to extend through various materials at the disaster site, the device can be provided with a powerful vacuum system and if needed, an airproof liner, so that dust, dirt, and smaller rocks and debris can be extracted through it. When no alternative presents itself, a drill can be deployed through the device, driven hydraulically or using a rotating flexible shaft, allowing penetration of hard materials. The device can also serve to deploy reinforcing cables that stabilize heavy debris at risk of shifting and collapsing on the victims, e.g., during rescue operations.

Devices such as those described herein (e.g., with a larger diameter than would be used for a medical application) may be used for disaster-related cleanup of hazardous environments, e.g., nuclear reactor sites, where they can deployed through available openings, extend through stairwells without having to climb stairs or fly like a mobile robot that consumes power, all the while being immune to hazards such as gamma radiation (since there are no electronics required to grow and maneuver). Through the lumen cleaning agents can be delivered, and debris can be vacuumed up, among other useful operations.

Devices such as those described herein may be used underwater to help clean and repair the hulls of large ships.

Devices such as those described herein may be used to travel through complex 3-D spaces such as piping networks.

Devices such as those described herein may be used to navigate around or through an object for purposes of inspection, delivery or retrieval of materials, etc.

Devices such as those described herein may be used to explore tunnels, trenches, crevices, fissures, and otherwise difficult-to-navigate areas. Such areas may be underwater or extraterrestrial, e.g., exploring deep ocean trenches or crevices on Mars. Devices such as those described herein may be used as a form of kinetic sculpture.

Devices such as those described herein may be used as toys, for example, in a construction set allowing complex 3-D tunnels to be quickly assembled (e.g., through which marbles may be released). In such uses, circular rings similar to those of FIG. 26 may be replaced by non-circular rings of different shapes (e.g., square, octagonal, triangular), and interlocking may involve manually compressing the rings and releasing them when their tabs (some or all) are within an adjacent ring. Moreover, if the toy is constructed from its distal end, to which the user has access, and there is therefore no reason to transport rings through its interior, then the rings can be pre-curved and/or much longer than would otherwise be possible. It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context. In certain embodiments, the present invention may also include methods and compositions in which the transition phrase "consisting essentially of" or "consisting of" may also be used.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. DiMaio, S and Salcudean, S. Needle insertion modeling and simulation, IEEE Trans. Robot. Autom., vol. 19, pp. 864-875, 2003.
2. Glozman, D. and Shoham, M., Image-guided robotic flexible needle steering, IEEE Trans. Robot., vol. 23, pp. 459-467, 2007.
3. Okazawa, S., Ebrahimi, R., Chuang, J., Salcudean, S., Rohling, R., Hand-held steerable needle device, IEEE/ASME Trans. Mechatron., vol. 10, pp. 285-296, 2005.
4. Webster, R. Kim, J., Cowan, N., Chirikjian, G., Okamura, A., Nonholonomic modeling of needle steering, Int. J. Robot. Res., vol. 25, pp. 509-525, 2006.
5. Majewicz, A., Marra, S., van Vledder, M., Lin, M., Choti, M., Song, D., Okamura, A. Behavior of Tip-Steerable Needles in ex vivo and in vivo Tissue, IEEE Trans Biomed Eng. 2012 October; 59(10):2705-2715. PMID: 22711767.
6. Goksel, O., Dehghan, E., Salcudean, S. Modeling and simulation of flexible needles. Medical Engineering & Physics, 2009, 7:1153-1162. PMID: 19674926.
7. Sears, P. and Dupont, P. A steerable needle technology using curved concentric tubes, Proceedings of the 2006 IEEE/RSJ International Conference on Intelligent Robots and Systems (IROS), Beijing, China, Oct. 9-15, 2006: 2850-2856. PMID: 23685532.
8. Dupont, P., Lock, J., Itkowitz, B., Butler, E. Design and control of concentric tube robots, IEEE Transactions Robotics, vol. 26(2): 209-225, 2010. PMID: 21258648. http://www.ncbi.nlm.nih.gov/pmc/articles/PMC3022350/pdf/nihms-251097.pdf.
9. Dupont, P., Gosline, A., Vasilyev, N., Lock, J., Butler, E., Folk, C., Cohen, A., Veeramani, A., Wu, M., Schmitz, G., Chen, R., del Nido, P. Concentric tube robots for minimally invasive surgery. Hamlyn Symposium on Medical robotics: 3-4, 2012. http://www.bioeng.nus.edu.sg/biomm/pdfs/dupont2012concentricHamlyn.pdf.
10. Webster, R., Romano, J., Cowan, N. Mechanics of pre-curved-tube continuum robots. IEEE Transactions Robotics, vol. 25(1): 67-78, 2009.
11. Gosline A., Vasilyev N. V., Butler, E., Folk, C., Cohen, A., Chen, R., Lang, N., del Nido, P. J., Dupont, P. E. Percutaneous intracardiac beating-heart surgery using metal MEMS tissue approximation tools. Int J Robotics Research 2012; 31:1081-1093. PMID: 23750066, PMCID: PMC3671619 (available Aug. 1, 2013).
12. Mahvash M. and Zenati, M. Toward a hybrid snake robot for single-port surgery, 33rd Annual International Conference of the IEEE EMBS, Boston, Mass., Aug. 30-Sep. 3, 2011:5372-5375. PMID: 22255552.
13. Lee, W., Chamorro III, Andres, Weitzner, B., Robotically controlled medical instrument, U.S. Pat. No. 7,854,738 (2010).
14. Saadat, V., Ewers, R., Chen, C. Shape lockable apparatus and method for advancing an instrument through unsupported anatomy, U.S. Pat. No. 7,128,708 (2006).
15. Degani, A., Choset, H., Wolf, A., Ota, T., Zenati, M. Percutaneous intrapericardial interventions using a highly articulated robotic probe, Proceedings of the 2006 IEEE/RAS-EMBS International Conference on Biomedical Robotics and Biomechatronics, February, 2006, pp. 7-12.
16. Chapman, M., Tokota, T., Ota, T., Tully, S., Schwartzman, D., Zubiate, B., Wright, C., Choset, H., Zenati, M. A highly articulated robotic system (CardioARM) is safer than a rigid system for intrapericardial intervention in a porcine model, in In: IEEE ICRA Full Day Workshop. IEEE, Anchorage (2010).
17. Ohline, R., Tartaglia, J., Belson, A., Roth, A., Keller, W., Anderson, S., Julian, C. Tendon-driven endoscope and methods of insertion, U.S. Pat. No. 6,858,005 (2005).
18. Konstantin, B., Pauker, F., Viebach, T. Everting tube comprising two-component lubricant, U.S. Patent Application # US2008/0058596 (2007).

What is claimed is:

1. An elongatable, steerable apparatus capable of growing from a proximal end to a distal end through a process of assembly wherein one or more segments are added to the distal end of the apparatus, the apparatus comprising:
   a first segment having a lumen therethrough, the first segment having a proximal end and a distal end;
   a segment transporter that delivers one or more additional segments to the first segment through the lumen of the first and any subsequent segment; and
   a second segment having a lumen, a proximal end, and a distal end, wherein the second segment is attached to the distal end of the first segment by the segment transporter, and wherein the second segment is capable of changing a growth direction of the distal end of the apparatus and of one or more subsequent segments.

2. The apparatus of claim 1, wherein additional segments are transferred to the distal end through the lumen formed of at least one of the first, the second and one or more subsequent segments.

3. The apparatus of claim 1, wherein the growth is the result of everting a tube formed by the two or more segments.

4. The apparatus of claim 1, wherein the growth is the result of transferring additional segments to the distal end.

5. The apparatus of claim 1, wherein the at least first, second or subsequent segments are at least one of triangular, circular, elliptical, polygonal, rectangular, square, or combination thereof.

6. The apparatus of claim 1, wherein the at least first, second or subsequent segments comprise at least one of plastic, metal, rubber, latex, polymer, composite, elastomer, thermoplastic elastomer, synthetic rubber, natural rubber, melt processable rubber, propylene oxide elastomer, ethylene-isoprene elastomer, elastic polyvinyl chloride, silicone elastomer, elastic polyurethane, ethylene-vinyl acetate elastomer, or non-polymeric elastomer.

7. The apparatus of claim 1, wherein the at least first, second or subsequent segments are metal and comprise at least one of titanium, vanadium, aluminum, nickel, tantalum, zirconium, chromium, silver, gold, silicon, magnesium, niobium, scandium, platinum, cobalt, palladium, manganese, molybdenum and alloys thereof, zirconium-titanium-tantalum alloys, superelastic nickel-titanium, or stainless steel.

8. The apparatus of claim 1, wherein the segment transporter is defined further as a stylet that is at least one of a superelastic nickel-titanium, stainless steel, plastic, thermoplastic, elastomer, polyethylene terephthalate, polyethylene terephtalate glycol-modified, rubber, vinyl, latex, or silicone.

9. The apparatus of claim 1, wherein the at least first, second, subsequent segments, or a cannula is radiopaque.

10. The apparatus of claim 1, wherein the at least first, second, or subsequent segments, may attach or interlock to each other by friction, abrasive contact surfaces, self-adhesive strips, hook and loop fasteners, hooks and eyes, ties, tabs, holes, buckles, belts, pins, elastic bands, rubber bands, snaps, clasps, snap-lock, or hook and loop tape fasteners.

11. The apparatus of claim 1, wherein the at least first, second, or subsequent segments, are wedge-shaped and an addition of subsequent segments causes an extension of the apparatus at the distal end with a segment that is not wedge-shaped, a segment that is wedge-shaped on the distal or the proximal face, or a segment that is wedge-shaped on both the distal and proximal faces.

12. The apparatus of claim 1, wherein the at least first, second, or subsequent segments, are wedge-shaped having a wedge angle that varies from 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, or 85 degrees at one or both ends.

13. The apparatus of claim 1, wherein the at least first, second, or subsequent segments, are wedge-shaped and the segments interlock in increments of 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, 85, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, or 360 degrees about a longitudinal axis of the apparatus.

14. The apparatus of claim 1, wherein the at least first, second, or subsequent segments, are wedge-shaped but also tapered along a longitudinal axis of the apparatus to expand or decrease an inner diameter of the apparatus.

15. The apparatus of claim 1, wherein a central cannula is defined further as a having a proximal and distal end, wherein the segment transporter travels back and forth within the cannula to at least one of compress, swivel, transport, rotate, or add the subsequent segments to the distal end of the apparatus.

16. The apparatus of claim 1, wherein a cannula is pre-loaded with some or all the segments necessary to reach a pre-determined length and shape.

17. A method of lengthening and steering an apparatus capable of growing from a proximal end to a distal end through a process of assembly wherein one or more segments are added to the distal end of the apparatus, the method comprising:
obtaining a first segment having a lumen therethrough, the first segment having a proximal end and a distal end; and
adding a second segment having a lumen, a proximal end, and a distal end, wherein the second segment is attached to the distal end of the first segment by a segment transporter, wherein the segment transporter delivers one or more additional segments to the first segment through the lumen of the first and any subsequent segment, and wherein the second segment is capable of changing a growth direction of the distal end of the apparatus and of one or more subsequent segments.

18. The method of claim 17, wherein additional segments are transferred to the distal end through the lumen formed of at least one of the first, the second and one or more subsequent segments.

19. The method of claim 17, wherein the growth is the result of everting a tube formed by the two or more segments.

20. The method of claim 17, wherein the growth is the result of transferring additional segments to the distal end.

21. The method of claim 17, wherein the at least first, second or subsequent segments are at least one of triangular, circular, elliptical, polygonal, rectangular, square, or combination thereof.

22. The method of claim 17, wherein the at least first, second or subsequent segments comprise at least one of plastic, metal, rubber, latex, polymer, composite, elastomer, thermoplastic elastomer, synthetic rubber, natural rubber, melt processable rubber, propylene oxide elastomer, ethylene-isoprene elastomer, elastic polyvinyl chloride, silicone elastomer, elastic polyurethane, ethylene-vinyl acetate elastomer, or non-polymeric elastomer.

23. The method of claim 17, wherein the at least first, second or subsequent segments are metal and comprise at least one of titanium, vanadium, aluminum, nickel, tantalum, zirconium, chromium, silver, gold, silicon, magnesium, niobium, scandium, platinum, cobalt, palladium, manganese, molybdenum and alloys thereof, zirconium-titanium-tantalum alloys, superelastic nickel-titanium, or stainless steel.

24. The method of claim 17, wherein the segment transporter is defined further as a stylet that is at least one of a superelastic nickel-titanium, stainless steel, plastic, thermoplastic, elastomer, polyethylene terephthalate, polyethylene terephtalate glycol-modified, rubber, vinyl, latex, or silicone.

25. The method of claim 17, wherein the at least first, second, subsequent segments, or a cannula is radiopaque.

26. The method of claim 17, wherein the at least first, second, or subsequent segments, may attach or interlock to each other by friction, abrasive contact surfaces, self-adhesive strips, hook and loop fasteners, hooks and eyes, ties, tabs, holes, buckles, belts, pins, elastic bands, rubber bands, snaps, clasps, snap-lock, or hook and loop fasteners.

27. The method of claim 17, wherein the at least first, second, or subsequent segments, are wedge-shaped and an addition of subsequent segments causes an extension of the apparatus at the distal end with a segment that is not wedge-shaped, a segment that is wedge-shaped on the distal or the proximal face, or a segment that is wedge-shaped on both the distal and proximal faces.

28. The method of claim 17, wherein the at least first, second, or subsequent segments, are wedge-shaped having a wedge angle that varies from 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, or 85 degrees at one or both ends.

29. The method of claim 17, wherein the at least first, second, or subsequent segments, are wedge-shaped and the segments interlock in increments of 0, 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20, 22, 22.5, 25, 33, 33.3, 35, 40, 42.5, 45, 50, 60, 66.6, 70, 75, 80, 85, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, or 360 degrees about a longitudinal axis of the apparatus.

30. The method of claim 17, wherein the at least first, second, or subsequent segments, are wedge-shaped but also tapered along a longitudinal axis of the apparatus to expand or decrease an inner diameter of the apparatus.

31. The method of claim 17, wherein a central cannula is defined further as a having a proximal and distal end, wherein the segment transporter travels back and forth within the cannula to at least one of compress, swivel, transport, rotate, or add the subsequent segments to the distal end of the apparatus.

32. The method of claim 17, wherein a cannula is pre-loaded with some or all the segments necessary to reach a pre-determined length and shape.

\* \* \* \* \*